United States Patent
Lee et al.

(10) Patent No.: US 11,479,549 B2
(45) Date of Patent: Oct. 25, 2022

(54) NITROGEN-CONTAINING CYCLIC COMPOUND AND COLOR CONVERSION FILM COMPRISING SAME

(71) Applicant: LG CHEM, LTD., Seoul (KR)

(72) Inventors: Milim Lee, Daejeon (KR); Seonkyoung Son, Daejeon (KR); Cheol Jun Song, Daejeon (KR); Minju Kim, Daejeon (KR); Hoyong Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 140 days.

(21) Appl. No.: 16/640,286

(22) PCT Filed: Apr. 22, 2019

(86) PCT No.: PCT/KR2019/004828
§ 371 (c)(1),
(2) Date: Feb. 19, 2020

(87) PCT Pub. No.: WO2019/216574
PCT Pub. Date: Nov. 14, 2019

(65) Prior Publication Data
US 2020/0407352 A1    Dec. 31, 2020

(30) Foreign Application Priority Data
May 11, 2018  (KR) ........................ 10-2018-0054357

(51) Int. Cl.
| C08K 5/46 | (2006.01) |
| C07F 7/08 | (2006.01) |
| F21V 8/00 | (2006.01) |
| C07D 417/04 | (2006.01) |
| C08K 5/544 | (2006.01) |

(52) U.S. Cl.
CPC .......... C07D 417/04 (2013.01); C07F 7/0812 (2013.01); C08K 5/46 (2013.01); C08K 5/5477 (2021.01); G02B 6/005 (2013.01)

(58) Field of Classification Search
CPC ...... C07D 417/04; C08K 5/46; C08K 5/5442; G02B 6/005; C07F 7/0812
See application file for complete search history.

(56) References Cited

U.S. PATENT DOCUMENTS

| 2014/0311566 A1 | 10/2014 | Zhang et al. |
| 2017/0062730 A1 | 3/2017 | Ahn et al. |

(Continued)

FOREIGN PATENT DOCUMENTS

| CN | 103833507 A | 6/2014 |
| JP | 2006-045398 A | 2/2006 |
| JP | 2008-231051 A | 10/2008 |

(Continued)

OTHER PUBLICATIONS

Search Report and Written Opinion issued for PCT/KR2019/004828 dated Jul. 24, 2019, 7 pages.

(Continued)

*Primary Examiner* — Bijan Ahvazi
(74) *Attorney, Agent, or Firm* — Rothwell, Figg, Ernst & Manbeck, P.C.

(57) ABSTRACT

The present specification relates to a compound containing nitrogen, and a color conversion film, a backlight unit, and a display device, including the same.

16 Claims, 1 Drawing Sheet

(56) References Cited

U.S. PATENT DOCUMENTS

2017/0155054 A1    6/2017  Kim et al.
2017/0349822 A1*  12/2017  Lee ..................... G02F 1/1335

FOREIGN PATENT DOCUMENTS

| KR | 10-2015-0127548 A |   | 11/2015 |
| KR | 10-2017-0064132 A |   | 6/2017 |
| KR | 10-2018-0007097 A |   | 1/2018 |
| KR | 20180007097 A | * | 1/2018 |

OTHER PUBLICATIONS

Wu et al., "Novel 2,1,3-benzothiadiazole derivatives used as selective fluorescent and colorimetric sensors for fluoride ion", Dyes and Pigments 2016, vol. 124, pp. 268-276.
Chen, et al., "Aggregation-induced emission on benzothiadiazole dyads with large third-order optical nonlinearity†", Physical chemistry Chemical Physics 2013, vol. 15, pp. 12660-12666.

* cited by examiner

[Figure 1]
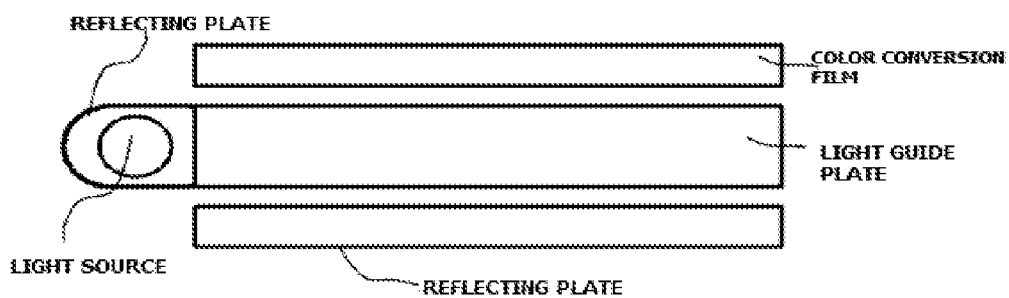
[Figure 2]
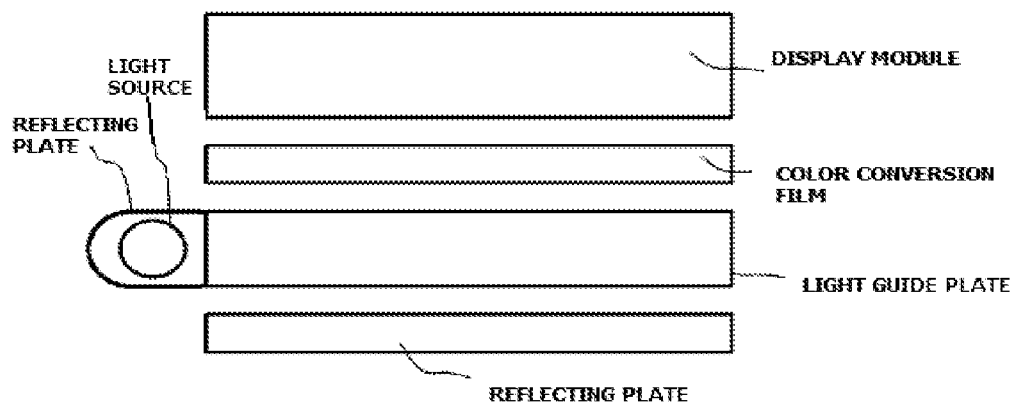

NITROGEN-CONTAINING CYCLIC COMPOUND AND COLOR CONVERSION FILM COMPRISING SAME

This application is a 35 U.S.C. § 371 National Stage of International Patent Application No. PCT/KR2019/004828, filed on Apr. 22, 2019, designating the United States, which claims priority to and the benefit of Korean Patent Application No. 10-2018-0054357 filed in the Korean Intellectual Property Office on May 11, 2018, the entire contents of which are incorporated herein by reference.

TECHNICAL FIELD

The present specification relates to a cyclic compound containing nitrogen, and a color conversion film, a backlight unit, and a display device, including the same.

BACKGROUND OF THE INVENTION

The existing light emitting diodes (LEDs) are obtained by mixing a green phosphor and a red phosphor with a blue light emitting diode or mixing a yellow phosphor and a blue-green phosphor with a UV light emission light emitting diode. However, in this method, it is difficult to control colors, and accordingly, the color rendition is not good. Therefore, the color gamut deteriorates.

In order to overcome the deterioration in the color gamut and reduce the production costs, methods of implementing green and red colors have been recently attempted by using a method of producing a quantum dot in the form of a film and combining the same with a blue LED. However, cadmium-based quantum dots have safety problems, and the other quantum dots have much lower efficiencies than those of the cadmium-based quantum dots. Further, quantum dots have low stability against oxygen and water, and have a disadvantage in that the performance thereof significantly deteriorates when the quantum dots are aggregated. In addition, when quantum dots are produced, it is difficult to constantly maintain the size thereof, and thus, the production cost is high.

BRIEF SUMMARY OF INVENTION

The present specification provides a cyclic compound containing nitrogen, and a color conversion film, a backlight unit, and a display device, including the same.

An exemplary embodiment of the present specification provides a compound represented by the following Formula 1.

[Formula 1]

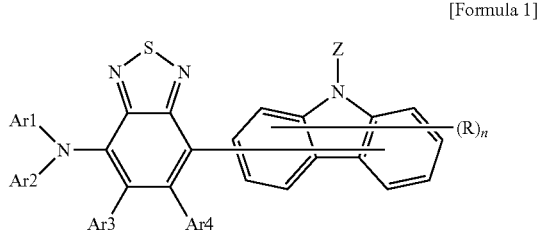

In Formula 1,

Ar1 and Ar2 are the same as or different from each other, and are each independently a substituted or unsubstituted aryl group, Ar3 and Ar4 are the same as or different from each other, and are each independently hydrogen, deuterium, or a halogen group, Z is a substituted or unsubstituted aryl group; or a substituted or unsubstituted heteroaryl group, R is hydrogen; deuterium; a halogen group; a cyano group; a nitro group; a carbonyl group; a carboxyl group (—COOH); an ether group; a hydroxyl group; a substituted or unsubstituted alkyl group; a substituted or unsubstituted aryl group; a substituted or unsubstituted alkoxy group; a substituted or unsubstituted aryloxy group; a substituted or unsubstituted alkenyl group; or —C(=O)ORa, or adjacent substituents may be bonded to each other to form a ring which is unsubstituted or substituted with a substituted or unsubstituted aryl group, and Ra is a substituted or unsubstituted alkyl group, and n is an integer from 0 to 7.

Another exemplary embodiment of the present specification provides a color conversion film including: a resin matrix; and the compound represented by Formula 1, which is dispersed in the resin matrix.

Still another exemplary embodiment of the present specification provides a backlight unit including the color conversion film.

Yet another exemplary embodiment of the present specification provides a display device including the backlight unit.

Advantageous Effects

A compound according to an exemplary embodiment of the present specification has better processability and heat resistance as a long-wavelength phosphor than a compound having a benzothiadiazole structure in the related art. Therefore, by using the compound described in the present specification as a fluorescent material of a red color conversion film, it is possible to provide a color conversion film which has excellent brightness and color gamut and excellent heat resistance.

DESCRIPTION OF DRAWINGS

FIG. 1 is a schematic view in which a color conversion film according to an exemplary embodiment of the present specification is applied to a backlight unit.

FIG. 2 is a schematic view exemplifying a structure of a display device according to an exemplary embodiment of the present specification.

MODE FOR INVENTION

Hereinafter, the present application will be described in more detail.

When one part "includes" one constituent element in the present specification, unless otherwise specifically described, this does not mean that another constituent element is excluded, but means that another constituent element may be further included.

When one member is disposed "on" another member in the present specification, this includes not only a case where the one member is brought into contact with another member, but also a case where still another member is present between the two members.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a cyano group; a nitro group, a sulfonyl group; a carboxyl group (—COOH); a fluoroalkyl group; a cycloalkyl group; an amine group; an alkyl group; an alkynyl group; an alkenyl group; an alkoxy group; a silyl group; an aryloxy group; an arylthio group; an arylalkyl group; an aryl group; and a heteroaryl group or being substituted with a substituent to which two or more substituents are linked among the substituents exemplified above, or having no substituent.

In the present specification, an example of a halogen group may be fluorine, chlorine, bromine or iodine.

In the present specification, a sulfonyl group is —SO$_2$R', and R' may be a substituted or unsubstituted alkyl group; or a substituted or unsubstituted aryl group, but is not limited thereto.

In the present specification, the alkyl group may be straight-chained or branched, and the number of carbon atoms thereof is not particularly limited, but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethylbutyl, pentyl, n-pentyl, isopentyl, neopentyl, tert-pentyl, hexyl, n-hexyl, 1-methylpentyl, 2-methylpentyl, 4-methyl-2-pentyl, 2,3-dimethylbutyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 2-methylpentyl, 4-methylhexyl, 5-methylhexyl, dodecane, undecane, and the like, but are not limited thereto.

In the present specification, a cycloalkyl group is not particularly limited, but has preferably 3 to 30 carbon atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight-chained, branched, or cyclic. The number of carbon atoms of the alkoxy group is not particularly limited, but is preferably 1 to 30. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the alkenyl group may be straight-chained or branched, and the number of carbon atoms thereof is not particularly limited, but is preferably 2 to 30. Specific examples thereof include ethenyl, vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, the alkynyl group may be straight-chained or branched, and the number of carbon atoms thereof is not particularly limited, but is preferably 2 to 30. Specific examples thereof include an alkynyl group such as ethynyl, propynyl, 2-methyl-2-propynyl, 2-butynyl, and 2-pentynyl, and the like, but are not limited thereto.

In the present specification, a fluoroalkyl group is not limited thereto, but has preferably 1 to 10 carbon atoms, and specific examples thereof include a trifluoromethyl group, a perfluoroethyl group, and the like, but are not limited thereto.

In the present specification, an amine group may be selected from the group consisting of —NH$_2$; a monoalkylamine group; a dialkylamine group; an N-alkylarylamine group; a monoarylamine group; a diarylamine group; an N-arylheteroarylamine group; an N-alkylheteroarylamine group, a monoheteroarylamine group, and a diheteroarylamine group, and the number of carbon atoms thereof is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a ditolylamine group, an N-biphenylamine group, an N-phenyltolylamine group, a triphenylamine group, an N-biphenylamine group, an N-phenylbiphenylamine group, an N-phenylnaphthylamine group, an N-biphenylnaphthylamine group, an N-naphthylfluorenylamine group, an N-phenylphenanthrenylamine group, an N-biphenylphenanthrenylamine group, an N-phenylfluorenylamine group, an N-phenylterphenylamine group, an N-phenanthrenylfluorenylamine group, an N-biphenylfluorenylamine group, and the like, but are not limited thereto.

In the present specification, specific examples of a silyl group include a trimethylsilyl group, a triethylsilyl group, a t-butyldimethylsilyl group, a vinyldimethylsilyl group, a tetraphenylsilyl group, a propyldimethylsilyl group, a triphenylsilyl group, a diphenylsilyl group, a phenylsilyl group, and the like, but are not limited thereto.

In the present specification, an aryl group is not particularly limited, but has preferably 6 to 30 carbon atoms, and the aryl group may be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a triphenyl group, a pyrenyl group, a phenylanthracene group, a perylenyl group, a chrysenyl group, a fluorenyl group, dihydroanthracene

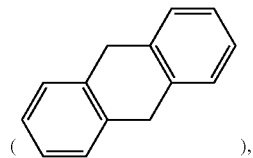

and the like, but are not limited thereto.

In the present specification, the fluorenyl group may be substituted, and adjacent substituents may be bonded to each other to form a ring.

When the fluorenyl group is substituted, the substituent may be

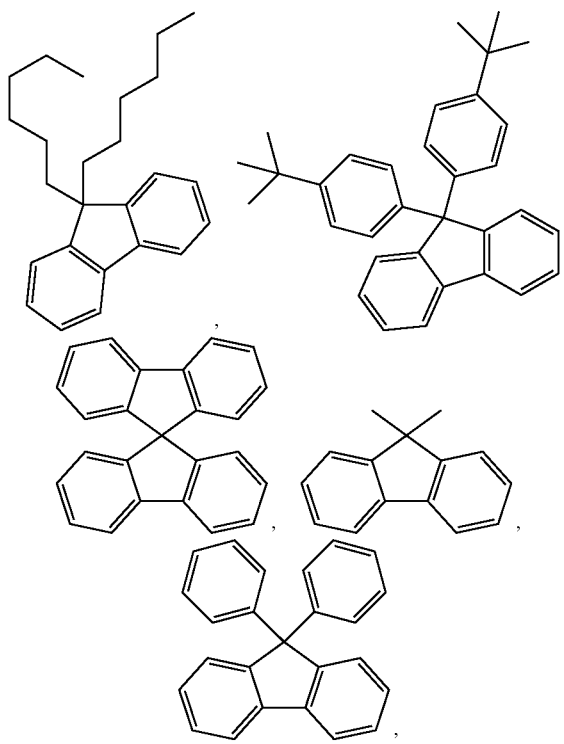

and the like. However, the substituent is not limited thereto.

In the present specification, the aryl group in the aryloxy group and the arylthio group is the same as the above-described examples of the aryl group. Specifically, examples of the aryloxy group include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group, and the like, and examples of the arylthio group include a phenylthioxy group, a 2-methylphenylthioxy group, a 4-tert-butylphenylthioxy group, and the like, but are not limited thereto.

In the present specification, the above-described description on the aryl group and the alkyl group may be applied to the aryl group and the alkyl group in the arylalkyl group.

In the present specification, a heteroaryl group includes one or more atoms other than carbon, that is, one or more heteroatoms, and specifically, the heteroatom may include one or more atoms selected from the group consisting of O, N, Se, S, and the like. The number of carbon atoms thereof is not particularly limited, but is preferably 2 to 30, and the heteroaryl group may be monocyclic or polycyclic. Examples of the heteroaryl group include a thiophene group, a furanyl group, a pyrrole group, an imidazolyl group, a thiazolyl group, an oxazolyl group, an oxadiazolyl group, a pyridine group, a bipyridyl group, a pyrimidine group, a triazinyl group, a triazolyl group, a benzotriazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group, a thiazolyl group, an isoxazolyl group, an oxadiazolyl group, a thiadiazolyl group, a benzothiazolyl group, a phenothiazinyl group, a dibenzofuranyl group, a xanthene group

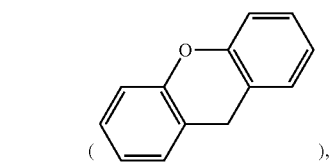

a phenoxathiine group

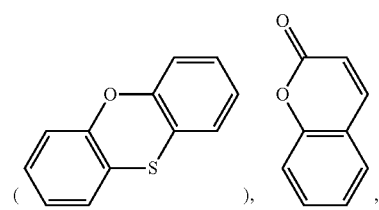

a dihydroacridine group

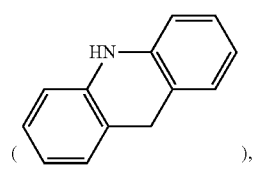 [SMILES: c1ccc2c(c1)Cc1ccccc1N2]

and the like, but are not limited thereto.

In the present specification, the heteroaryl group may be monocyclic or polycyclic, may be an aromatic ring, an aliphatic ring, or a fused ring of the aromatic ring and the aliphatic ring, and may be selected from the examples of the heteroaryl group.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the "adjacent groups are bonded to each other to form a ring" among the substituents means that a substituent is bonded to an adjacent group to form a substituted or unsubstituted hydrocarbon ring; or a substituted or unsubstituted hetero ring.

An exemplary embodiment of the present specification provides a compound represented by the following Formula 1.

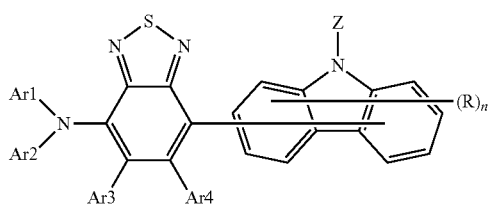

[Formula 1]

In Formula 1,

Ar1 and Ar2 are the same as or different from each other, and are each independently a substituted or unsubstituted aryl group, Ar3 and Ar4 are the same as or different from each other, and are each independently hydrogen, deuterium, or a halogen group, Z is a substituted or unsubstituted aryl group; or a substituted or unsubstituted heteroaryl group, R is hydrogen; deuterium; a halogen group; a cyano group; a nitro group; a carbonyl group; a carboxyl group (—COOH); an ether group; a hydroxyl group; a substituted or unsubstituted alkyl group; a substituted or unsubstituted aryl group; a substituted or unsubstituted alkoxy group; a substituted or unsubstituted aryloxy group; a substituted or unsubstituted alkenyl group; or —C(=O)ORa, or adjacent substituents may be bonded to each other to form a ring which is unsubstituted or substituted with a substituted or unsubstituted aryl group, and Ra is a substituted or unsubstituted alkyl group, and n is an integer from 0 to 7.

In an exemplary embodiment of the present specification, Ar1 and Ar2 are the same as or different from each other, and are each independently a substituted or unsubstituted aryl group having 6 to 30 carbon atoms.

In an exemplary embodiment of the present specification, Ar1 and Ar2 are the same as or different from each other, and are each independently an aryl group having 6 to 30 carbon atoms, which is unsubstituted or substituted with the following groups: a halogen group, a nitro group, a substituted or unsubstituted alkyl group, a substituted or unsubstituted alkenyl group, a substituted or unsubstituted alkynyl group, a substituted or unsubstituted silyl group, a substituted or unsubstituted alkoxy group, a substituted or unsubstituted aryloxy group, a substituted or unsubstituted amine group, a substituted or unsubstituted aryl group, or a substituted or unsubstituted heteroaryl group.

In an exemplary embodiment of the present specification, Ar1 and Ar2 are the same as or different from each other, and are each independently an aryl group having 6 to 30 carbons atoms, which is unsubstituted or substituted with the following groups: fluorine, a nitro group, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted silyl group, a substituted or unsubstituted alkoxy group having 1 to 30 carbon atoms, a substituted or unsubstituted aryloxy group, a substituted or unsubstituted amine group having 1 to 30 carbon atoms, a substituted or unsubstituted aryl group having 6 to 30 carbon atoms, or a substituted or unsubstituted heteroaryl group having 2 to 30 carbon atoms.

In an exemplary embodiment of the present specification, Ar1 and Ar2 are the same as or different from each other, and are each independently an aryl group having 6 to 30 carbon atoms, which is unsubstituted or substituted with the following groups: fluorine, a nitro group, an alkyl group having 1 to 30 carbon atoms, which is unsubstituted or substituted with an aryl group, an alkenyl group having 2 to 30 carbon atoms, which is substituted with a cyano group and an aryl group, an alkenyl group having 2 to 30 carbon atoms, which is substituted with an aryl group, an alkynyl group having 2 to 30 carbon atoms, which is substituted with an aryl group, a silyl group, an alkoxy group having 1 to 30 carbon atoms, which is unsubstituted or substituted with an alkyl group, an aryloxy group, an amine group having 1 to 30 carbon atoms, which is substituted with an alkyl group, an aryl group having 6 to 30 carbon atoms, or a heteroaryl group having 2 to 30 carbon atoms, which is unsubstituted or substituted with an aryl group.

In an exemplary embodiment of the present specification, Ar1 and Ar2 are the same as or different from each other, and are each independently an aryl group having 6 to 30 carbon atoms, which is unsubstituted or substituted with the following groups: fluorine, a nitro group, a methyl group, a propyl group, a butyl group, a neopentyl group which is substituted with an aryl group, a heptyl group, an ethenyl group which is substituted with a cyano group and an aryl group, an ethenyl group which is substituted with an aryl group, an ethynyl group which is substituted with an aryl group, a triphenylsilyl group, a methoxy group which is unsubstituted or substituted with an alkyl group, a phenoxy group, an N-biphenylamine group which is substituted with an alkyl group, a fluorenyl group, a naphthyl group, a terphenyl group, a pyrenyl group, a dibenzofuranyl group, a triazolyl group which is substituted with an aryl group, a benzoxazolyl group, or

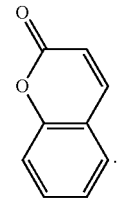

In an exemplary embodiment of the present specification, Ar3 and Ar4 are the same as or different from each other, and are each independently hydrogen, deuterium, or a halogen group.

In an exemplary embodiment of the present specification, Ar3 and Ar4 are the same as or different from each other, and are each independently hydrogen, deuterium, fluorine, chlorine, bromine, or iodine.

In an exemplary embodiment of the present specification, Ar3 and Ar4 are the same as or different from each other, and are each independently hydrogen, deuterium, fluorine, or chlorine.

In an exemplary embodiment of the present specification, Z is a substituted or unsubstituted aryl group having 6 to 30 carbon atoms; or a substituted or unsubstituted heteroaryl group having 2 to 30 carbon atoms.

In an exemplary embodiment of the present specification, Z is an aryl group having 6 to 30 carbon atoms, which is unsubstituted or substituted with one or more selected from the group consisting of a halogen group, a cyano group, a silyl group, a carboxyl group (COOH), a substituted or unsubstituted alkyl group, a substituted or unsubstituted alkenyl group, a substituted or unsubstituted alkoxy group, a substituted or unsubstituted cycloalkyl group, a substituted or unsubstituted sulfonyl group, a substituted or unsubstituted arylalkyl group, a substituted or unsubstituted arylthio group, a substituted or unsubstituted aryloxy group, and a substituted or unsubstituted aryl group; or a heteroaryl group having 2 to 30 carbon atoms, which is unsubstituted or substituted with one or more selected from an alkyl group and an aryl group.

In an exemplary embodiment of the present specification, Z is an aryl group having 6 to 30 carbon atoms, which is unsubstituted or substituted with one or more selected from the group consisting of a halogen group, a cyano group, a silyl group, a carboxyl group (COOH), an alkyl group which is unsubstituted or substituted with an aryl group, an alkenyl group which is substituted with a cyano group and an aryl group, an alkoxy group which is substituted with an alkyl group or an aryloxy group, a cycloalkyl group, a sulfonyl group which is substituted with an aryl group, an arylalkyl group, an arylthio group which is substituted with an alkyl group, an aryloxy group, and an aryl group; or a heteroaryl group having 2 to 30 carbon atoms, which is unsubstituted or substituted with one or more selected from an alkyl group and an aryl group.

In an exemplary embodiment of the present specification, Z is an aryl group having 6 to 30 carbon atoms, which is unsubstituted or substituted with one or more selected from the group consisting of a halogen group, a cyano group, a silyl group, a carboxyl group (COOH), neopentyl group which is substituted with an aryl group, a propyl group which is substituted with an aryl group, an ethenyl group which is substituted with a cyano group and an aryl group, a methoxy group which is substituted with an alkyl group, an ethoxy group which is substituted with an aryloxy group, a cyclohexyl group, a sulfonyl group which is substituted with a phenyl group, an arylalkyl group, an arylthio group which is substituted with an alkyl group, a phenoxy group, a phenyl group, a naphthyl group, and a phenylanthracene group; a dihydroanthracene group which is substituted with an alkyl group; a pyridine group; a xanthene group which is substituted with an alkyl group; a dihydroacridine group which is substituted with an alkyl group and an aryl group; a phenoxathiine group; or a dibenzofuranyl group which is unsubstituted or substituted with an aryl group.

In the present specification, $(R)_n$ means that n substituents represented by R is substituted with the carbazole group of Formula 1, and n is an integer from 0 to 7.

In an exemplary embodiment of the present specification, R is hydrogen; deuterium; a halogen group; a cyano group; a substituted or unsubstituted alkyl group; a substituted or unsubstituted aryl group; a substituted or unsubstituted alkoxy group; a substituted or unsubstituted aryloxy group; or —C(=O)ORa, or adjacent substituents may be bonded to each other to form a ring which is unsubstituted or substituted with a substituted or unsubstituted aryl group, and Ra is a substituted or unsubstituted alkyl group.

In an exemplary embodiment of the present specification, R is hydrogen; deuterium; a halogen group; a cyano group; a substituted or unsubstituted alkyl group having 1 to 50 carbon atoms; a substituted or unsubstituted alkoxy group having 1 to 30 carbon atoms; an aryloxy group which is substituted with an alkyl group; a substituted or unsubstituted aryl group having 6 to 30 carbon atoms; or —C(=O)ORa, or adjacent substituents may be bonded to each other to form a ring having 3 to 30 carbon atoms, which is unsubstituted or substituted with a substituted or unsubstituted aryl group, and Ra is a substituted or unsubstituted alkyl group.

In an exemplary embodiment of the present specification, R is hydrogen; deuterium; a halogen group; a cyano group; an alkyl group having 1 to 50 carbon atoms; an alkoxy group having 1 to 30 carbon atoms, which is substituted with a heteroaryl group; an aryl group having 6 to 30 carbon atoms, which is unsubstituted or substituted with a halogen group, an alkyl group substituted with an aryl group, or a fluoroalkyl group; or —C(=O)ORa, or adjacent substituents may be bonded to each other to form a ring having 3 to 30 carbon atoms, which is unsubstituted or substituted with an aryl group which is unsubstituted or substituted with an alkyl group or a substituted or unsubstituted alkenyl group a dihydroanthracene group substituted with an alkyl group, and Ra is an alkyl group which is unsubstituted or substituted with an aryl group.

In an exemplary embodiment of the present specification, R is hydrogen; deuterium; chlorine; a cyano group; dodecane; an ethoxy group which is substituted with a heteroaryl group; a phenyl group which is unsubstituted or substituted with fluorine, a propyl group substituted with an aryl group, or a fluoroalkyl group; or —C(=O)ORa, or adjacent substituents may be bonded to each other to form a ring having 3 to 30 carbon atoms, which is unsubstituted or substituted with a fluorenyl group; a phenyl group which is unsubstituted or substituted with an alkyl group or an alkenyl group substituted with a cyano group and an aryl group; or a dihydroanthracene group substituted with an alkyl group, and Ra is an ethyl group which is unsubstituted or substituted with an aryl group.

In an exemplary embodiment of the present specification, Formula 1 is represented by the following Formula 2 or 3.

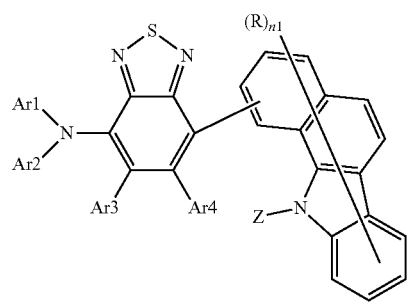

[Formula 2]

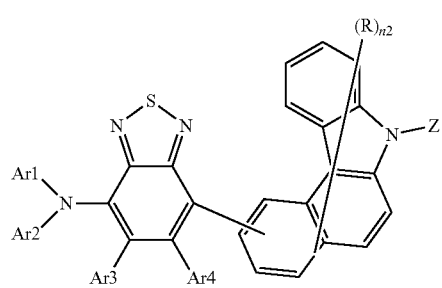

[Formula 3]

In Formulae 2 and 3, Ar1 to Ar4, R, and Z are the same as the above-described definitions in Formula 1.

In Formulae 2 and 3, n1 and n2 are an integer from 0 to 9.

In an exemplary embodiment of the present specification, Formula 1 is represented by the following structural formulae.

11
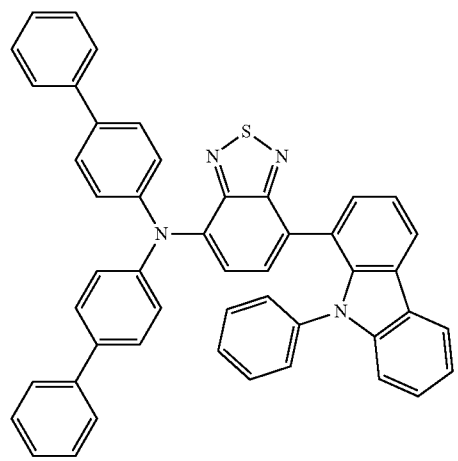
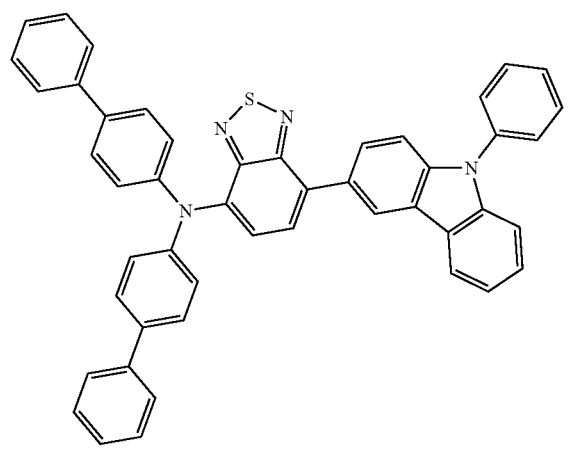
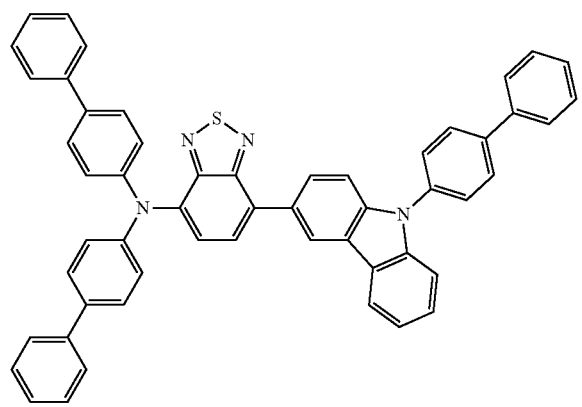
12
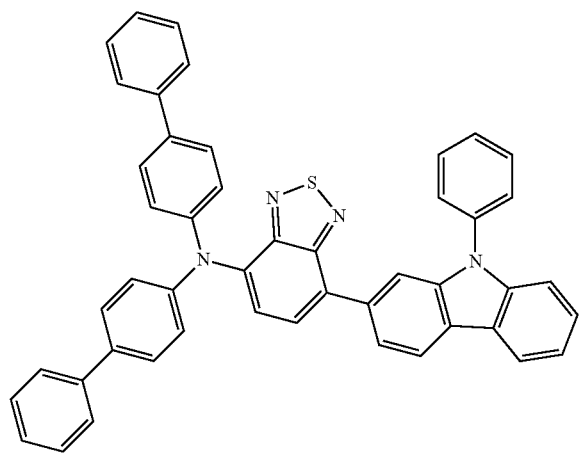
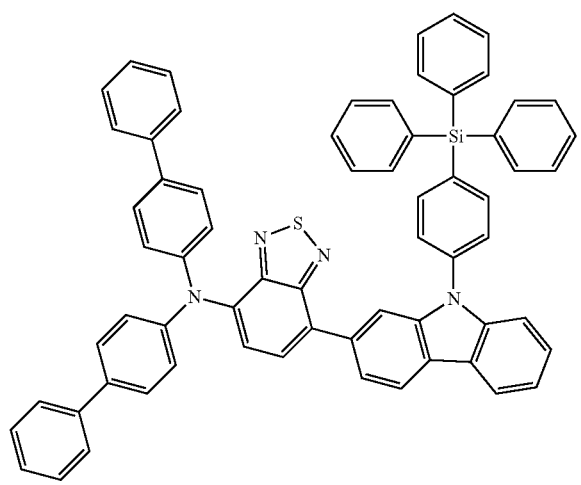
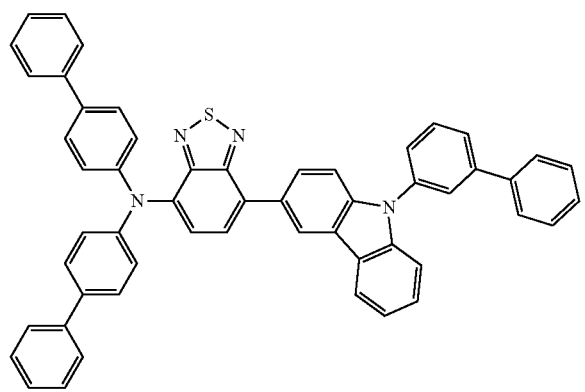

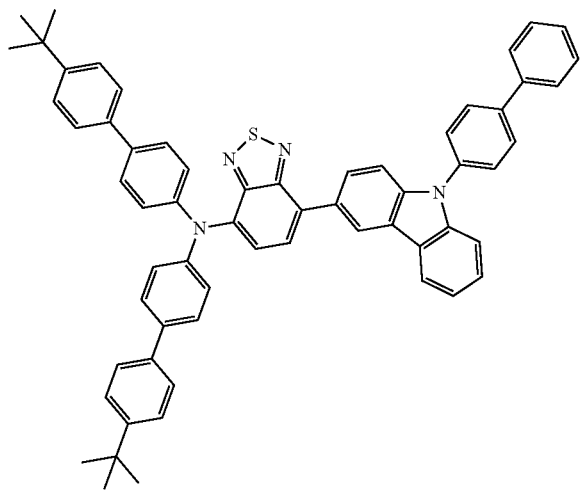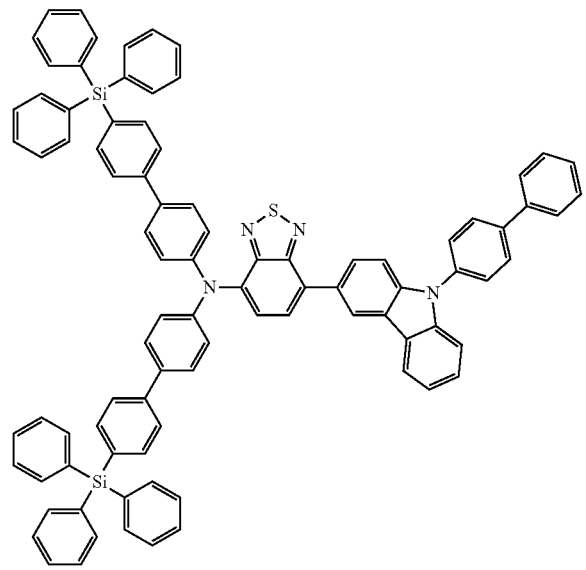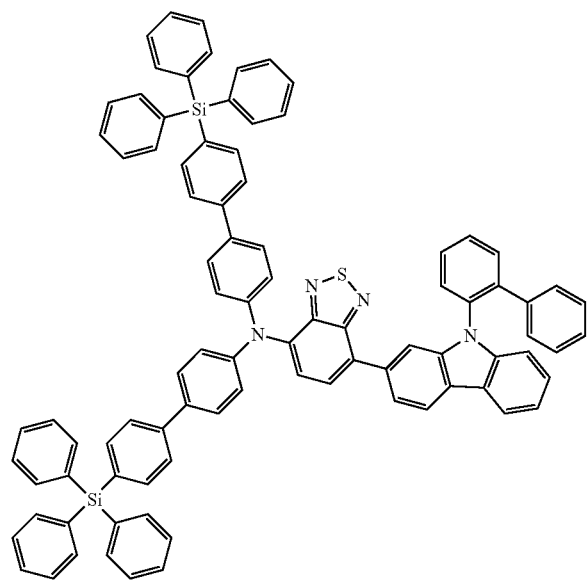

-continued
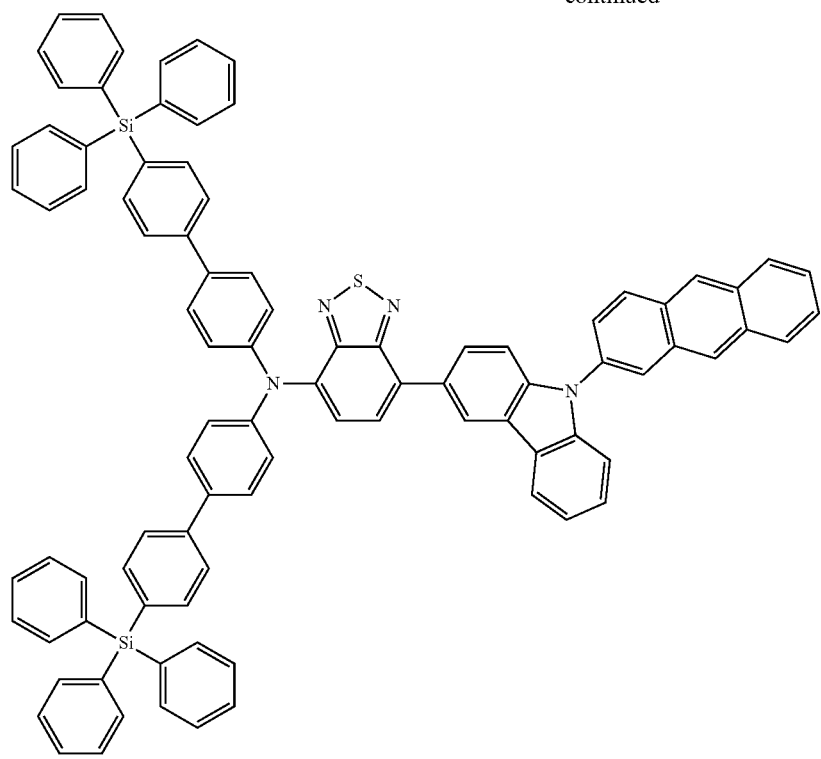
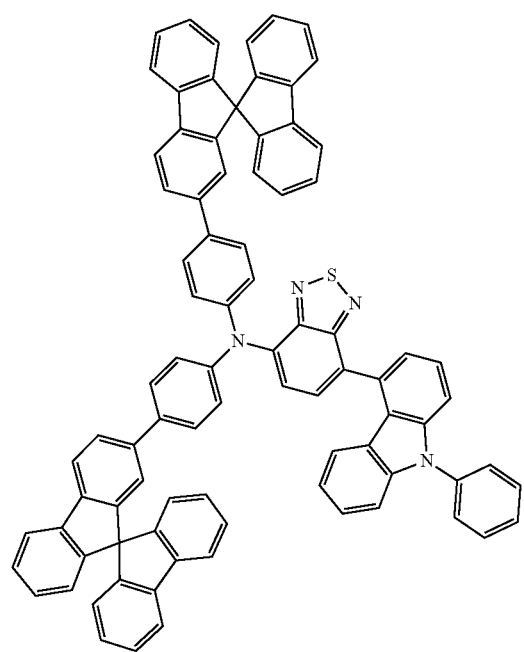

-continued
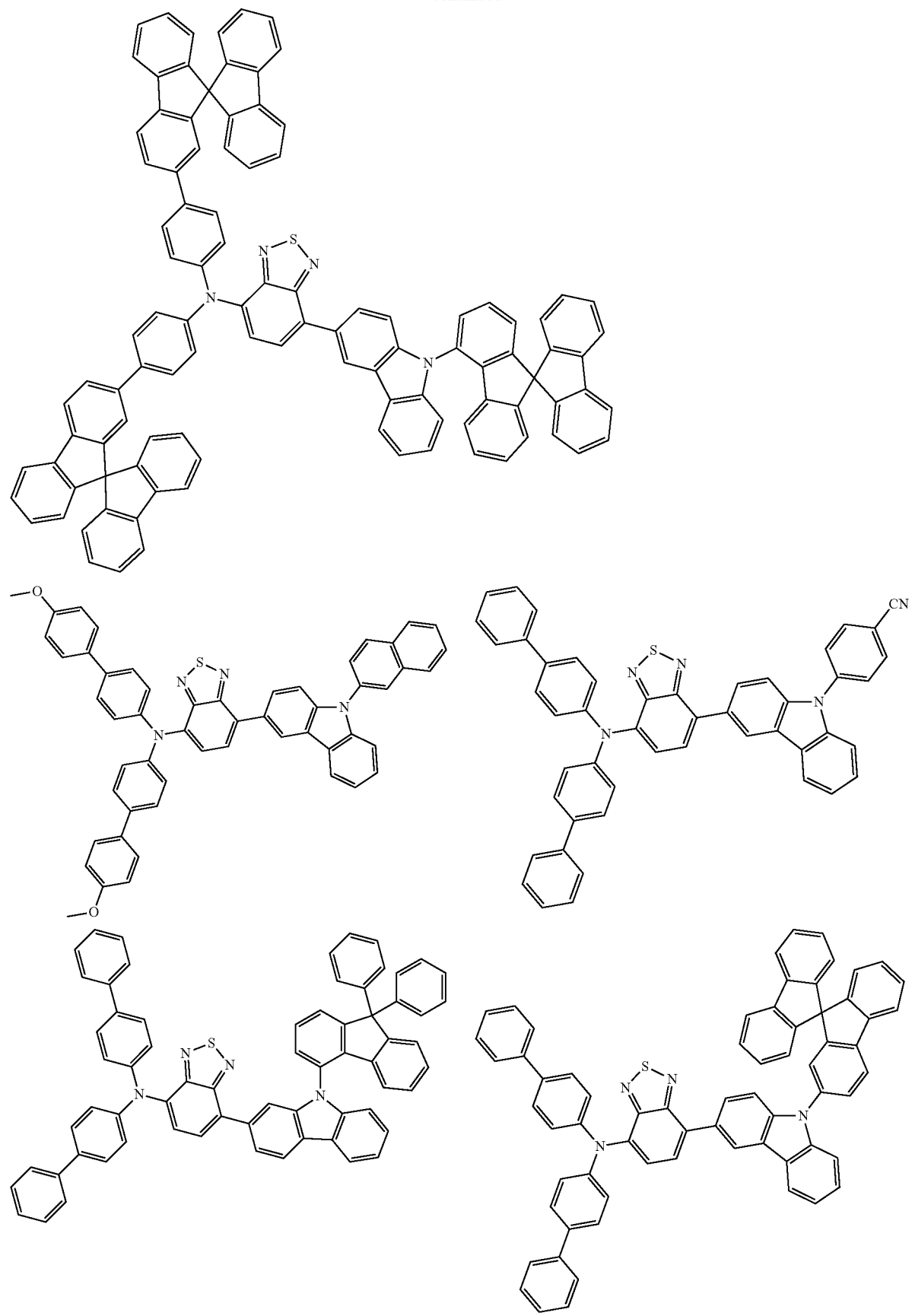

-continued
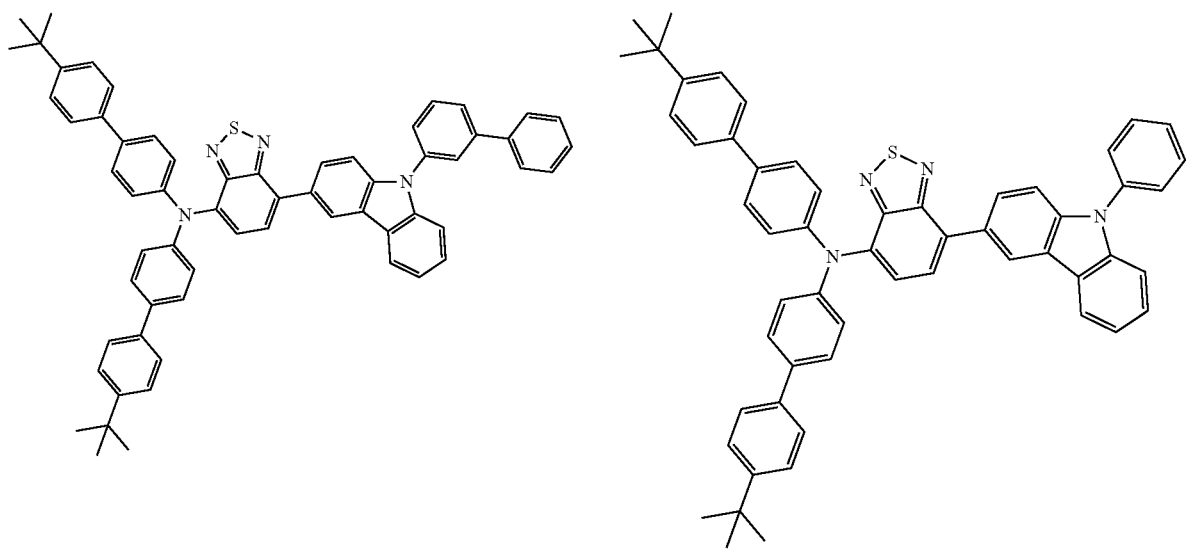
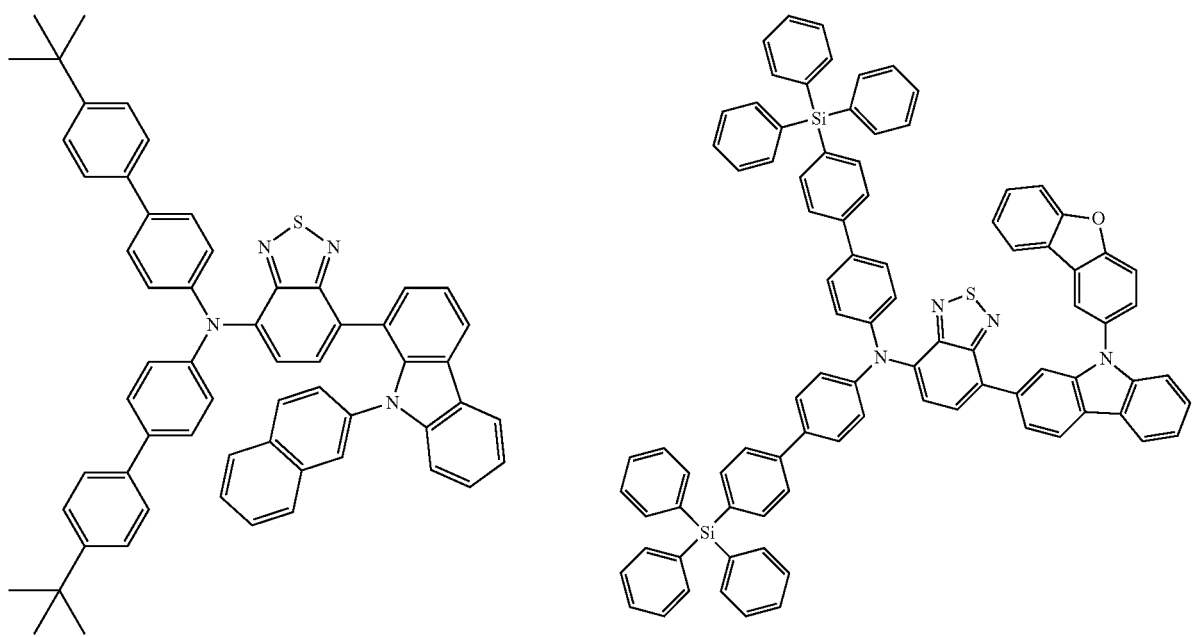

-continued
21
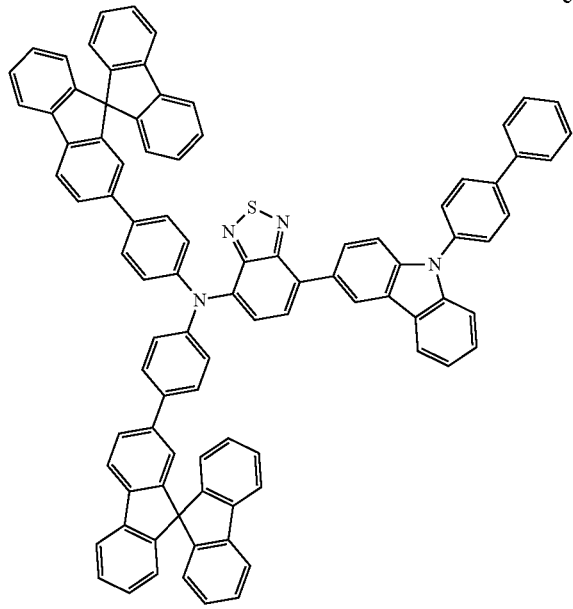
22
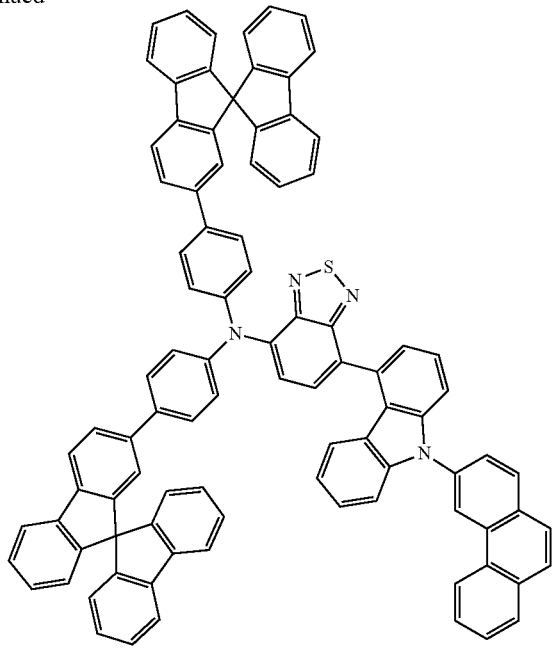
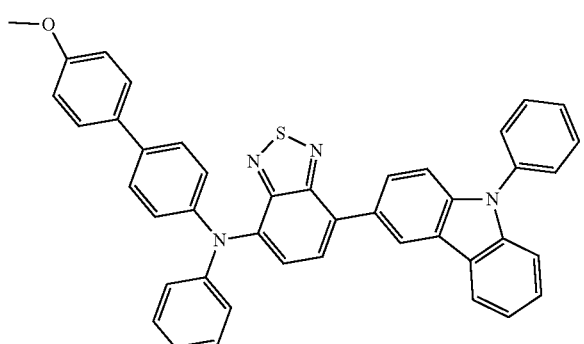
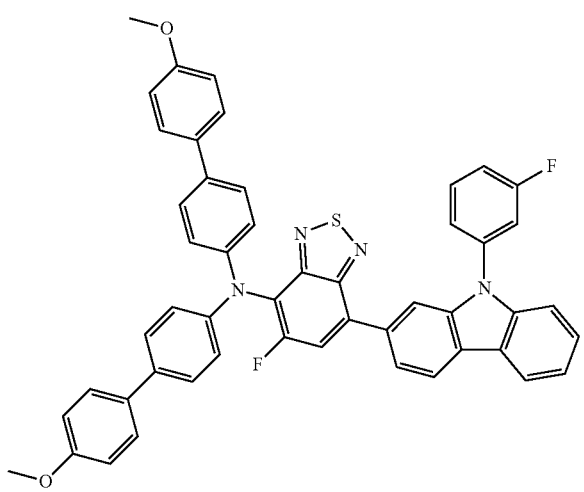
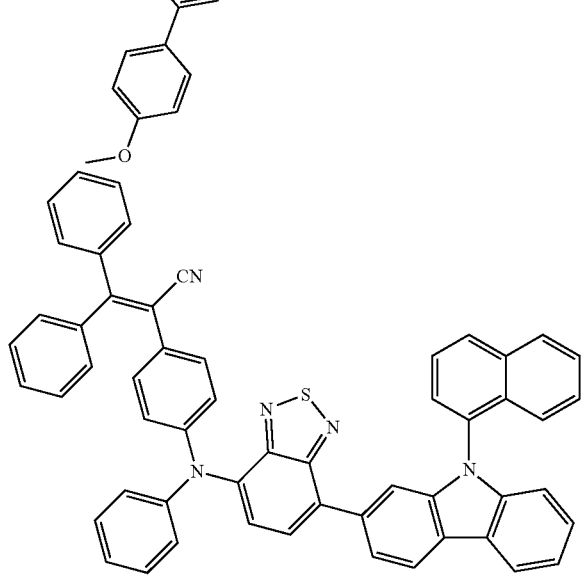
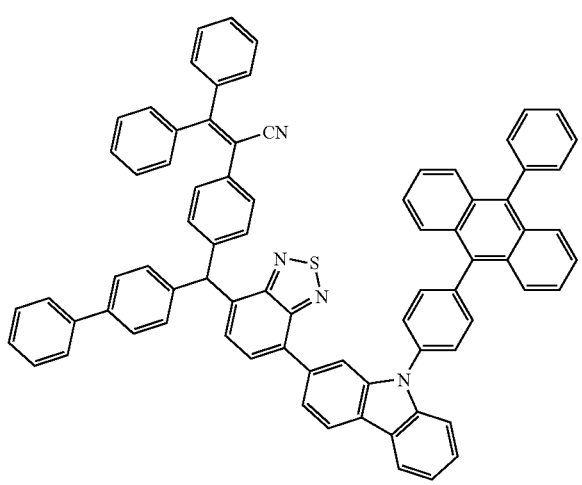

-continued
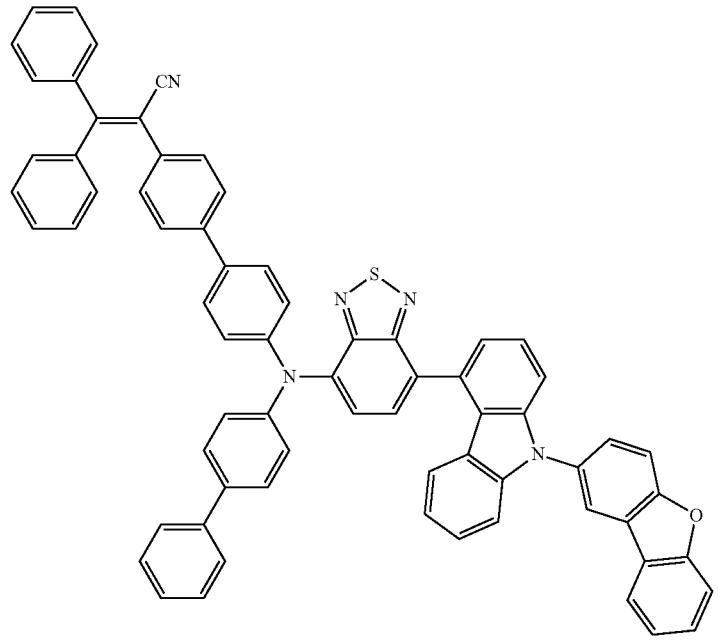
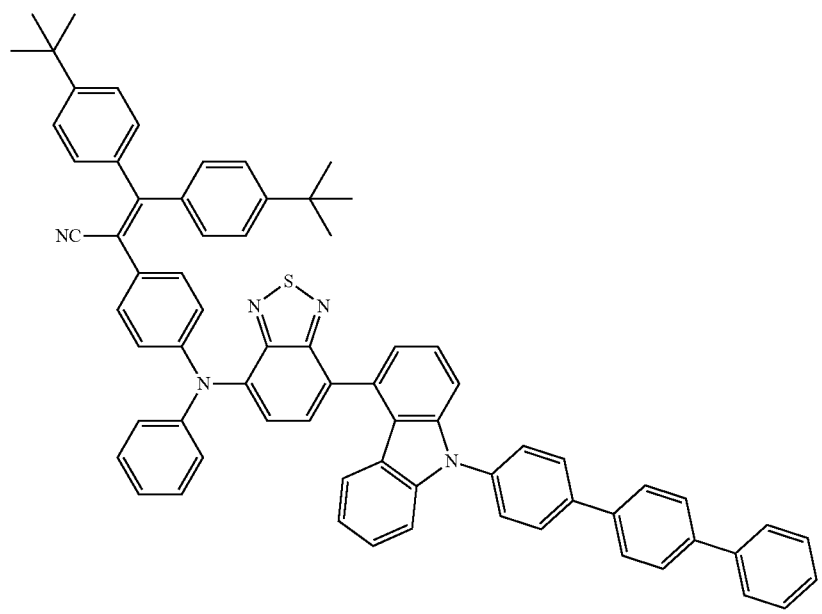

-continued
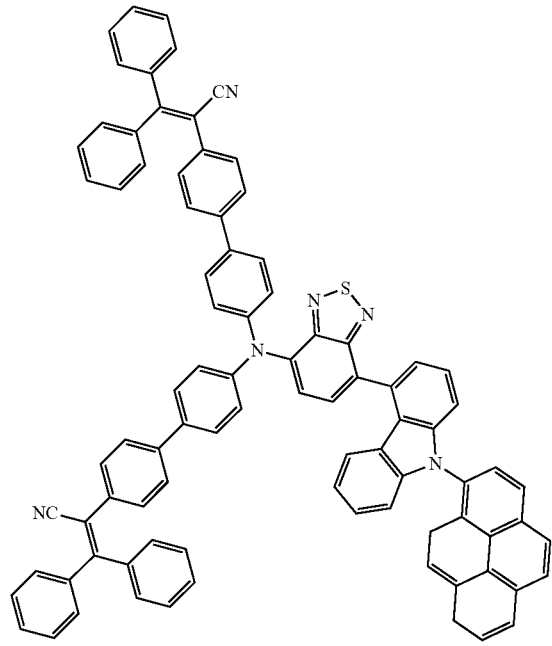
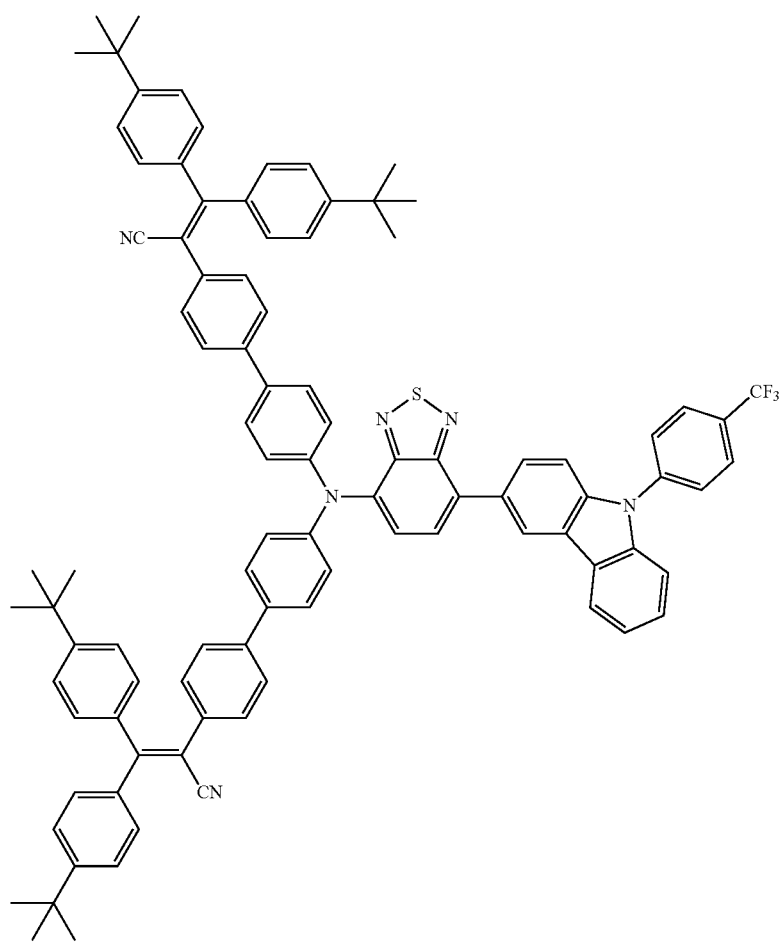

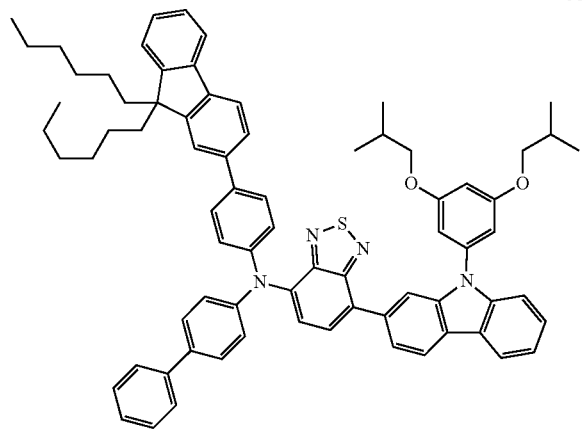
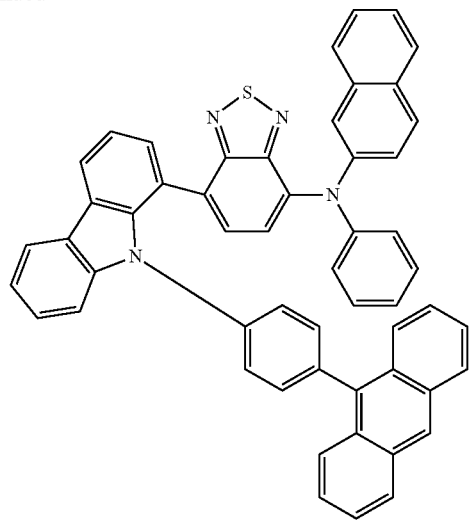
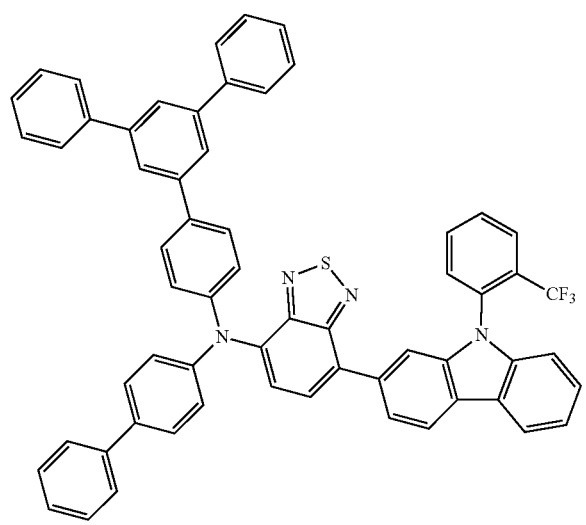
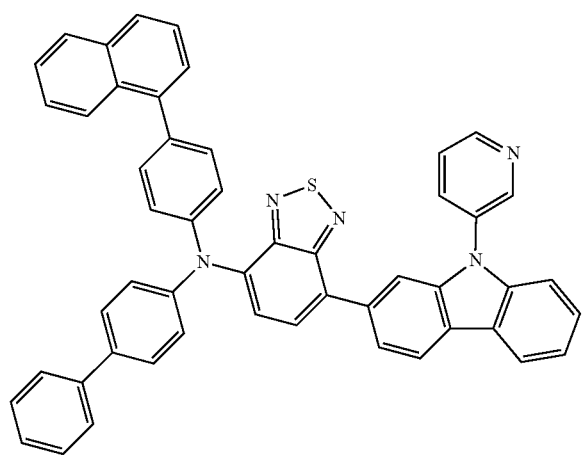
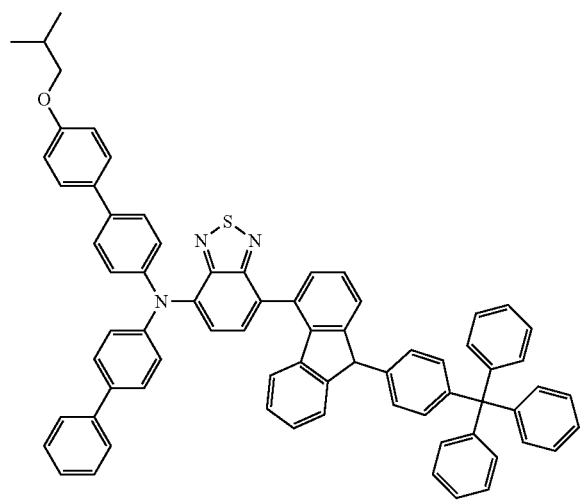
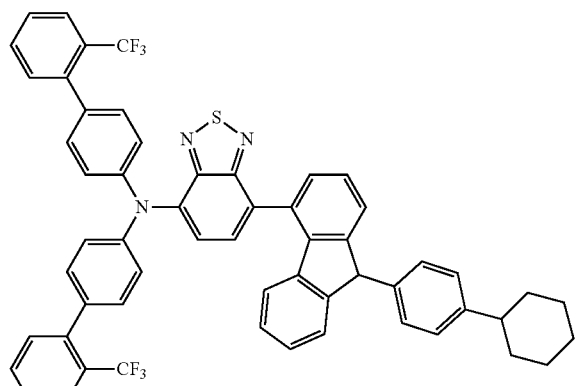

-continued
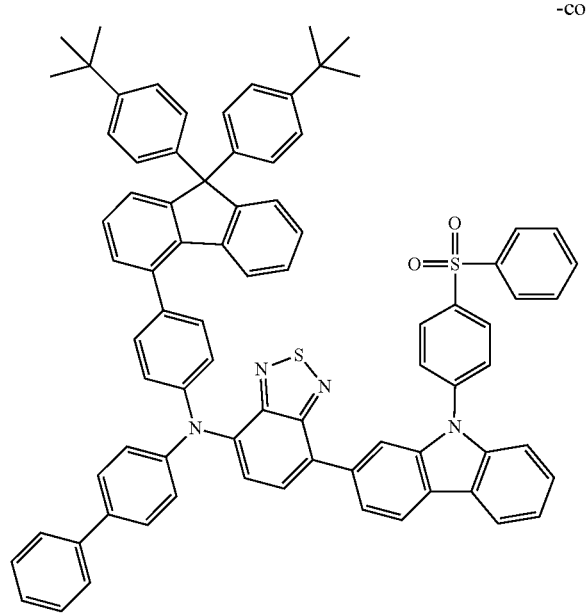
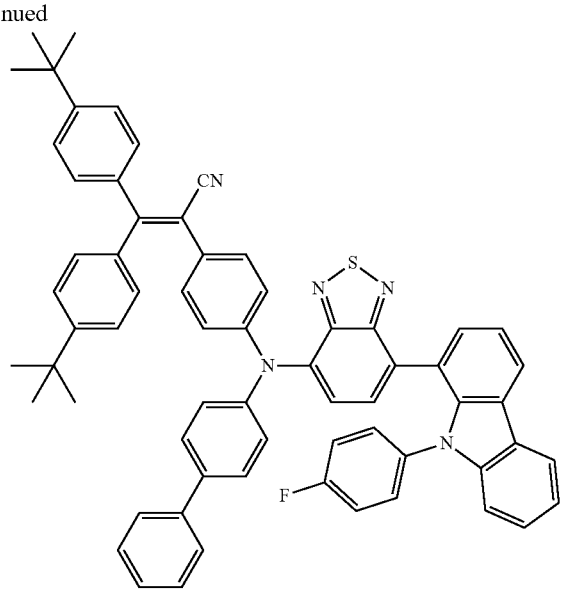
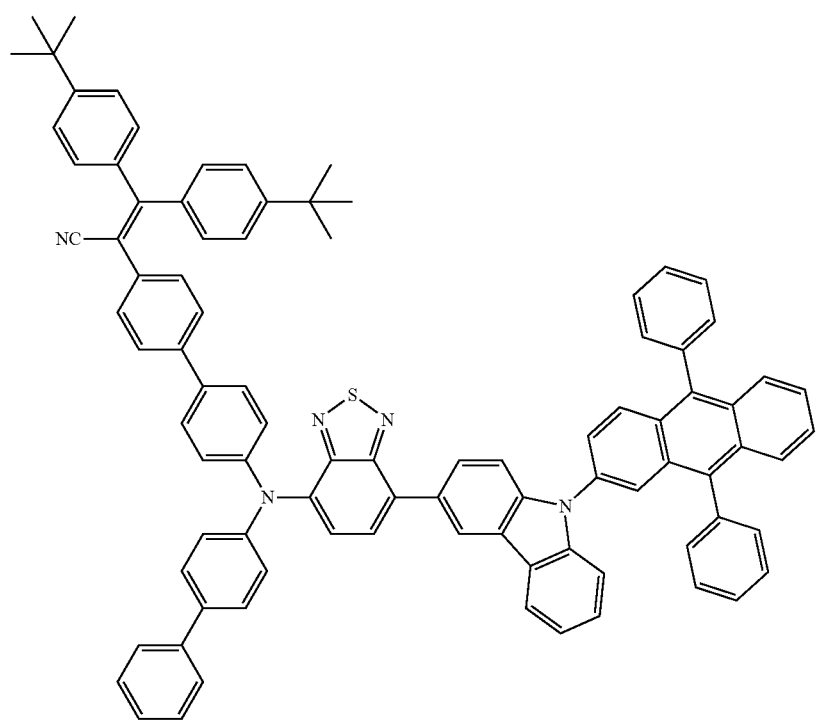

31
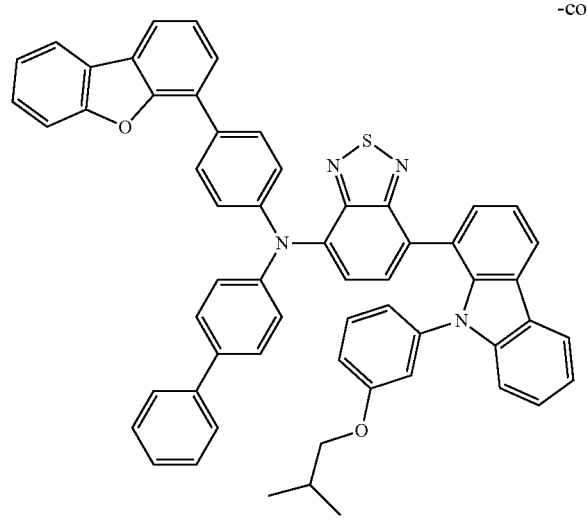
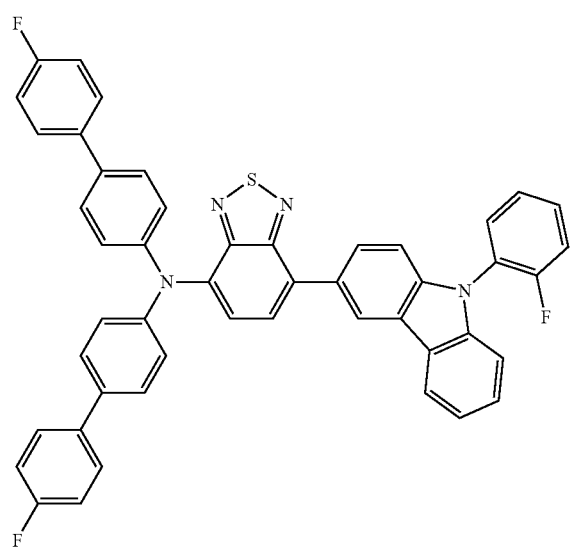
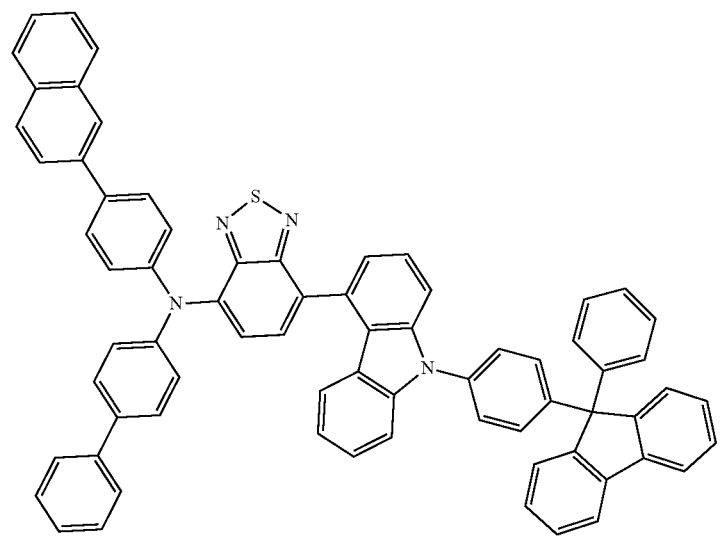
32
-continued
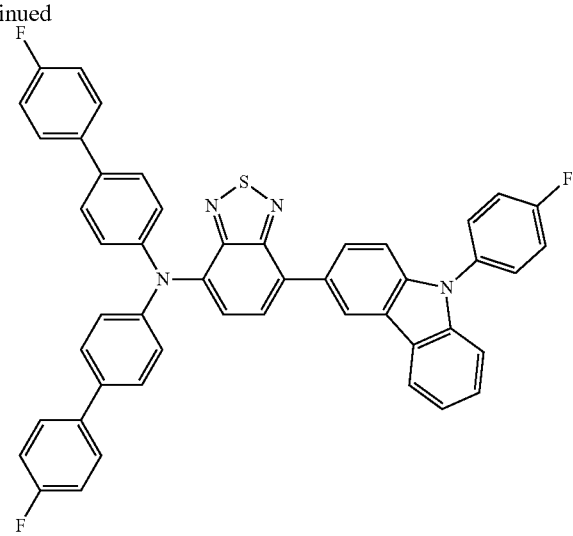
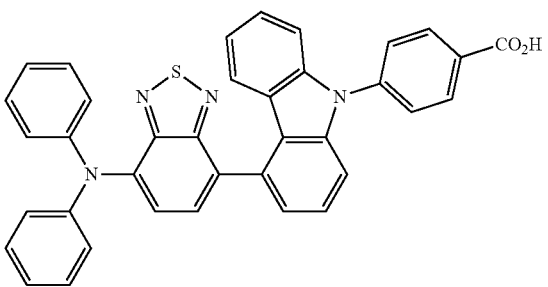

-continued
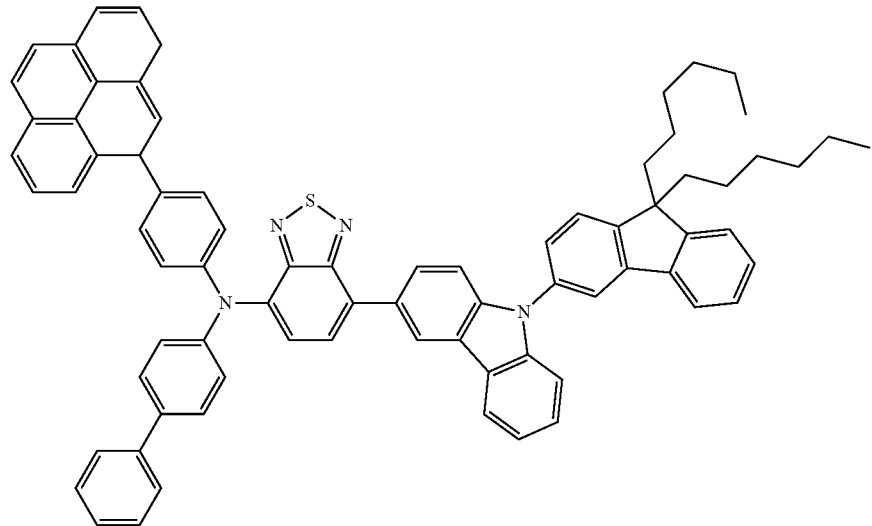
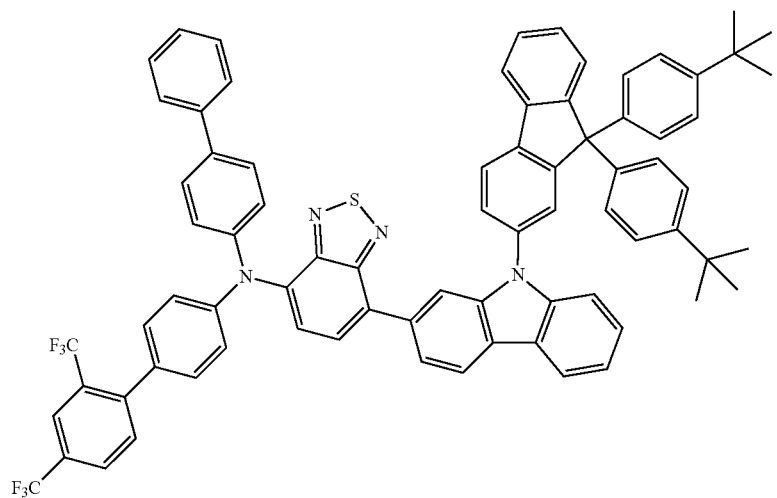
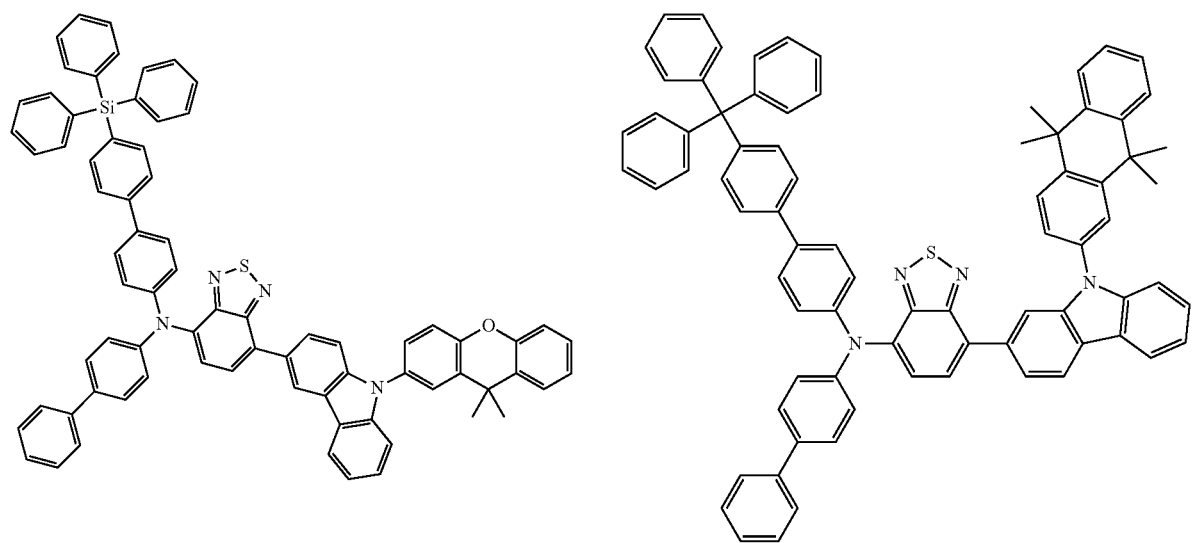

-continued
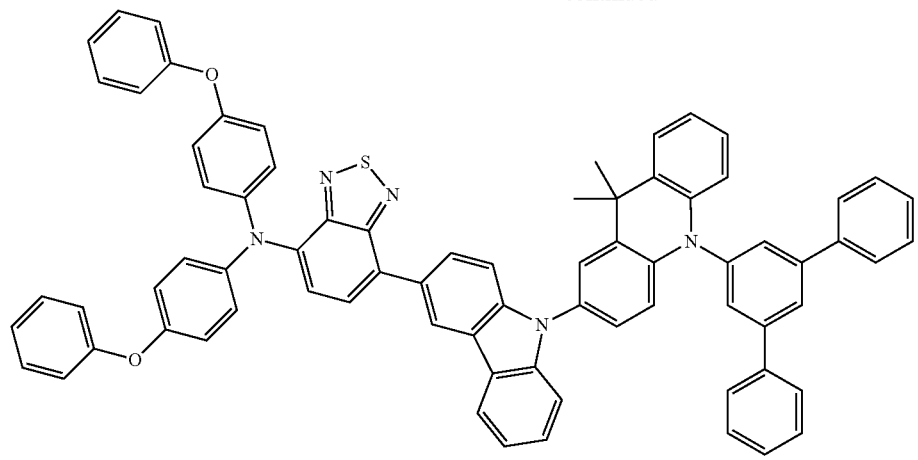
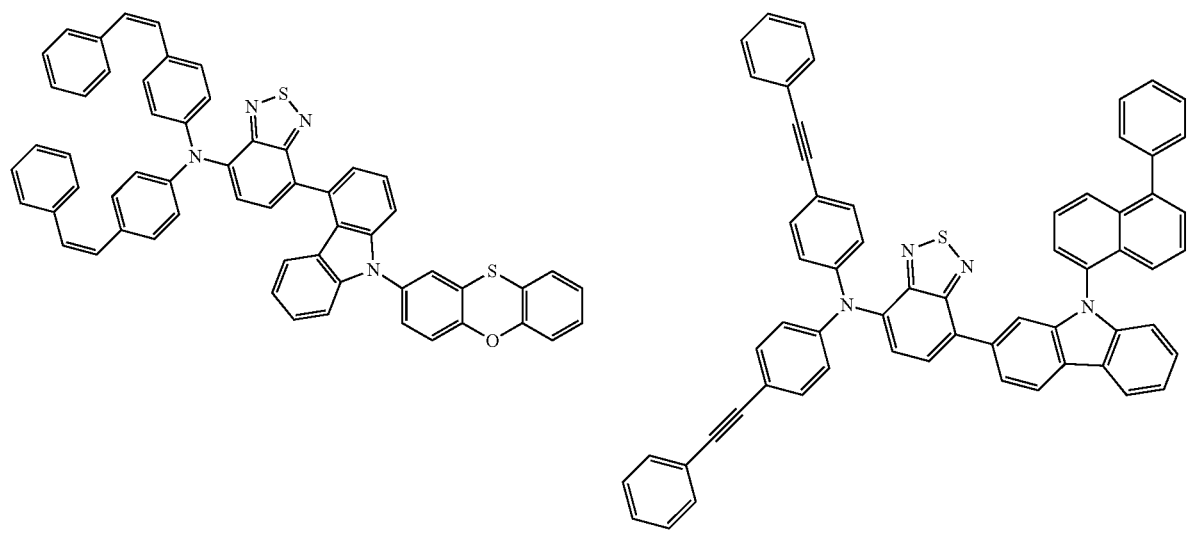
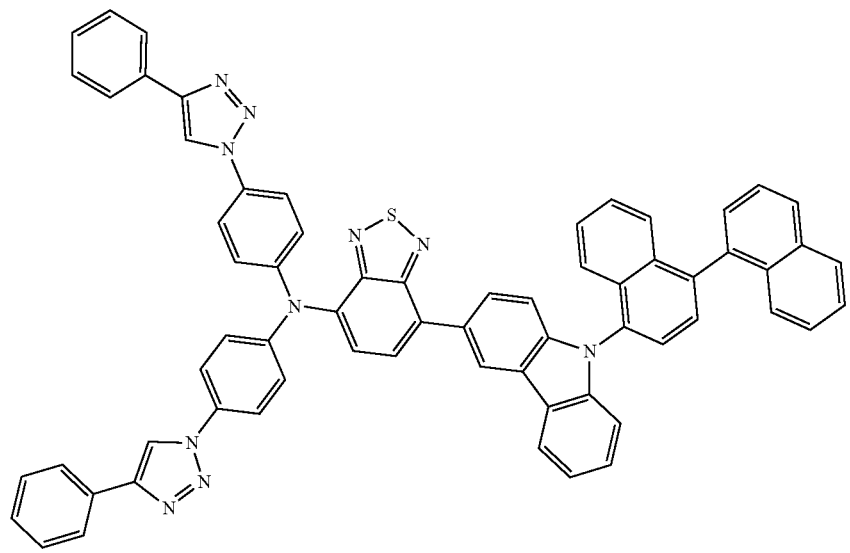

-continued
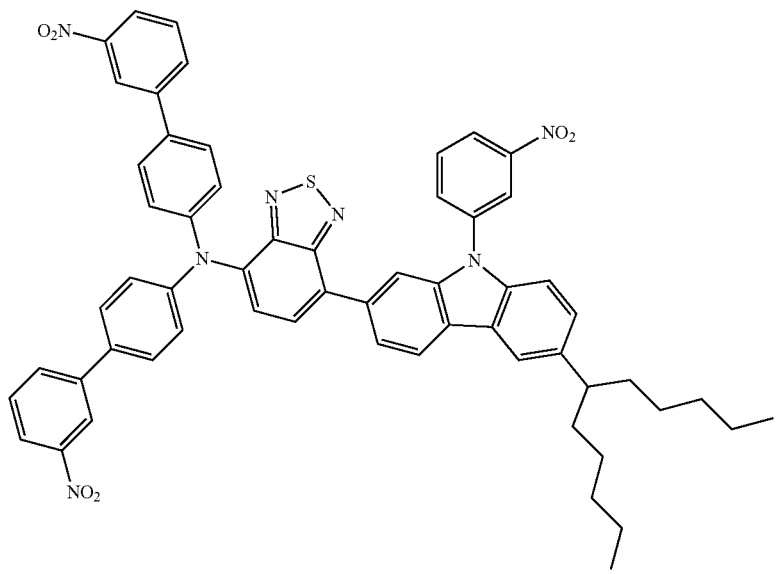
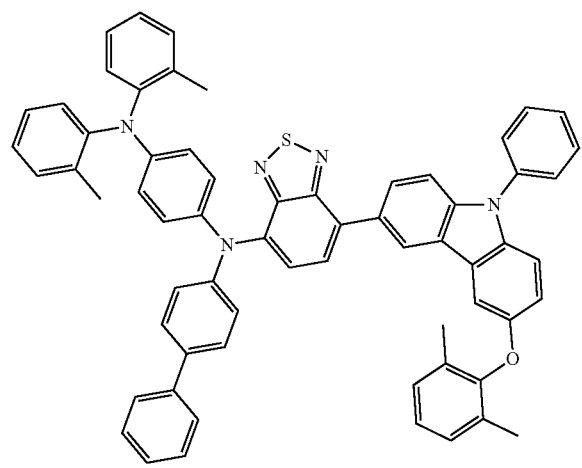

-continued
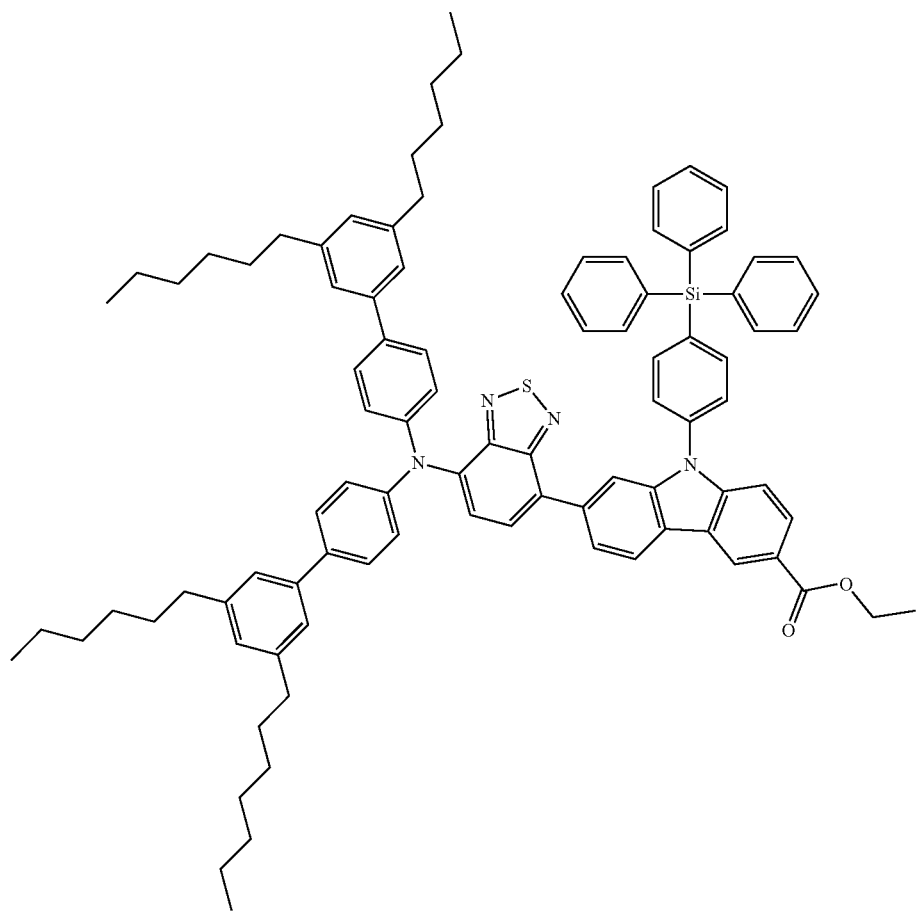
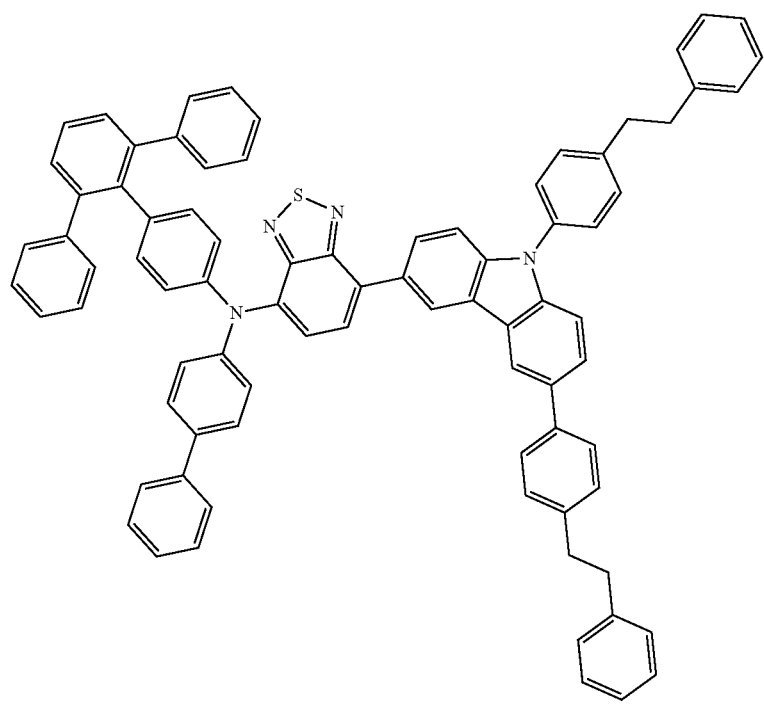

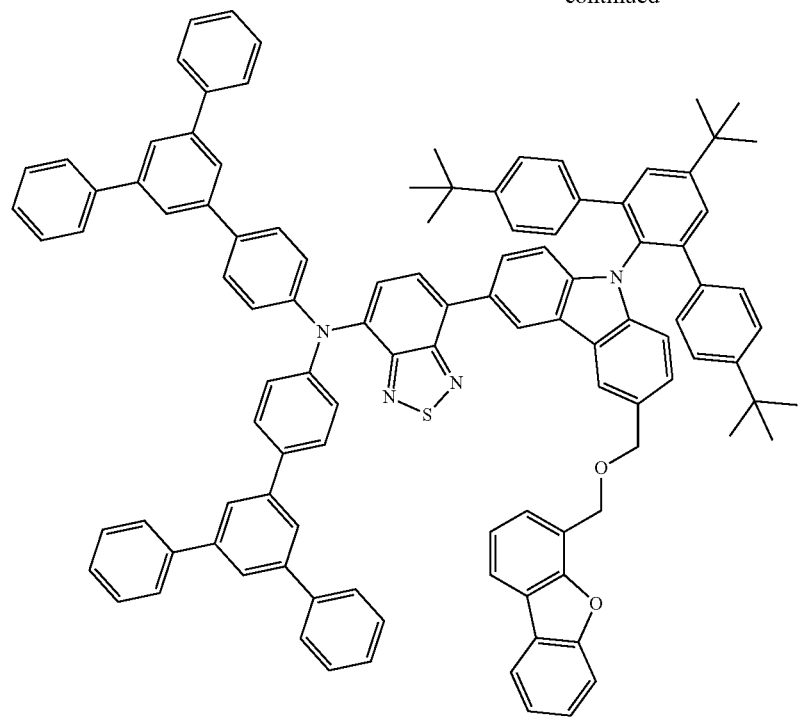
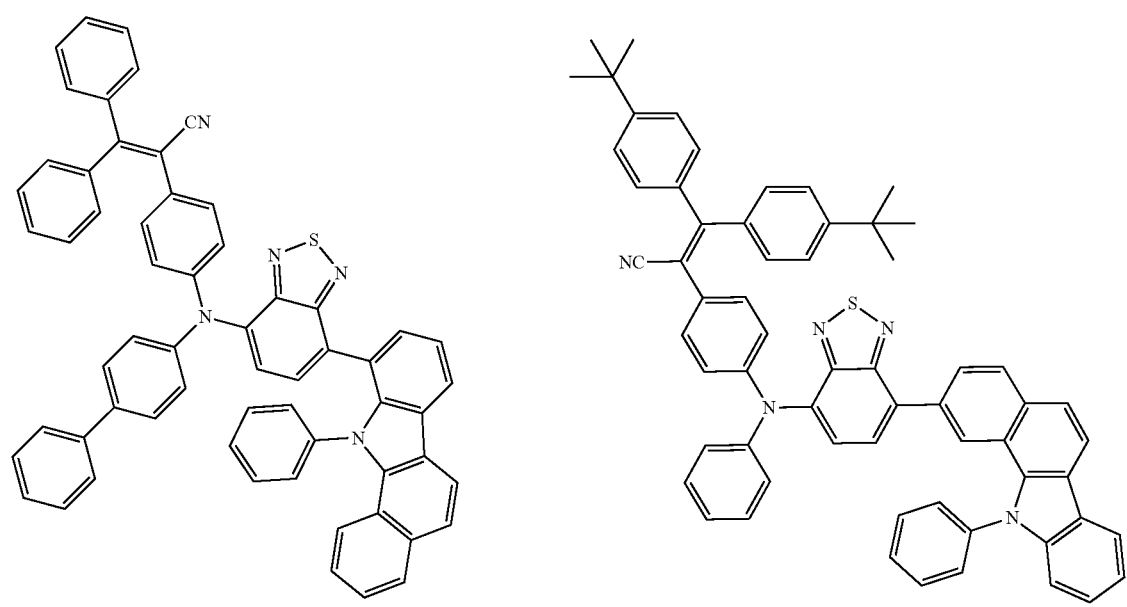

-continued
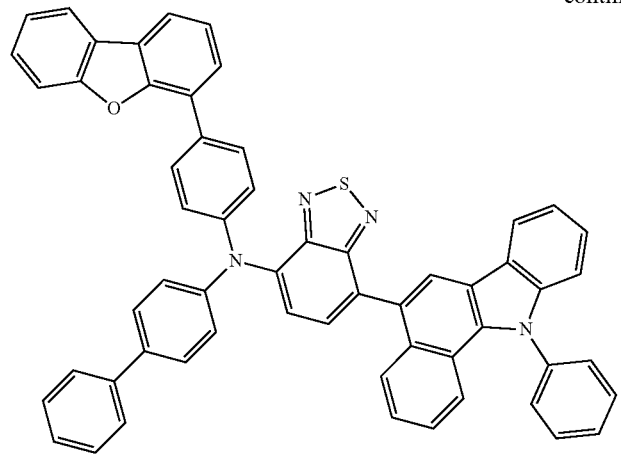
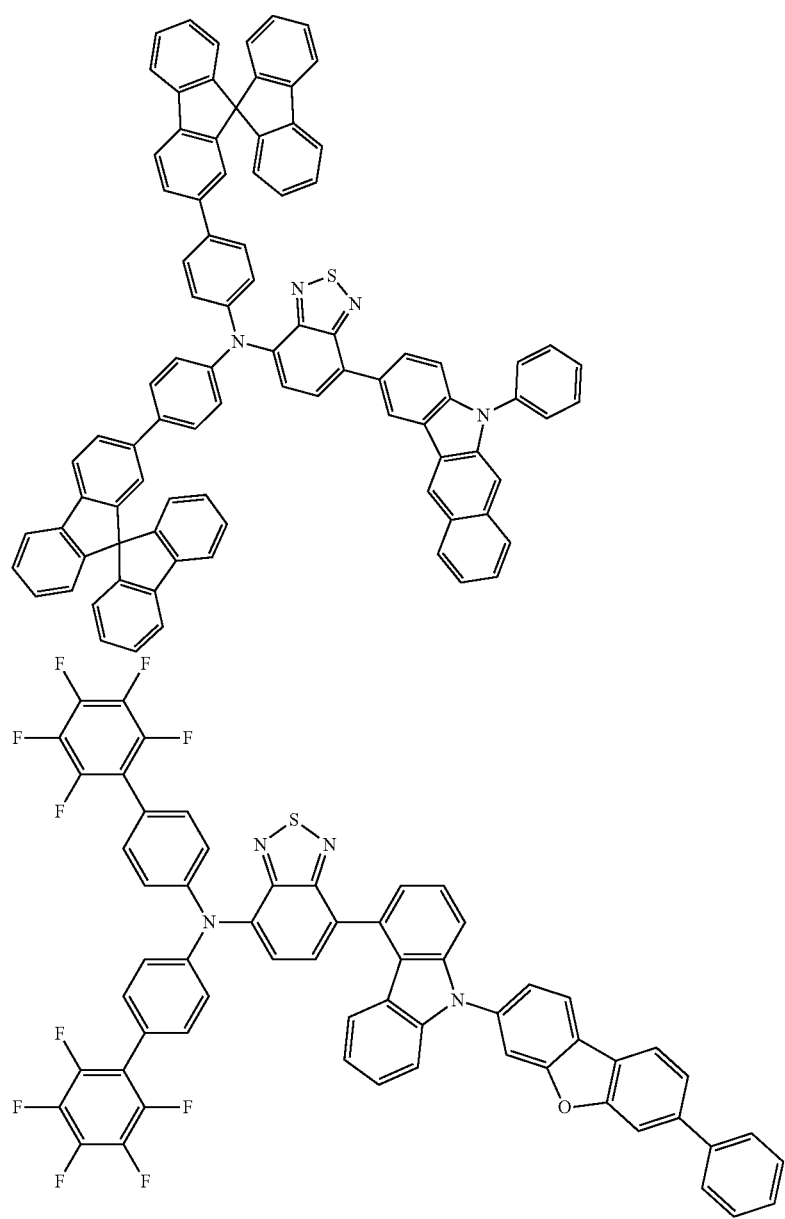

45
46
-continued
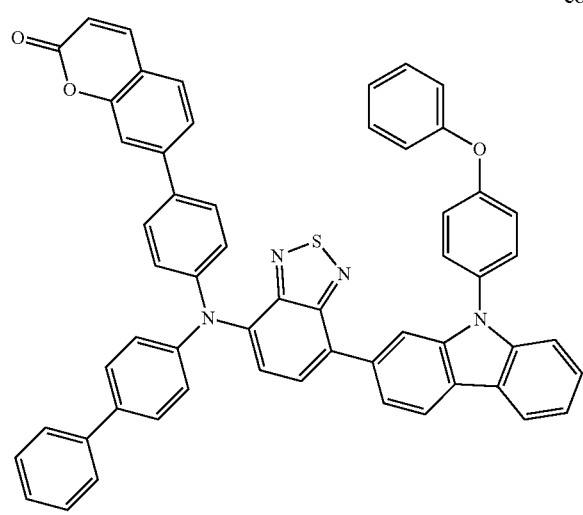
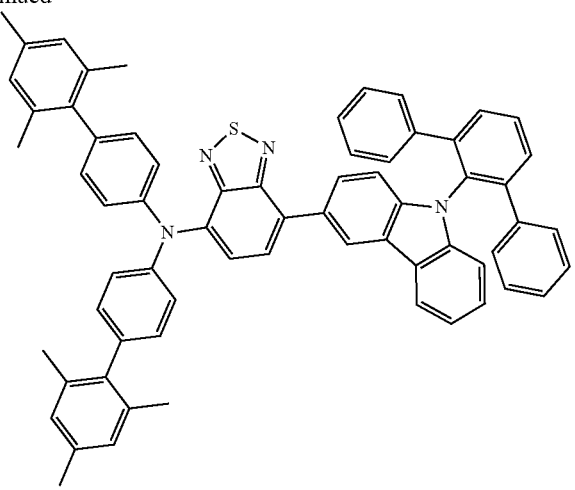
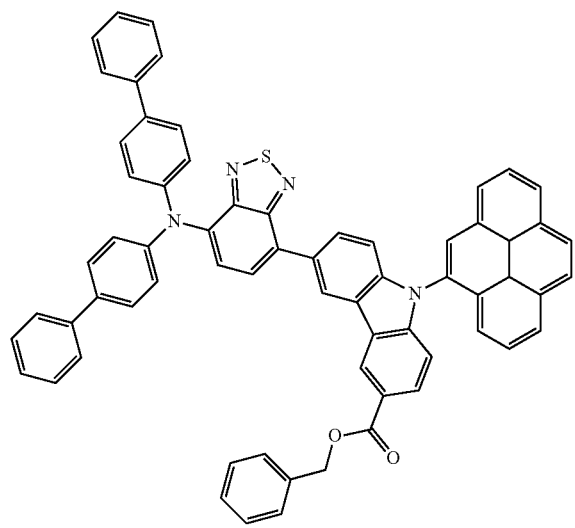
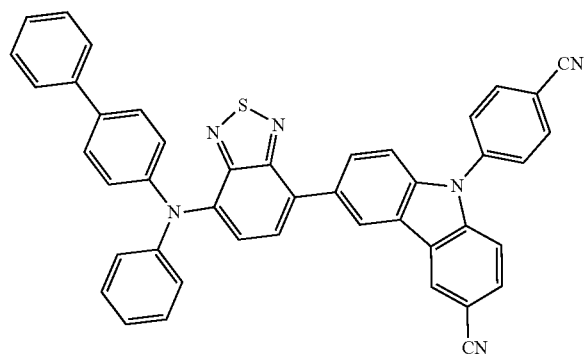
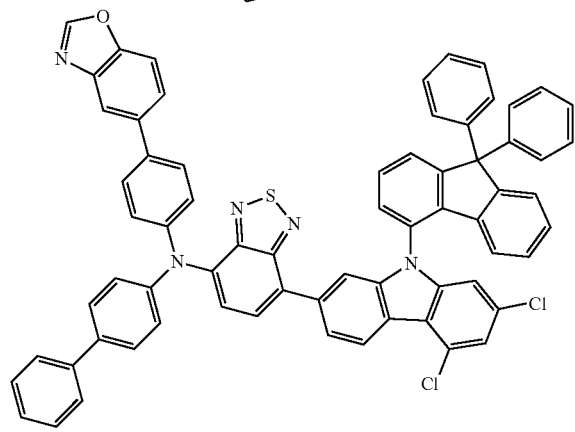
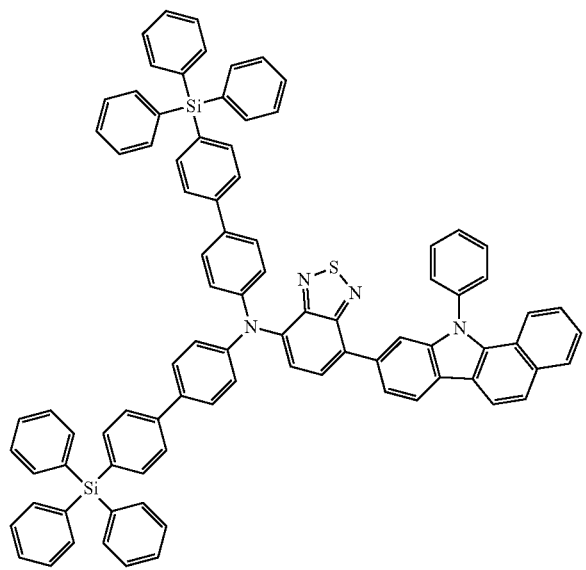

-continued
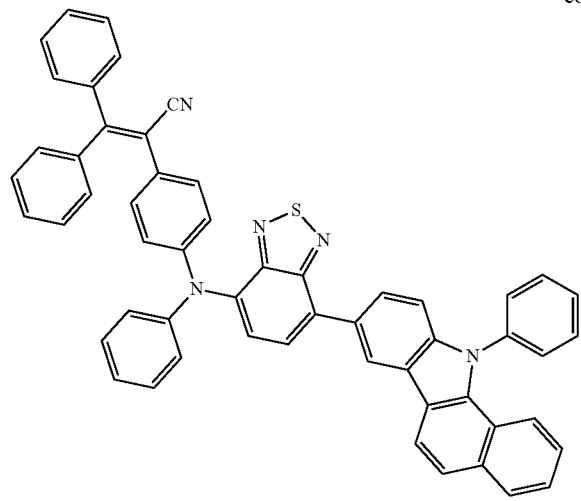 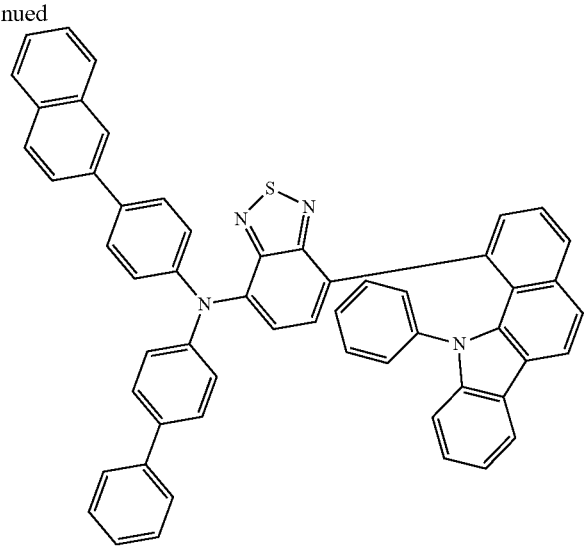
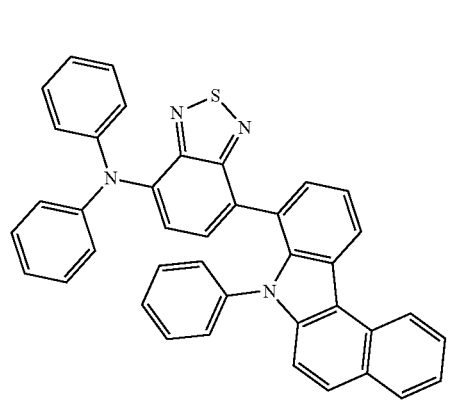 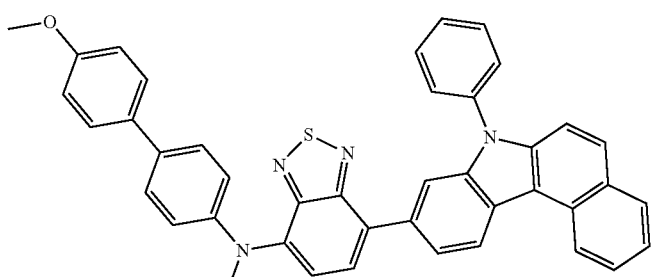
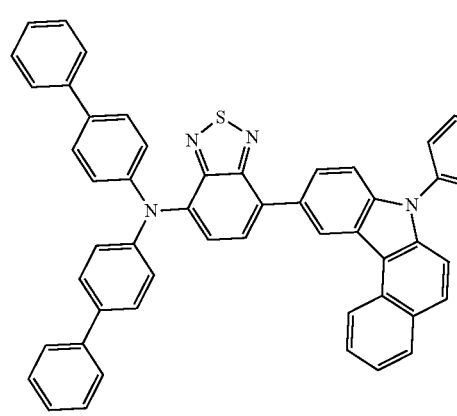 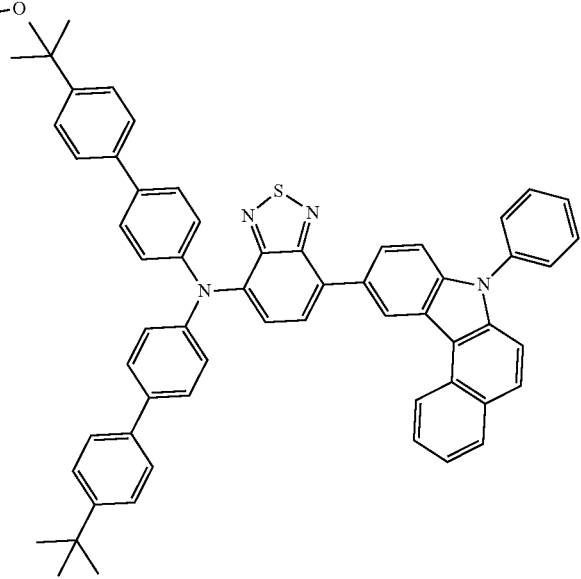

49
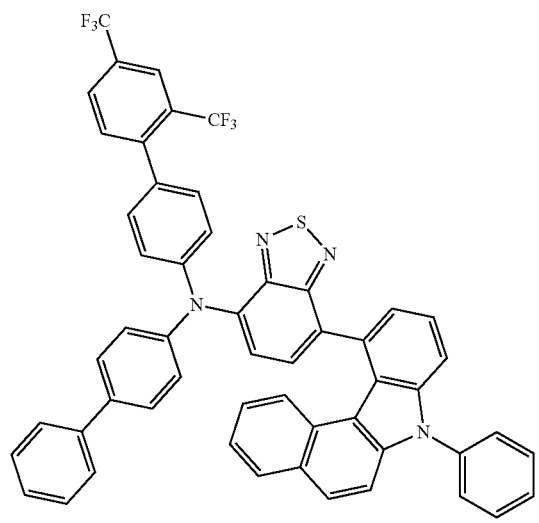
50
-continued
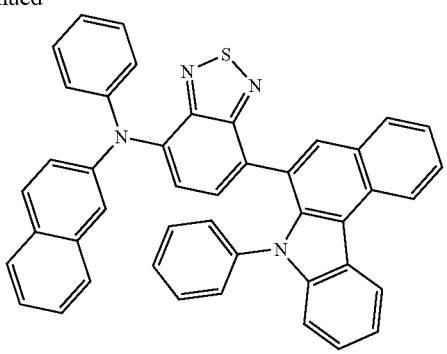
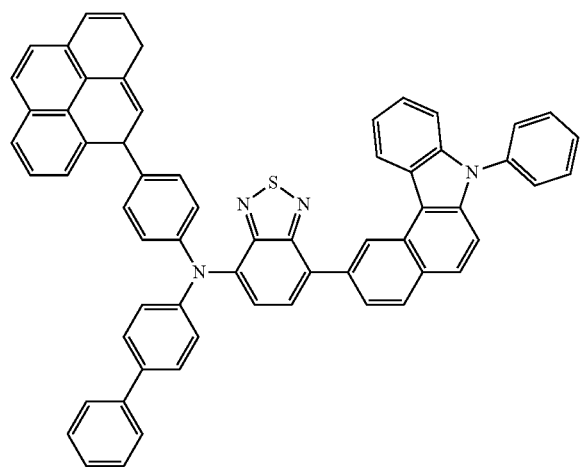
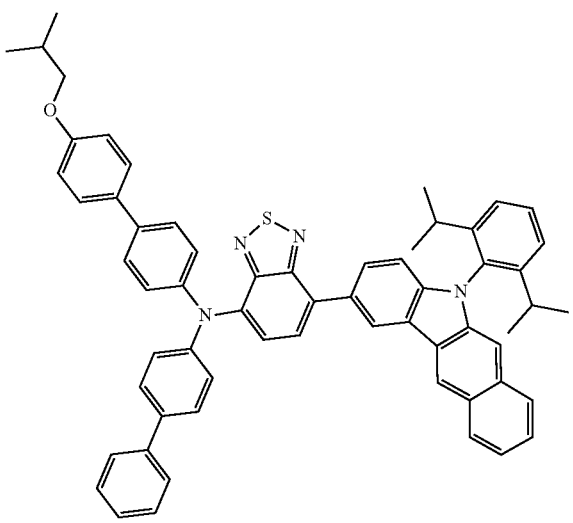
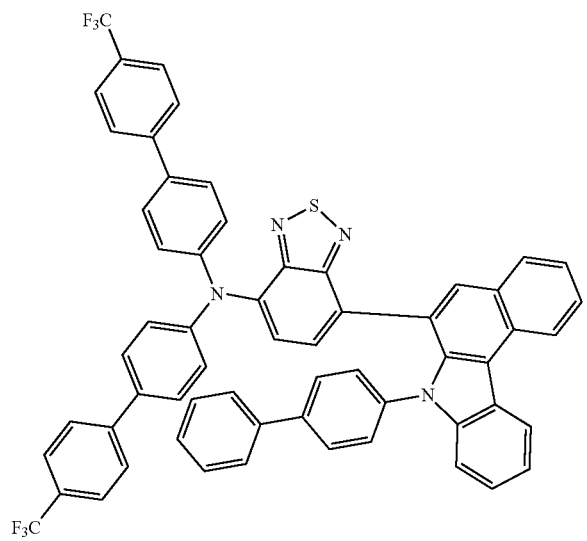
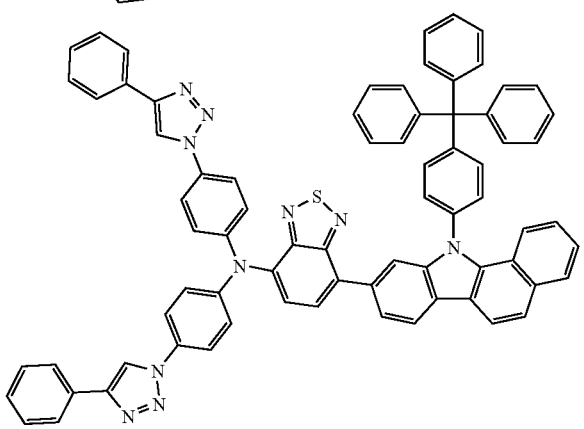

-continued
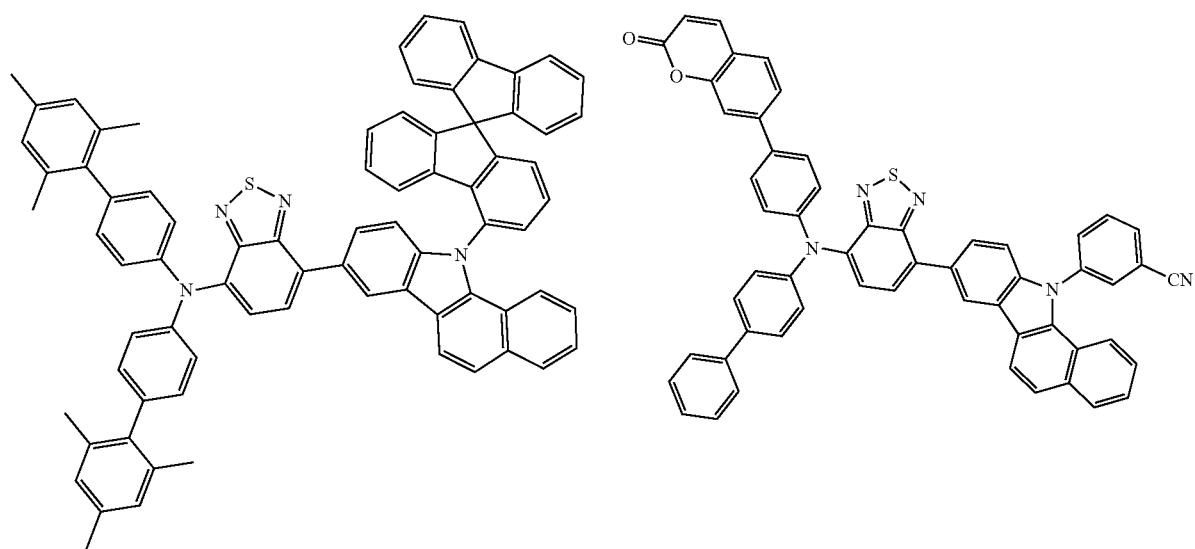
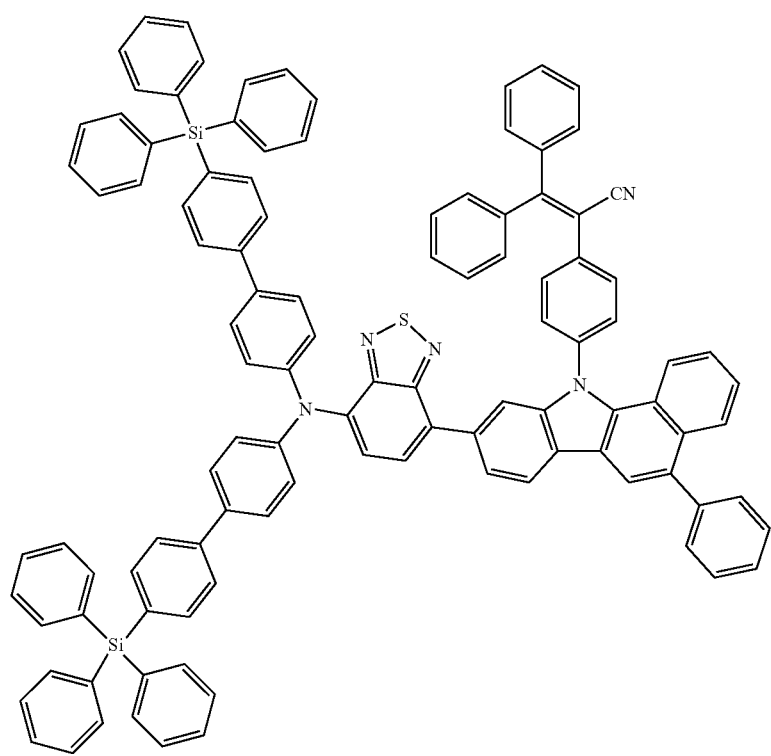

-continued
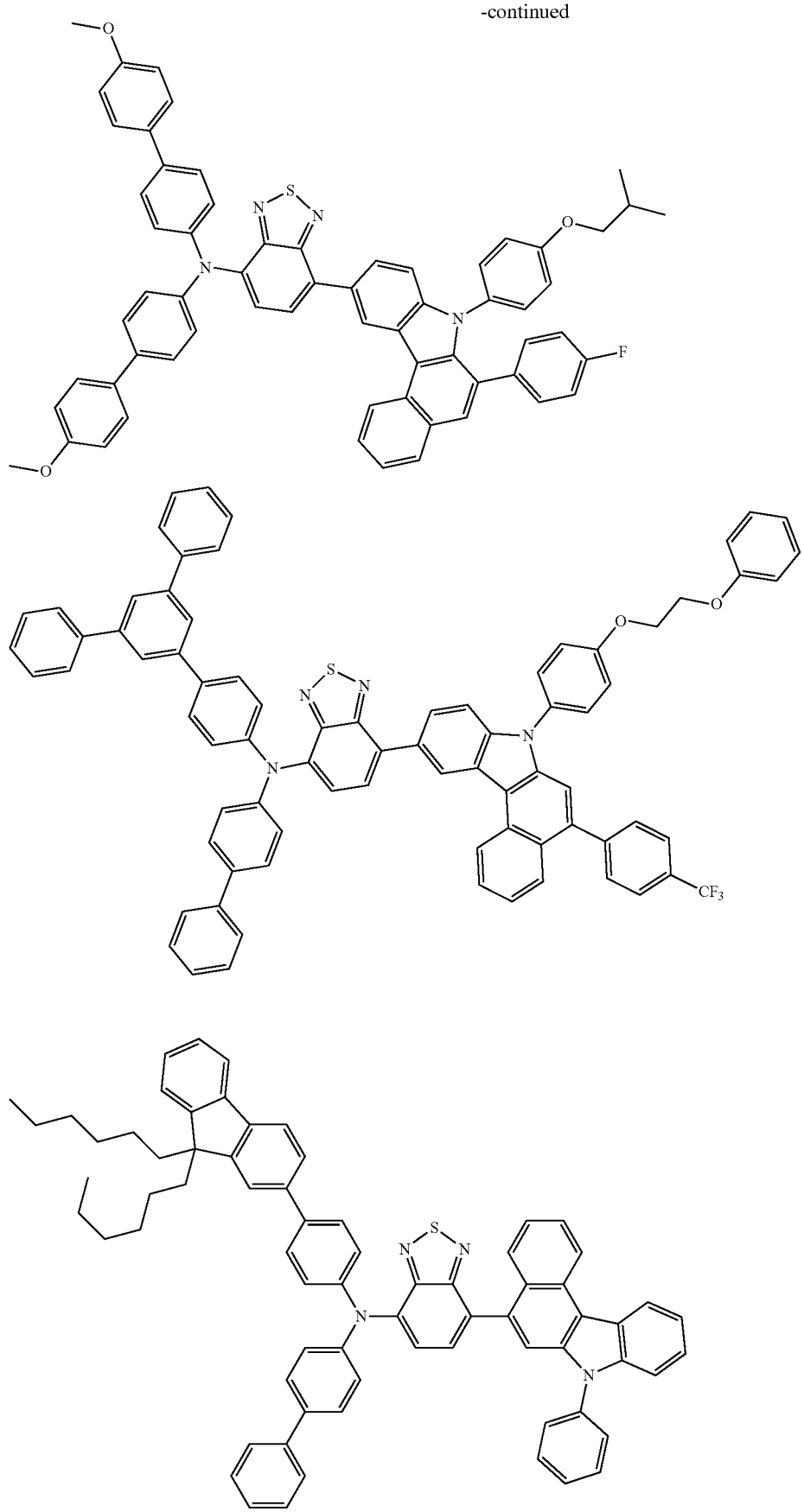

-continued
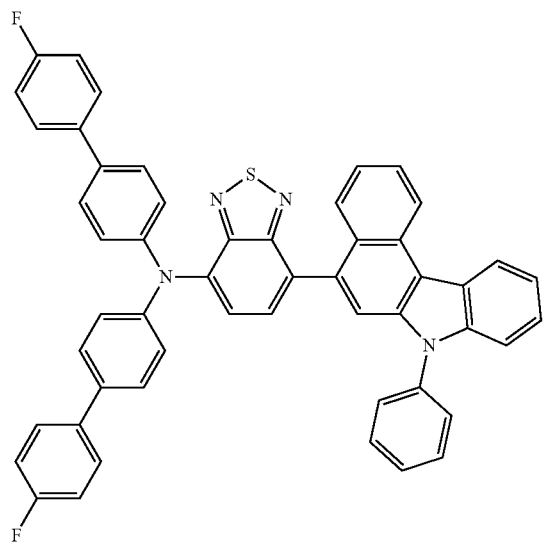
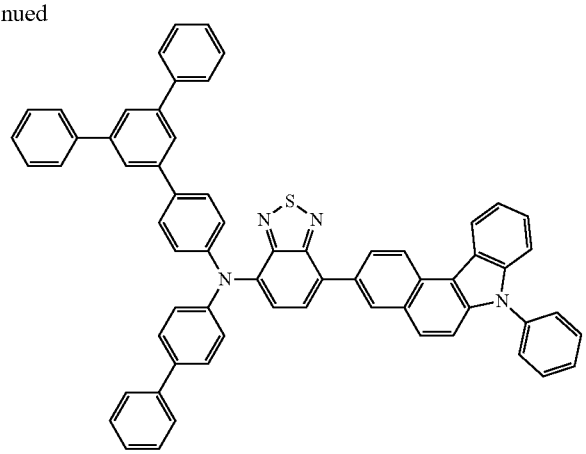
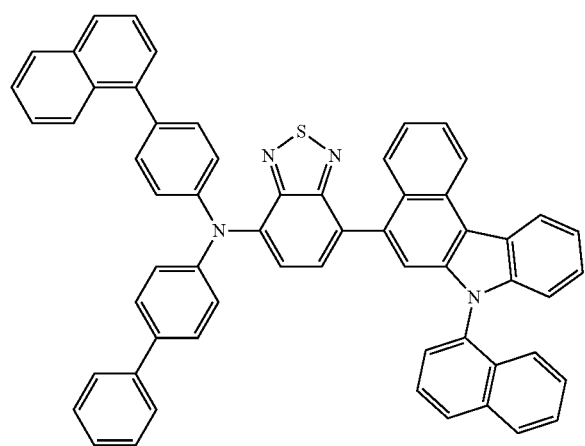
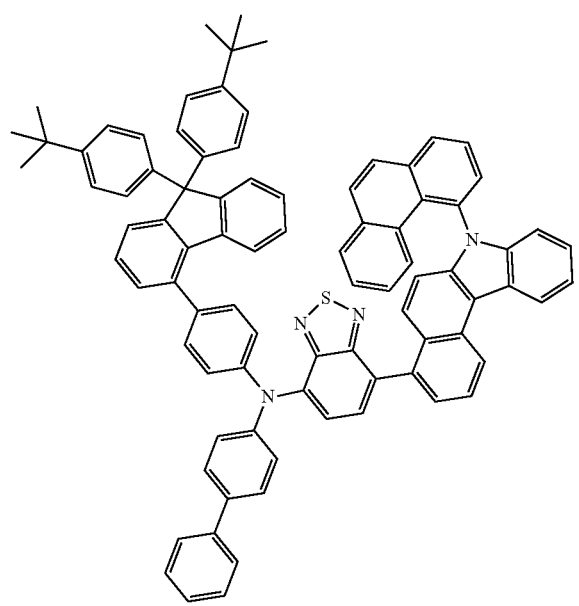
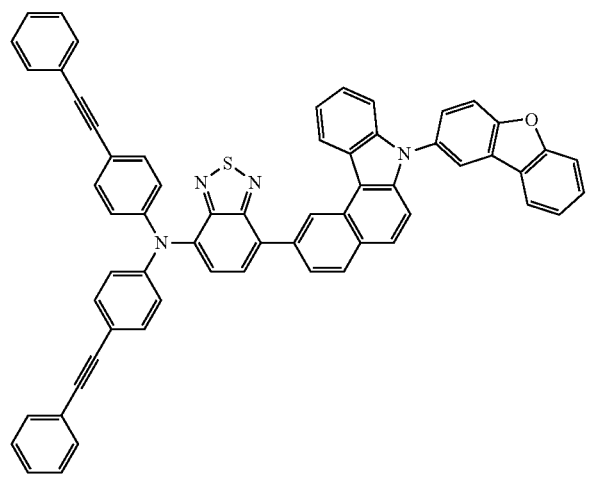
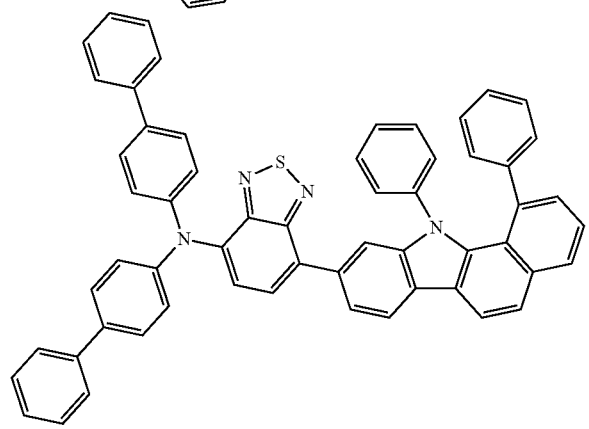

-continued
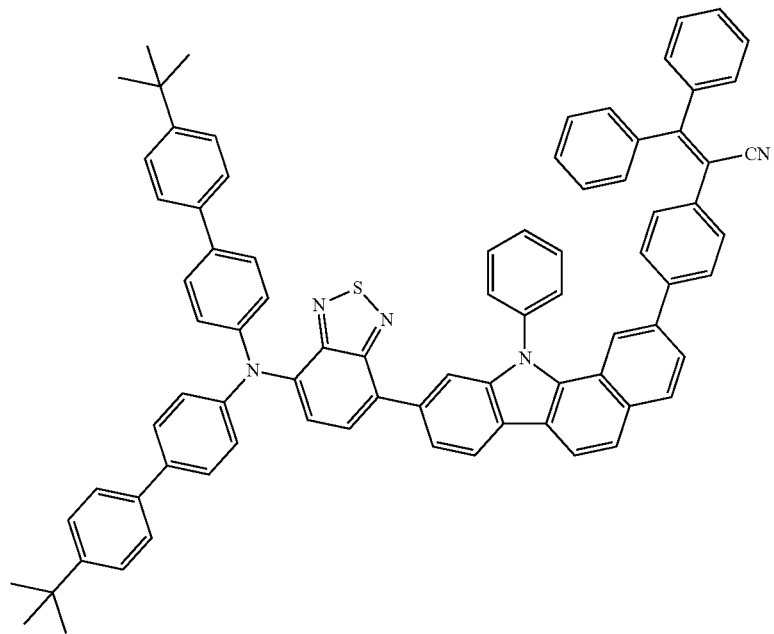
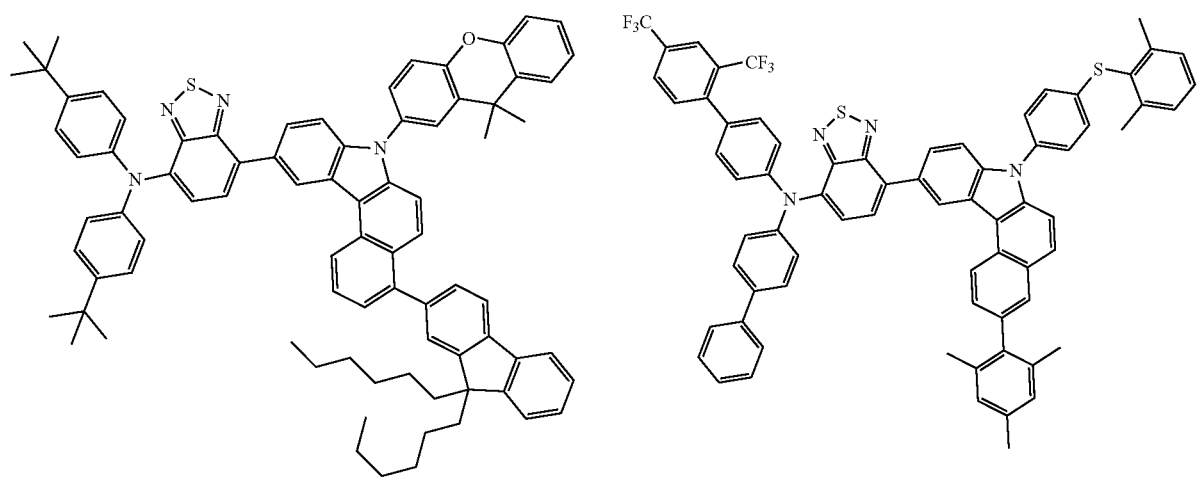

-continued
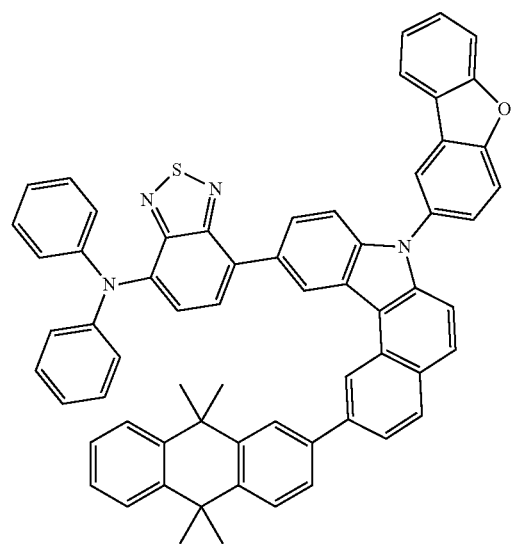
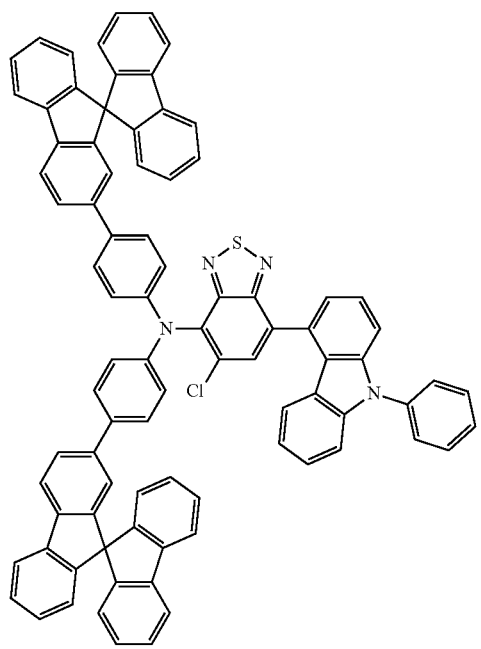
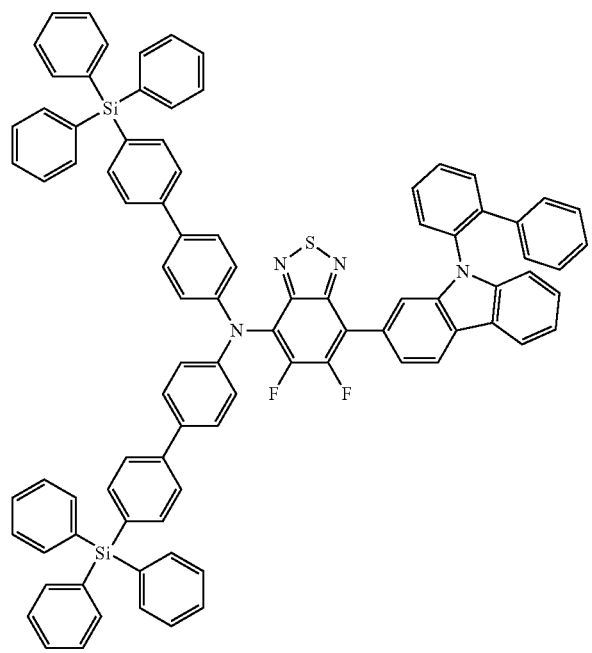

The compound according to an exemplary embodiment of the present specification may be prepared by a preparation method to be described below.

For example, the compound having the structure of Formula 1 may be prepared through the following Reaction Formulae 1 and 2. The substituent may be bonded by a method known in the art, and the kind and position of the substituent or the number of substituents may be changed according to the technology known in the art.

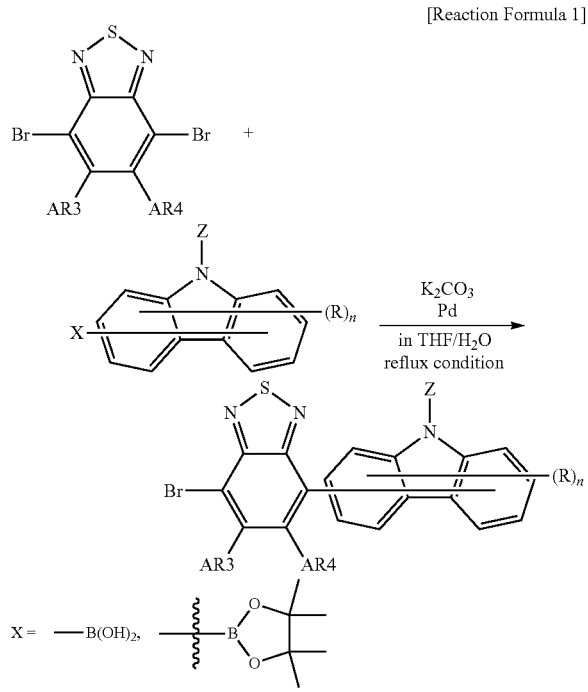

[Reaction Formula 1]

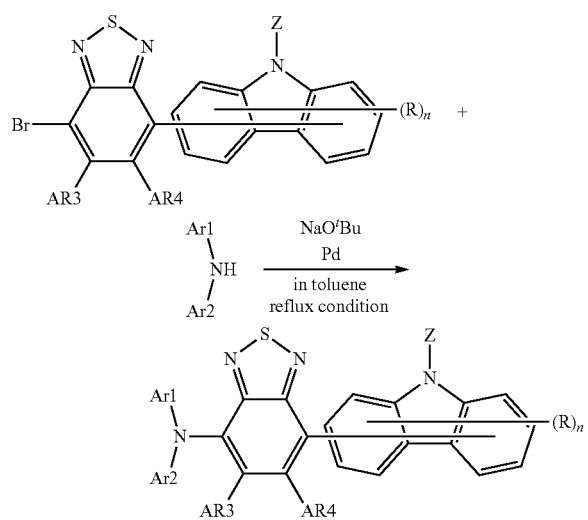

[Reaction Formula 2]

In Reaction Formulae 1 and 2, AR3, AR4, R, and Z are the same as the above-described definitions in Formula 1.

An exemplary embodiment of the present specification provides a color conversion film including: a resin matrix; and the compound represented by Formula 1, which is dispersed in the resin matrix.

The content of the compound represented by Formula 1 in the color conversion film may be within a range of 0.001 wt % to 15 wt %.

The color conversion film may include one or two or more of the compounds represented by Formula 1. For example, the color conversion film may include one compound, which emits green light, among the compounds represented by Formula 1. As another example, the color conversion film may include one compound, which emits red light, among the compounds represented by Formula 1. As still another example, the color conversion film may include one compound, which emits green light, and two or more compounds, which emit red light, among the compounds represented by Formula 1.

The color conversion film may further include an additional fluorescent material in addition to the compound represented by Formula 1. When a light source which emits blue light is used, it is preferred that the color conversion film includes both a fluorescent material which emits green light and a fluorescent material which emits red light. Further, when a light source which emits blue light and green light is used, the color conversion film may include only a fluorescent material which emits red light. However, the color conversion film is not limited thereto, and even when a light source which emits blue light is used, the color conversion film may include only a compound, which emits red light, in the case where a separate film including a fluorescent material which emits green light is stacked. Conversely, even when a light source which emits blue light is used, the color conversion film may include only a compound, which emits green light, in the case where a separate film including a fluorescent material which emits red light is stacked.

The color conversion film may further include: a resin matrix; and an additional layer including a compound which is dispersed in the resin matrix and emits light having a wavelength different from that of the compound represented by Formula 1. The compound which emits light having a wavelength different from that of the compound represented by Formula 1 may also be the compound expressed as Formula 1, and may also be another publicly-known fluorescent material.

It is preferred that a material for the resin matrix is a thermoplastic polymer or a thermosetting polymer. Specifically, as the material for the resin matrix, it is possible to use a poly(meth)acrylic material such as polymethylmethacrylate (PMMA), a polycarbonate (PC)-based material, a polystyrene (PS)-based material, a polyarylene (PAR)-based material, a polyurethane (TPU)-based material, a styrene-acrylonitrile (SAN)-based material, a polyvinylidenefluoride (PVDF)-based material, a modified-polyvinylidenefluoride (modified-PVDF)-based material, and the like.

According to an exemplary embodiment of the present specification, the color conversion film according to the above-described exemplary embodiment additionally includes light diffusion particles. By dispersing light diffusion particles in the color conversion film instead of a light diffusion film used in the related art in order to improve brightness, an attachment process may be omitted, and higher brightness may be exhibited, as compared to the case where a separate light diffusion film is used.

As the light diffusion particle having a higher refractive index than a resin matrix may be used, and it is possible to use, for example, $TiO_2$, silica, borosilicate, alumina, sapphire, air or another gas, air- or gas-filled hollow beads or particles (for example, air/gas-filled glass or polymer); polymer particles including polystyrene, polycarbonate, polymethylmethacrylate, acryl, methyl methacrylate, styrene, a melamine resin, a formaldehyde resin, or a melamine and formaldehyde resin, or any suitable combination thereof.

The particle diameter of the light diffusion particles may be within a range of 0.1 µm to 5 µm, for example, within a range of 0.3 µm to 1 µm. The content of the light diffusion particles may be determined, if necessary, and may be, for example, within a range of about 1 part by weight to about 30 parts by weight based on 100 parts by weight of the resin matrix.

The color conversion film according to the above-described exemplary embodiment may have a thickness of 0.1 µm to 200 µm. In particular, the color conversion film may exhibit high brightness even with a small thickness of 0.1 µm to 20 µm. This is because the content of the fluorescent material molecules included in a unit volume is higher than that of a quantum dot.

A base material may be provided on one surface of the color conversion film according to the above-described exemplary embodiment. The base material may function as a support when manufacturing the color conversion film. The kind of base material is not particularly limited, and the material or thickness of the base material is not limited as long as the base material is transparent and may function as the support. Here, transparency means that the transmittance in visible light is 70% or more. For example, as the base material, a PET film may be used.

The above-described color conversion film may be prepared by coating a base material with a resin solution, in which the above-described compound represented by Formula 1 is dissolved, and drying the resin solution, or extruding the above-described compound represented by Formula 1 together with the resin to produce a film.

Since the above-described compound represented by Formula 1 is dissolved in the resin solution, the compound represented by Formula 1 is uniformly distributed in the solution. This is different from a process of producing a quantum dot film, which requires a separate dispersing process.

The preparation method of the resin solution in which the compound represented by Formula 1 is dissolved is not particularly limited as long as the above-described compound represented by Formula 1 is in a state where the resin is dissolved in the solution.

According to an example, the resin solution in which the compound represented by Formula 1 is dissolved may be prepared by a method of dissolving the compound represented by Formula 1 in a solvent to prepare a first solution, dissolving a resin in a solvent to prepare a second solution, and mixing the first solution with the second solution. When the first solution and the second solution are mixed, it is preferred to uniformly mix the solutions. However, the method is not limited thereto, and it is possible to use a method of simultaneously adding the compound represented by Formula 1 and a resin to a solvent to dissolve the compound and the resin, a method of dissolving the compound represented by Formula 1 in a solvent, and subsequently adding a resin thereto to dissolve the resin, a method of dissolving a resin in a solvent, and subsequently adding the compound represented by Formula 1 thereto to dissolve the compound, and the like.

As the resin included in the solution, it is possible to use the above-described resin matrix material, a monomer which is curable by the resin matrix material, or a mixture thereof. Examples of the monomer which is curable by the resin matrix material include a (meth)acrylic monomer, and the monomer may be formed of a resin matrix material by UV curing. When a curable monomer is used as described above, an initiator required for curing may be further added, if necessary.

The solvent is not particularly limited, and is not particularly limited as long as the solvent does not adversely affect the coating process and may be removed by a subsequent drying. As the non-limiting example of the solvent, it is possible to use acetone, toluene, chloroform, methyl ethyl ketone, methyl isobutyl ketone, methyl cellosolve, ethyl cellosolve, tetrahydrofuran, 1,4-dioxane, ethylene glycol dimethyl ether, ethylene glycol diethyl ether, propylene glycol dimethyl ether, propylene glycol methyl ether acetate, propylene glycol diethyl ether, diethylene glycol dimethyl ether, diethylene glycol diethyl ether, diethylene glycol methyl ethyl ether, chloroform, methylene chloride, 1,2-dichloroethane, 1,1,1-trichloroethane, 1,1,2-trichloroethane, 1,1,2-trichloroethene, hexane, heptane, octane, cyclohexane, benzene, toluene, xylene, methanol, ethanol, isopropanol, propanol, butanol, t-butanol, 2-ethoxy propanol, 2-methoxy propanol, 3-methoxy butanol, cyclohexanone, cyclopentanone, propylene glycol methyl ether acetate, propylene glycol ethyl ether acetate, 3-methoxybutyl acetate, ethyl 3-ethoxypropionate, ethyl cellosolve acetate, methyl cellosolve acetate, butyl acetate, dipropylene glycol monomethyl ether, and the like, and one or a mixture of two or more may be used. When the first solution and the second solution are used, the solvents included in the respective solutions may also be the same as or different from each other. Even when different solvents are used in the first solution and the second solution, it is preferred that these solvents have compatibility so as to be mixed with each other.

For the process of coating a base material with the resin solution, in which the compound represented by Formula 1 is dissolved, a roll-to-roll process may be used. For example, the roll-to-roll process may be performed by a process of unwinding a base material from a roll on which the base material is wound, coating one surface of the base material with a resin solution, in which the compound represented by Formula 1 is dissolved, drying the resin solution, and then winding the base material again on the roll. When the roll-to-roll process is used, it is preferred that the viscosity of the resin solution is determined within a range in which the process may be implemented, and the viscosity may be determined within a range of, for example, 200 cps to 2,000 cps.

As the coating method, various publicly-known methods may be used, and for example, a die coater may also be used, and various bar-coating methods such as a comma coater and a reverse comma coater may also be used.

After the coating, a drying process is performed. The drying process may be performed under conditions required for removing the solvent. For example, it is possible to obtain a color conversion film including a fluorescent material including the compound represented by Formula 1, which has a desired thickness and concentration, on a base material by carrying out the drying in an oven located close to a coater under a condition to sufficiently evaporate a solvent, in a direction in which the base material progresses during the coating process.

When the monomer which is curable by the resin matrix material is used as a resin included in the solution, curing, for example, UV curing may be performed before the drying or simultaneously with the drying.

When the compound represented by Formula 1 is extruded with a resin to produce a film, an extrusion method known in the art may be used, and for example, a color conversion film may be prepared by extruding the compound represented by Formula 1 with a resin such as a polycarbonate (PC)-based resin, a poly(meth)acrylic resin, and a styrene-acrylonitrile (SAN)-based resin.

According to an exemplary embodiment of the present specification, a protective film or a barrier film may be provided on at least one surface of the color conversion film. As the protective film and the barrier film, films known in the art may be used.

Another exemplary embodiment of the present specification provides a backlight unit including the above-described color conversion film. The backlight unit may have a backlight unit configuration known in the art, except that the backlight unit includes the color conversion film. For example, FIG. 1 illustrates an example thereof. According to FIG. 1, the color conversion film according to the above-described exemplary embodiments is provided on a surface opposite to a surface of a light guide plate facing a reflective plate. FIG. 1 exemplifies a configuration including a light source and a reflective plate surrounding the light source, but the configuration is not limited to such a structure, and may be modified depending on the structure of the backlight unit known in the art. Further, as a light source, a direct type as well as a side chain type may be used, and a reflective plate or a reflective layer may be omitted or replaced with other configurations, if necessary, and an additional film, for example, a light diffusion film, a light collecting film, a brightness enhancement film, and the like may be further provided, if necessary. Preferably, a light collecting film and a brightness enhancement film are further provided on a color conversion film.

In the configuration of the backlight unit illustrated in FIG. 1, a scattering pattern may be provided on an upper or lower surface of the light guide plate, if necessary. Light incident into the light guide plate has a non-uniform light distribution caused by repeated optical processes such as reflection, total reflection, refraction, and transmission, and the scattering pattern may be used for inducing the non-uniform light distribution to uniform luminance.

According to still another exemplary embodiment of the present application, a display device including the above-described backlight unit is applied. The display device is not particularly limited as long as the device includes the above-described backlight unit as a constituent element. For example, the display device includes a display module and a backlight unit. FIG. 2 illustrates a structure of a display device. However, the structure is not limited thereto, and an additional film, for example, a light diffusion film, a light collecting film, a brightness enhancement film, and the like may be further provided between the display module and the backlight unit, if necessary.

Hereinafter, the present specification will be described in detail with reference to Examples for specifically describing the present specification. However, the Examples according to the present specification may be modified in various forms, and it is not interpreted that the scope of the present application is limited to the Examples described in detail below. The Examples of the present application are provided for more completely explaining the present specification to the person with ordinary skill in the art.

MODE FOR INVENTION

Preparation Examples

The compound according to an exemplary embodiment of the present specification may be prepared by a preparation method to be described below.

For example, the core structure of the compound having the structure of Formula 1 may be prepared by the following Reaction Formulae 1 and 2. The substituent may be bonded by a method known in the art, and the kind and position of the substituent or the number of substituents may be changed according to the technology known in the art.

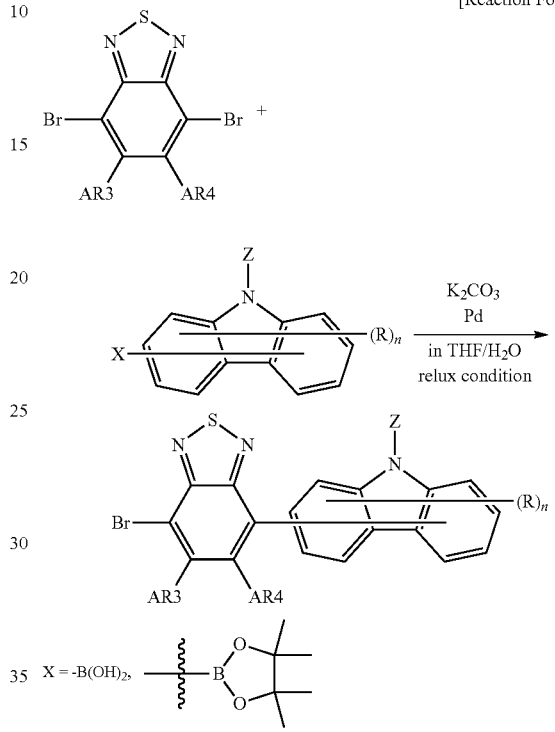

[Reaction Formula 1]

1.1 equivalents of benzothiadiazole and 1 equivalent of a carbazole derivative were stirred under a tetrahydrofuran solvent, 2 equivalents of potassium carbonate were dissolved in water, and the resulting solution was added thereto. A reaction was performed under a nitrogen atmosphere by using 0.05 equivalent of tetrakistriphenylphosphine as a catalyst. After the reaction was terminated, the reactant was cooled to room temperature, and the product was precipitated as a solid by pouring water into the reactant. The produced solid was separated from the solution through a filter, and then purified through a column.

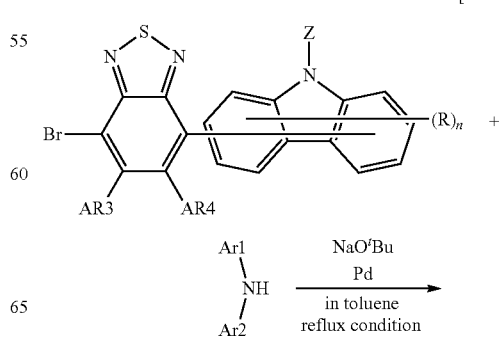

[Reaction Formula 2]

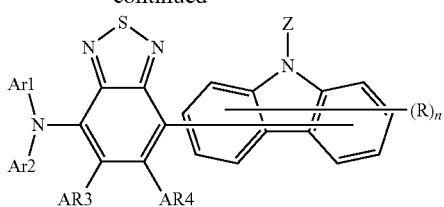

1 equivalent of the compound obtained in Reaction Formula 1, 1.3 equivalents of an amine derivative, and 3 equivalents of NaOtBu were stirred under a toluene solvent and a nitrogen atmosphere. After the reflux condition was reached, the reaction was performed by using 0.03 equivalent of BTP as a catalyst. After the reaction was terminated, the reactant was cooled to room temperature. The produced solid was filtered, and then purified through a column.

Preparation Example 1. Compound 1

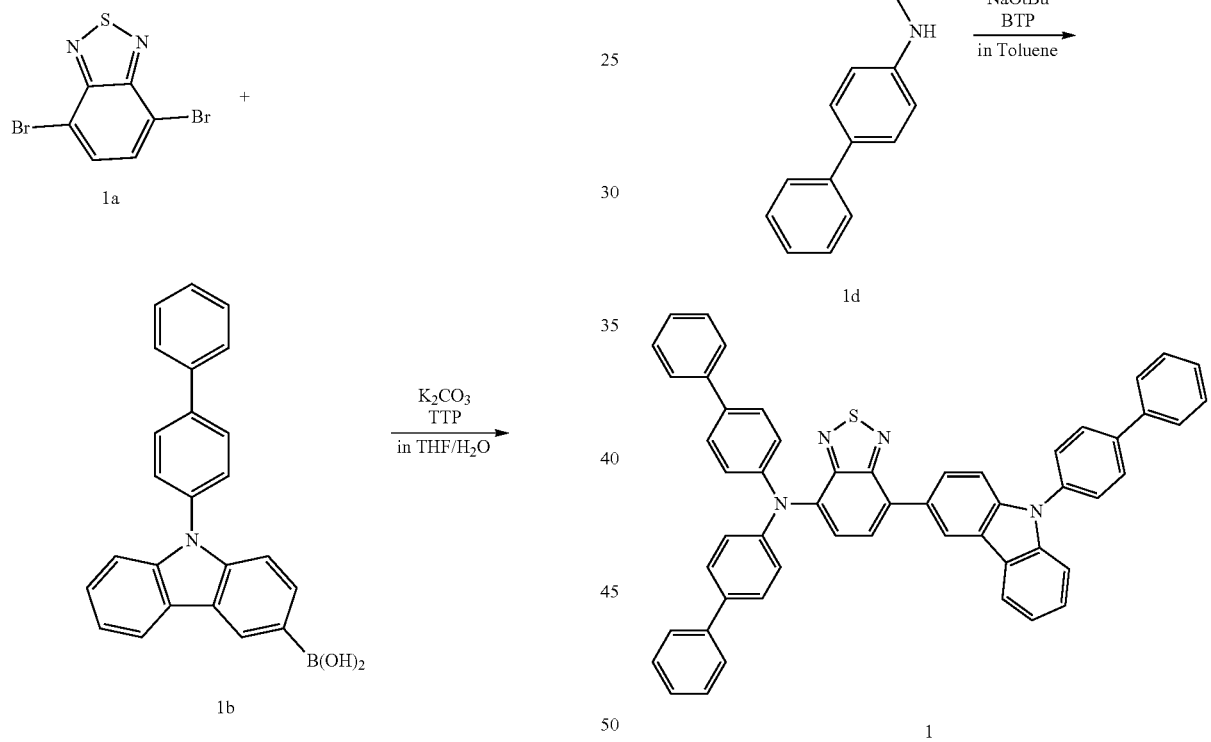

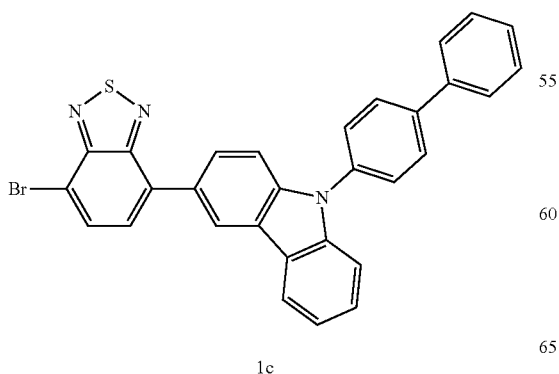

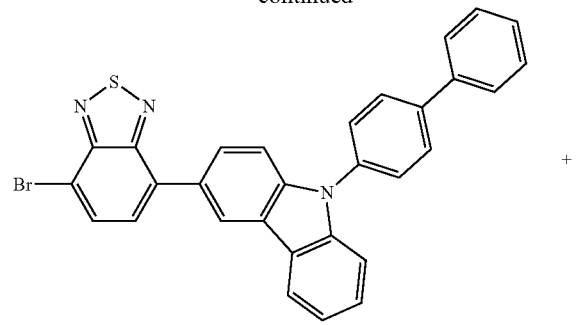

1) Synthesis of Compound 1c 2.00 g (6.80 mmol, 1.1 equivalents) of Compound 1a and 1 equivalent of Compound 1b were stirred under a tetrahydrofuran solvent, 2 equivalents of potassium carbonate were dissolved in water, and the resulting solution was added thereto. A reaction was performed under a reflux condition and a nitrogen atmosphere by using 0.05 equivalent of tetrakistriphenylphosphine as a catalyst. After the reaction was terminated, the reactant was cooled to room temperature, and the product was precipitated as a solid by pouring water into the reactant. The produced solid was filtered, and then purified through a column to obtain 2.31 g (yield 70%) of Compound 1c.

2) Synthesis of Compound 1

2.31 g (4.32 mmol, 1 equivalent) of Compound 1c, 1.3 equivalents of Compound 1d, and 3 equivalents of NaOtBu were stirred under a toluene solvent and a nitrogen atmosphere. After the reflux condition was reached, the reaction was performed by using 0.03 equivalent of BTP as a catalyst. After the reaction was terminated, the reactant was cooled to room temperature, and the product was precipitated as a solid by pouring water into the reactant. The produced solid was filtered, and then purified through a column to obtain 3.00 g (yield 90%) of Compound 1.

HR LC/MS/MS m/z calcd for $C_{54}H_{36}N_4S$ (M+): 772.2661; found: 772.2660.

Preparation Example 2. Compound 2

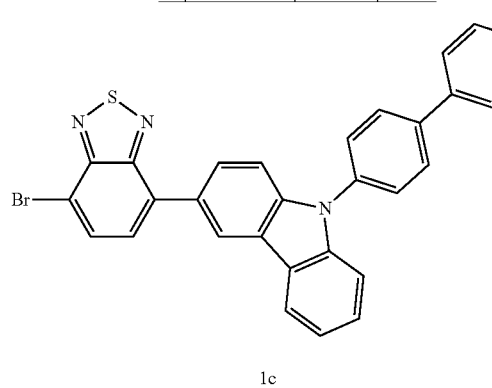

1c

+

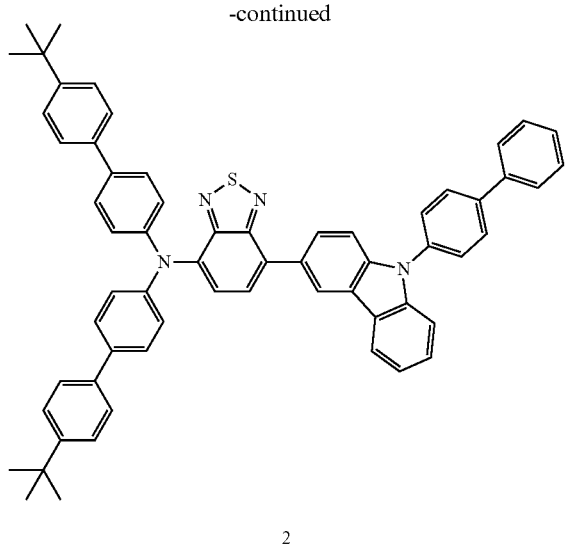

2

1) Synthesis of Compound 2

2.30 g (4.32 mmol, 1 equivalent) of Compound 1c, 1.3 equivalents of Compound 2a, and 3 equivalents of NaOtBu were stirred under a toluene solvent and a nitrogen atmosphere. After the reflux condition was reached, the reaction was performed by using 0.03 equivalent of BTP as a catalyst. After the reaction was terminated, the reactant was cooled to room temperature, and the product was precipitated as a solid by pouring water into the reactant. The produced solid was filtered, and then purified through a column to obtain 2.87 g (yield 75%) of Compound 2. HR LC/MS/MS m/z calcd for $C_{62}H_{52}N_4S$ (M+): 884.3913; found: 884.3910.

Preparation Example 3. Compound 3

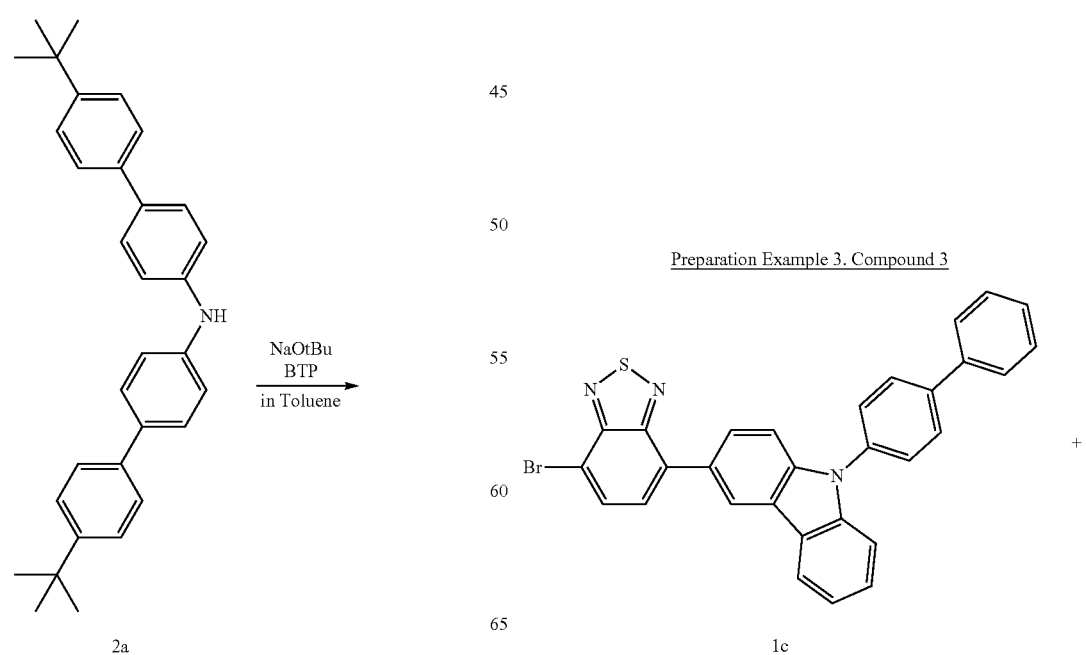

-continued

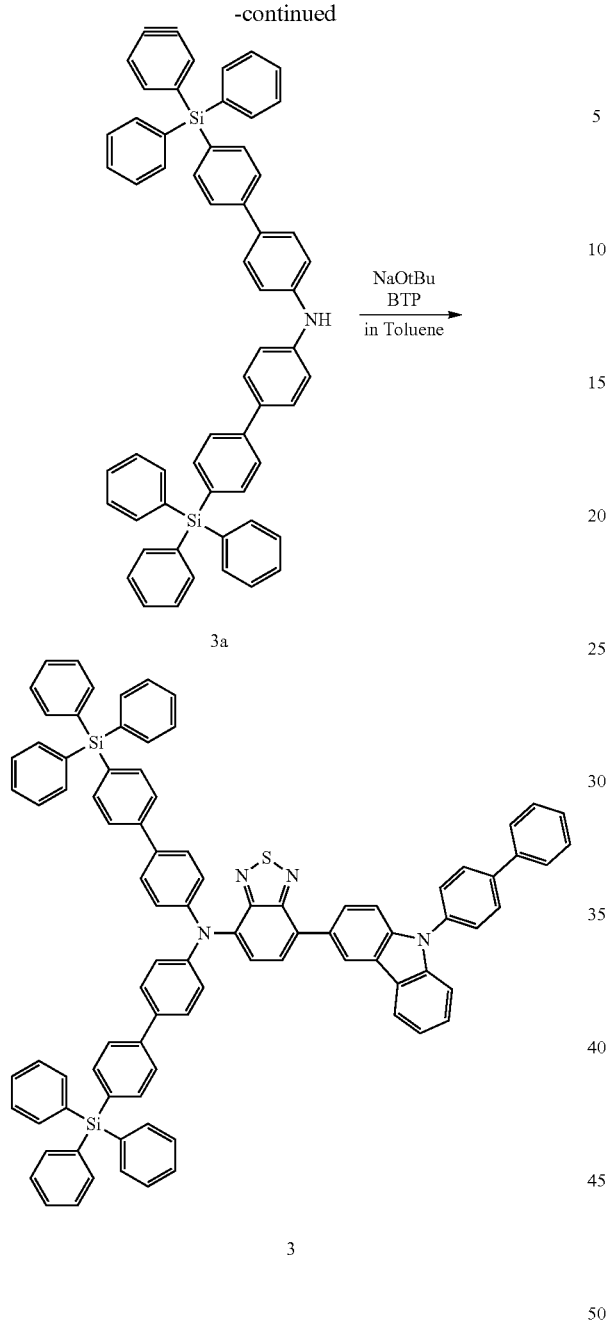

3a

3

1) Synthesis of Compound 3

2.30 g (4.32 mmol, 1 equivalent) of Compound 1c, 1.3 equivalents of Compound 3a, and 3 equivalents of NaOtBu were stirred under a toluene solvent and a nitrogen atmosphere. After the reflux condition was reached, the reaction was performed by using 0.03 equivalent of BTP as a catalyst. After the reaction was terminated, the reactant was cooled to room temperature, and the product was precipitated as a solid by pouring water into the reactant. The produced solid was filtered, and then purified through a column to obtain 3.45 g (yield 62%) of Compound 3.

HR LC/MS/MS m/z calcd for $C_{90}H_{64}N_4SSi_2$ (M+): 1288.4390; found: 1288.4386.

Preparation Example 4. Compound 4

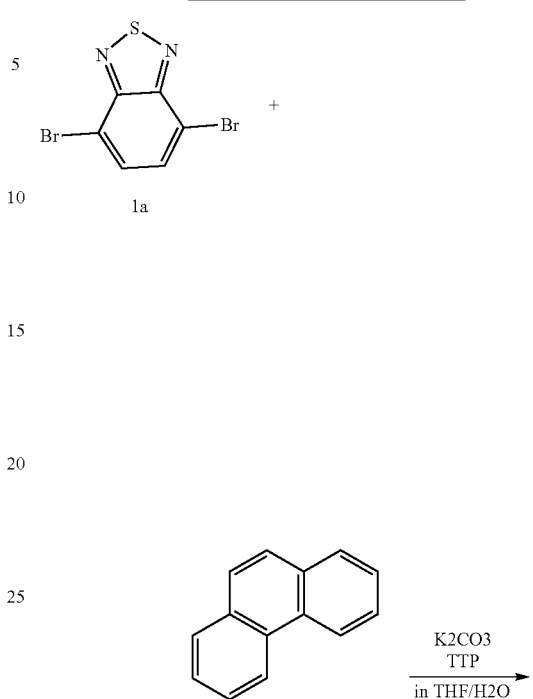

1a

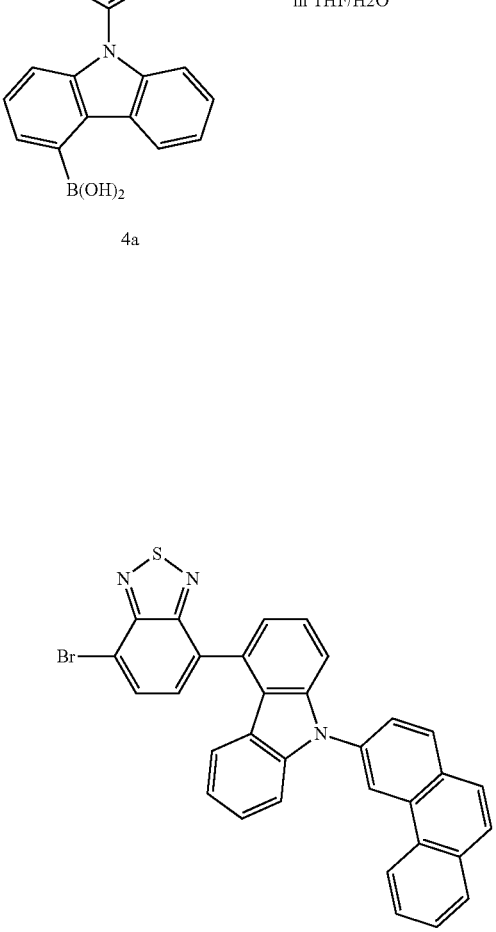

4a

4b

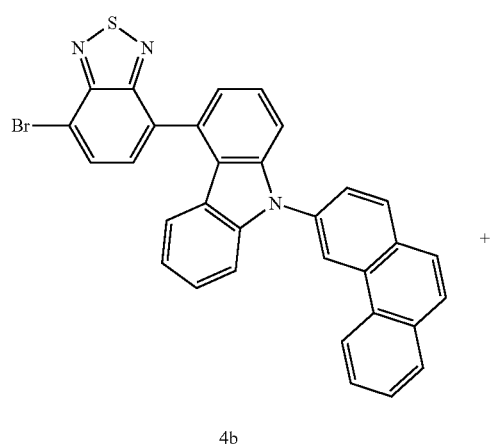

4b

+

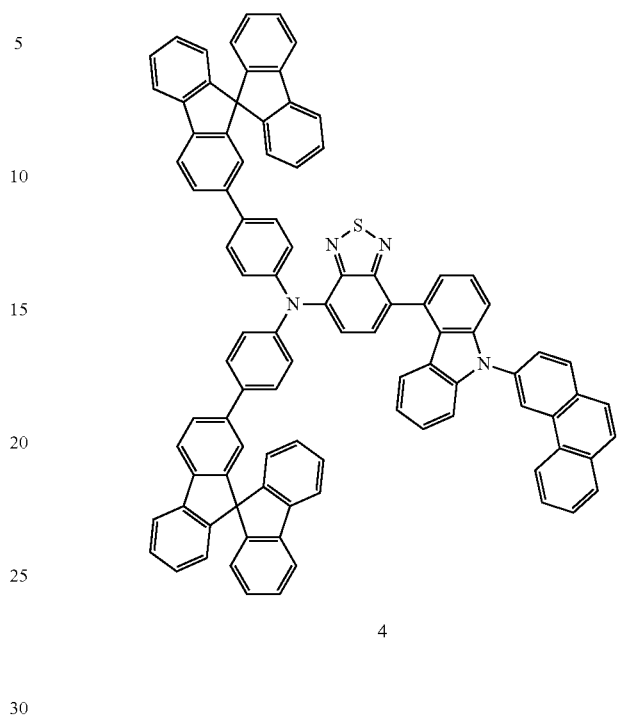

4

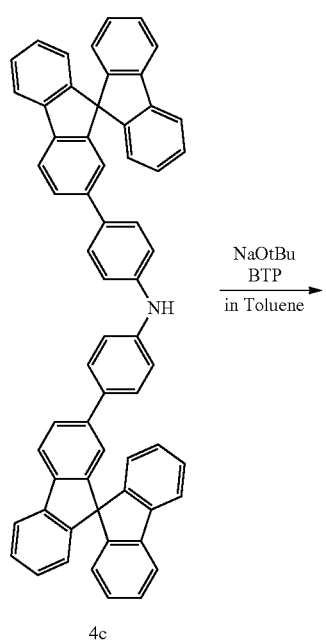

4c

1) Synthesis of Compound 4b 2.00 g (6.80 mmol, 1.1 equivalents) of Compound 1a and 1 equivalent of Compound 4a were stirred under a tetrahydrofuran solvent, 2 equivalents of potassium carbonate were dissolved in water, and the resulting solution was added thereto. A reaction was performed under a reflux condition and a nitrogen atmosphere by using 0.05 equivalent of tetrakistriphenylphosphine as a catalyst. After the reaction was terminated, the reactant was cooled to room temperature, and the product was precipitated as a solid by pouring water into the reactant. The produced solid was filtered, and then purified through a column to obtain 2.84 g (yield 75%) of Compound 4b.

2) Synthesis of Compound 4

2.84 g (5.10 mmol, 1 equivalent) of Compound 4b, 1.3 equivalents of Compound 4c, and 3 equivalents of NaOtBu were stirred under a toluene solvent and a nitrogen atmosphere. After the reflux condition was reached, the reaction was performed by using 0.03 equivalent of BTP as a catalyst. After the reaction was terminated, the reactant was cooled to room temperature, and the product was precipitated as a solid by pouring water into the reactant. The produced solid was filtered, and then purified through a column to obtain 3.06 g (yield 60%) of Compound 4.

HR LC/MS/MS m/z calcd for $C_{94}H_{56}N_4S$ (M+): 1273.4259; found: 1273.4255.

Preparation Example 5. Compound 5
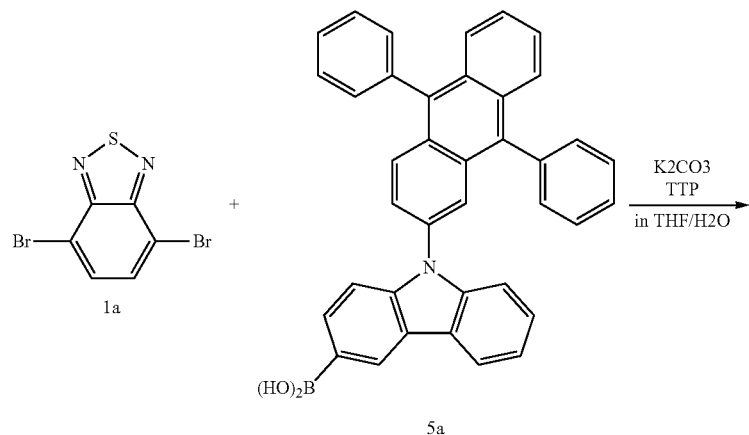
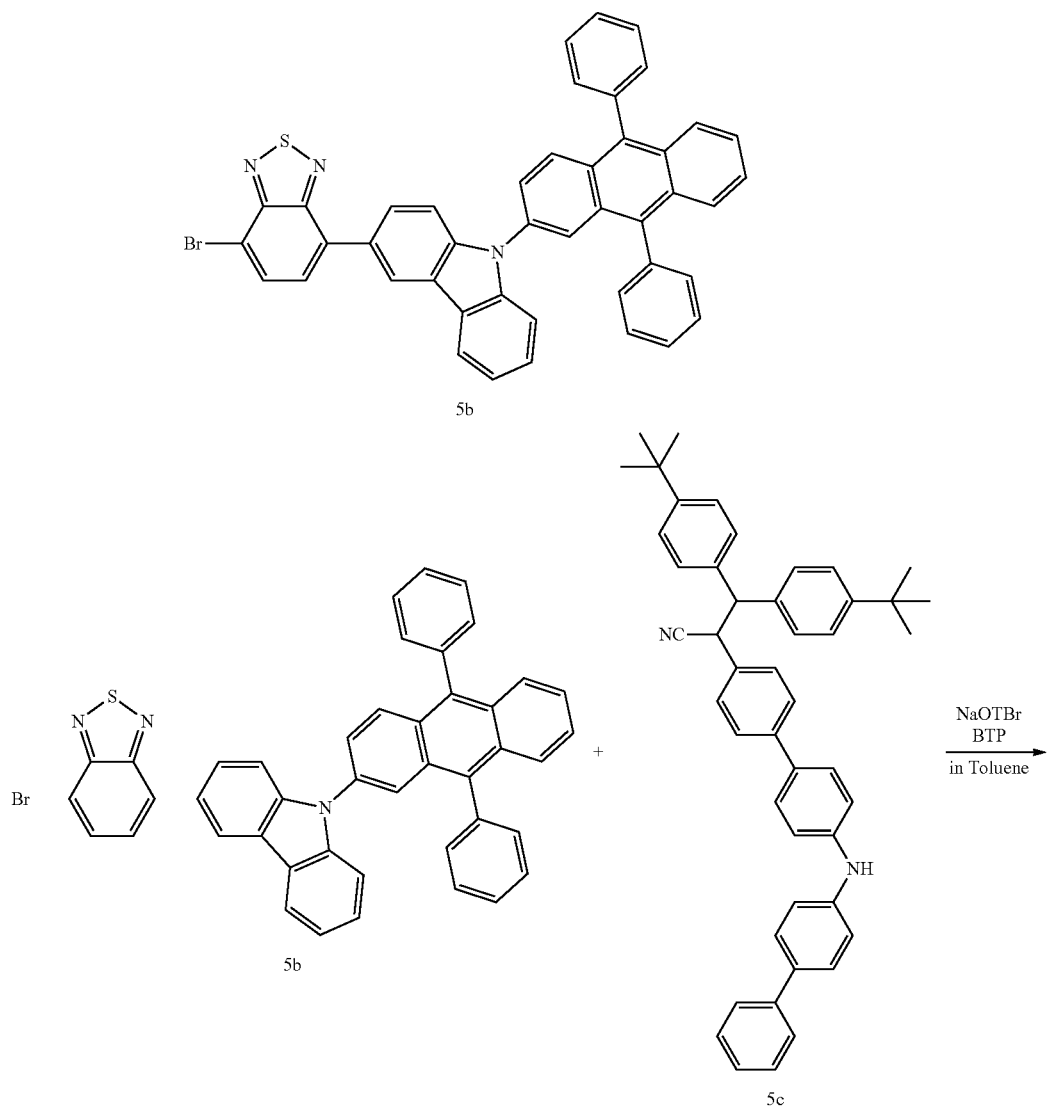

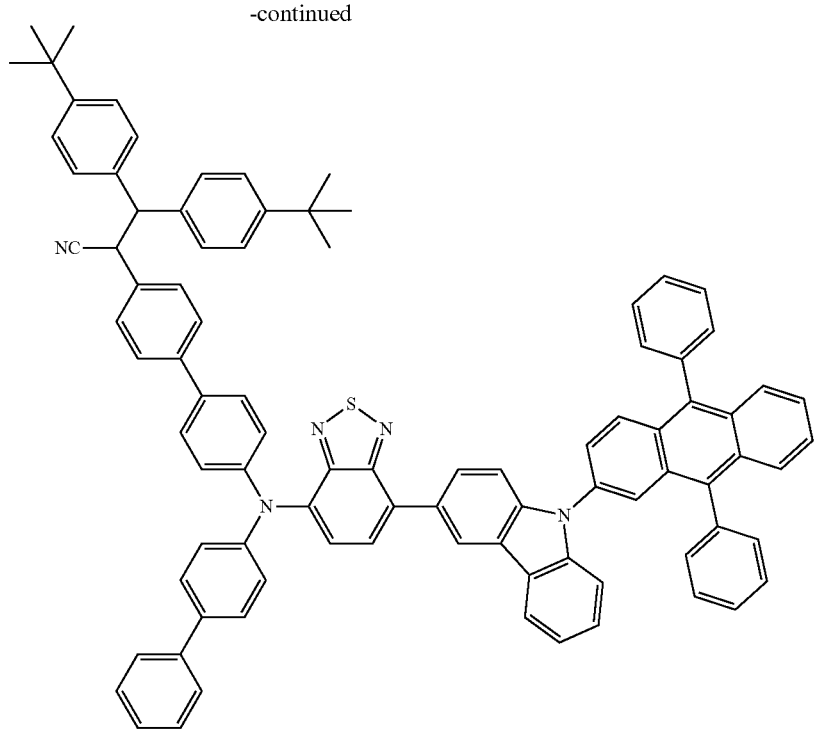

5

1) Synthesis of Compound 5b 2.00 g (6.80 mmol, 1.1 equivalents) of Compound 1a and 1 equivalent of Compound 5a were stirred under a tetrahydrofuran solvent, 2 equivalents of potassium carbonate were dissolved in water, and the resulting solution was added thereto. A reaction was performed under a reflux condition and a nitrogen atmosphere by using 0.05 equivalent of tetrakistriphenylphosphine as a catalyst. After the reaction was terminated, the reactant was cooled to room temperature, and the product was precipitated as a solid by pouring water into the reactant. The produced solid was filtered, and then purified through a column to obtain 3.28 g (yield 68%) of Compound 5b.

2) Synthesis of Compound 5

3.28 g (4.62 mmol, 1 equivalent) of Compound 5b, 1.3 equivalents of Compound 5c, and 3 equivalents of NaOtBu were stirred under a toluene solvent and a nitrogen atmosphere. After the reflux condition was reached, the reaction was performed by using 0.03 equivalent of BTP as a catalyst. After the reaction was terminated, the reactant was cooled to room temperature, and the product was precipitated as a solid by pouring water into the reactant. The produced solid was filtered, and then purified through a column to obtain 4.97 g (yield 85%) of Compound 5.

HR LC/MS/MS m/z calcd for $C_{91}H_{69}N_5S$ (M+): 1263.5274; found: 1263.5276.

Preparation Example 6. Compound 6

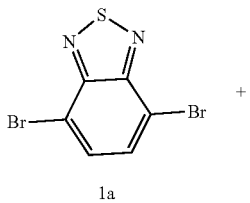

1a

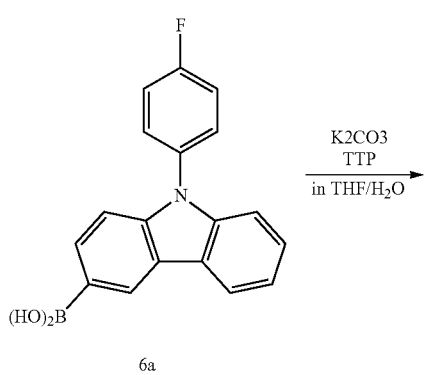

6a

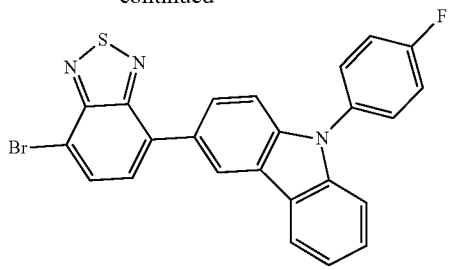

6b

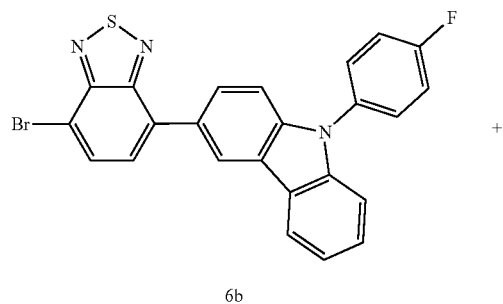

6b

+

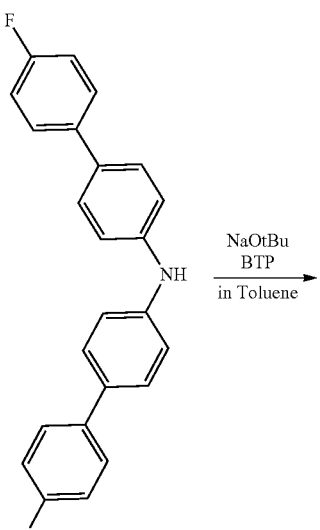

6c

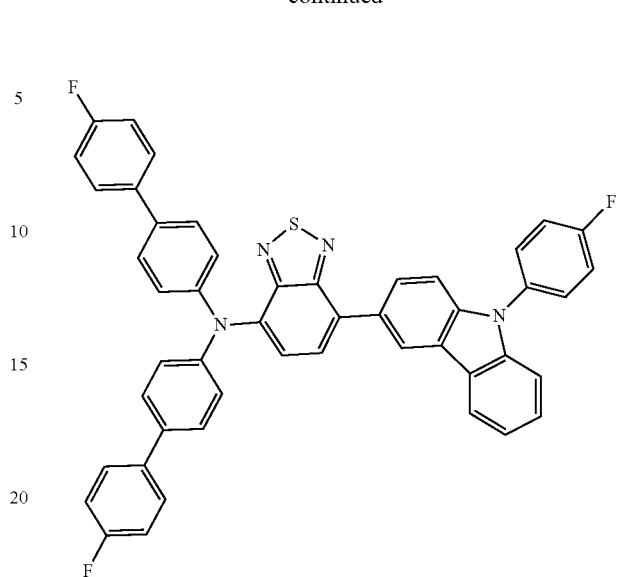

6

1) Synthesis of Compound 6b 2.00 g (6.80 mmol, 1.1 equivalents) of Compound 1a and 1 equivalent of Compound 6a were stirred under a tetrahydrofuran solvent, 2 equivalents of potassium carbonate were dissolved in water, and the resulting solution was added thereto. A reaction was performed under a reflux condition and a nitrogen atmosphere by using 0.05 equivalent of tetrakistriphenylphosphine as a catalyst. After the reaction was terminated, the reactant was cooled to room temperature, and the product was precipitated as a solid by pouring water into the reactant. The produced solid was filtered, and then purified through a column to obtain 2.16 g (yield 67%) of Compound 6b.

2) Synthesis of Compound 6

2.16 g (4.56 mmol, 1 equivalent) of Compound 6b, 1.3 equivalents of Compound 6c, and 3 equivalents of NaOtBu were stirred under a toluene solvent and a nitrogen atmosphere. After the reflux condition was reached, the reaction was performed by using 0.03 equivalent of BTP as a catalyst. After the reaction was terminated, the reactant was cooled to room temperature, and the product was precipitated as a solid by pouring water into the reactant. The produced solid was filtered, and then purified through a column to obtain 2.67 g (yield 78%) of Compound 6.

HR LC/MS/MS m/z calcd for $C_{48}H_{29}F_3N_4S$ (M+): 750.2065; found: 750.2068.

Preparation Example 7. Compound 7
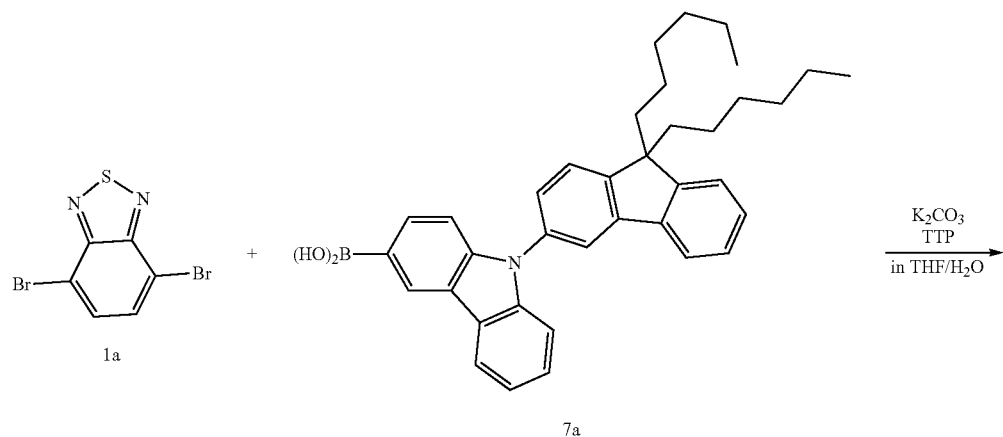
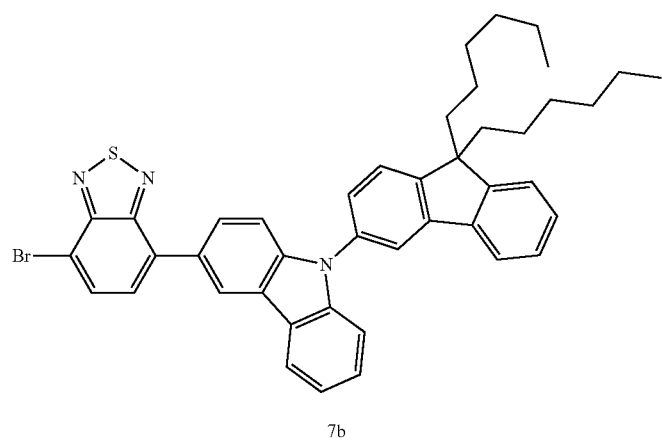
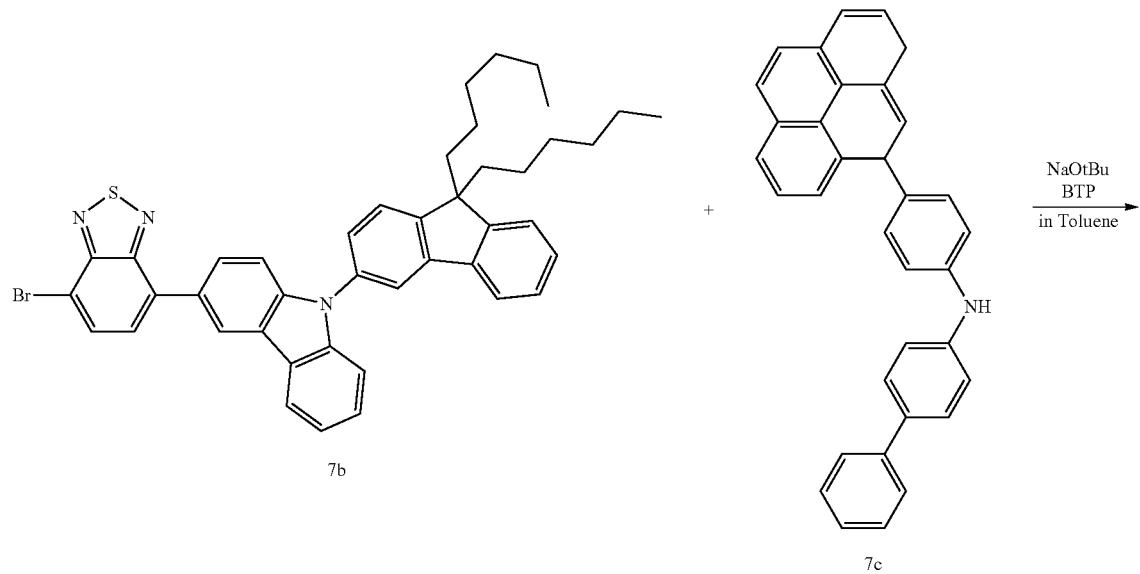

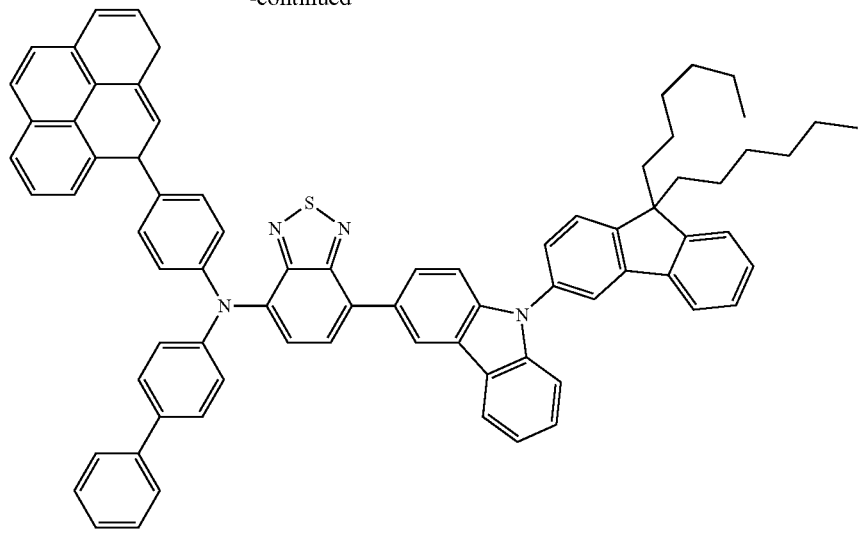

7

1) Synthesis of Compound 7b 2.00 g (6.80 mmol, 1.1 equivalents) of Compound 1a and 1 equivalent of Compound 7a were stirred under a tetrahydrofuran solvent, 2 equivalents of potassium carbonate were dissolved in water, and the resulting solution was added thereto. A reaction was performed under a reflux condition and a nitrogen atmosphere by using 0.05 equivalent of tetrakistriphenylphosphine as a catalyst. After the reaction was terminated, the reactant was cooled to room temperature, and the product was precipitated as a solid by pouring water into the reactant. The produced solid was filtered, and then purified through a column to obtain 3.39 g (yield 70%) of Compound 7b.

2) Synthesis of Compound 7

3.39 g (4.76 mmol, 1 equivalent) of Compound 7b, 1.3 equivalents of Compound 7c, and 3 equivalents of NaOtBu were stirred under a toluene solvent and a nitrogen atmosphere. After the reflux condition was reached, the reaction was performed by using 0.03 equivalent of BTP as a catalyst. After the reaction was terminated, the reactant was cooled to room temperature, and the product was precipitated as a solid by pouring water into the reactant. The produced solid was filtered, and then purified through a column to obtain 4.37 g (yield 85%) of Compound 7.

HR LC/MS/MS m/z calcd for $C_{77}H_{66}N_4S$ (M+): 1078.5008; found: 1078.5007.

Preparation Example 8. Compound 8

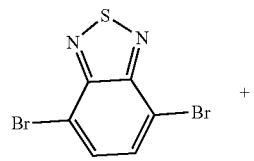

1a

+

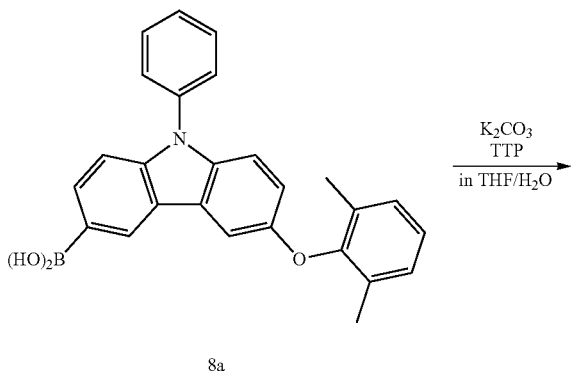

8a $\xrightarrow{\text{K}_2\text{CO}_3 \atop \text{TTP}}$ in THF/H$_2$O

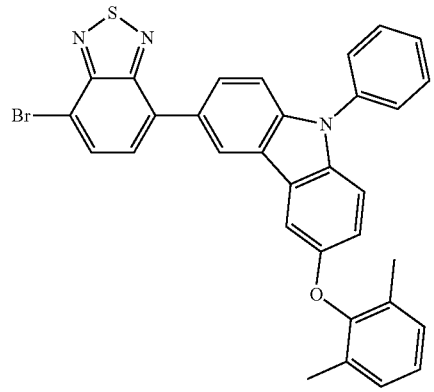

8b

-continued

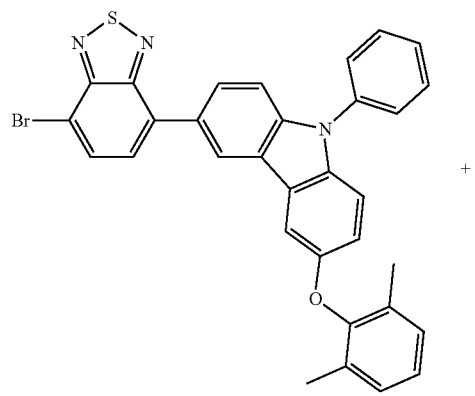

8b

+

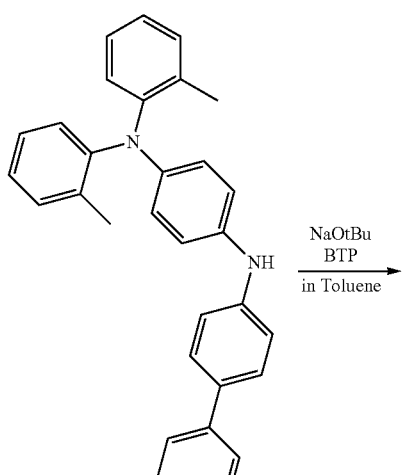

8c

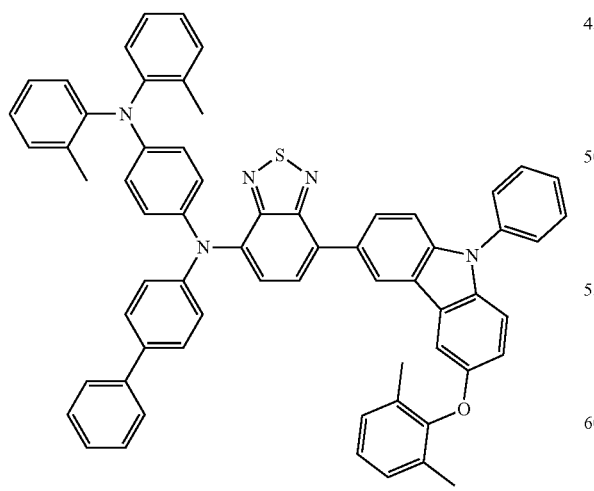

8

1) Synthesis of Compound 8b 2.00 g (6.80 mmol, 1.1 equivalents) of Compound 1a and 1 equivalent of Compound 8a were stirred under a tetrahydrofuran solvent, 2 equivalents of potassium carbonate were dissolved in water, and the resulting solution was added thereto. A reaction was performed under a reflux condition and a nitrogen atmosphere by using 0.05 equivalent of tetrakistriphenylphosphine as a catalyst. After the reaction was terminated, the reactant was cooled to room temperature, and the product was precipitated as a solid by pouring water into the reactant. The produced solid was filtered, and then purified through a column to obtain 2.35 g (yield 60%) of Compound 8b.

2) Synthesis of Compound 8

2.35 g (4.08 mmol, 1 equivalent) of Compound 8b, 1.3 equivalents of Compound 8c, and 3 equivalents of NaOtBu were stirred under a toluene solvent and a nitrogen atmosphere. After the reflux condition was reached, the reaction was performed by using 0.03 equivalent of BTP as a catalyst. After the reaction was terminated, the reactant was cooled to room temperature, and the product was precipitated as a solid by pouring water into the reactant. The produced solid was filtered, and then purified through a column to obtain 2.48 g (yield 65%) of Compound 8.

HR LC/MS/MS m/z calcd for $C_{64}H_{49}N_5OS$ (M+): 935.3658; found: 935.3653.

Preparation Example 9. Compound 9

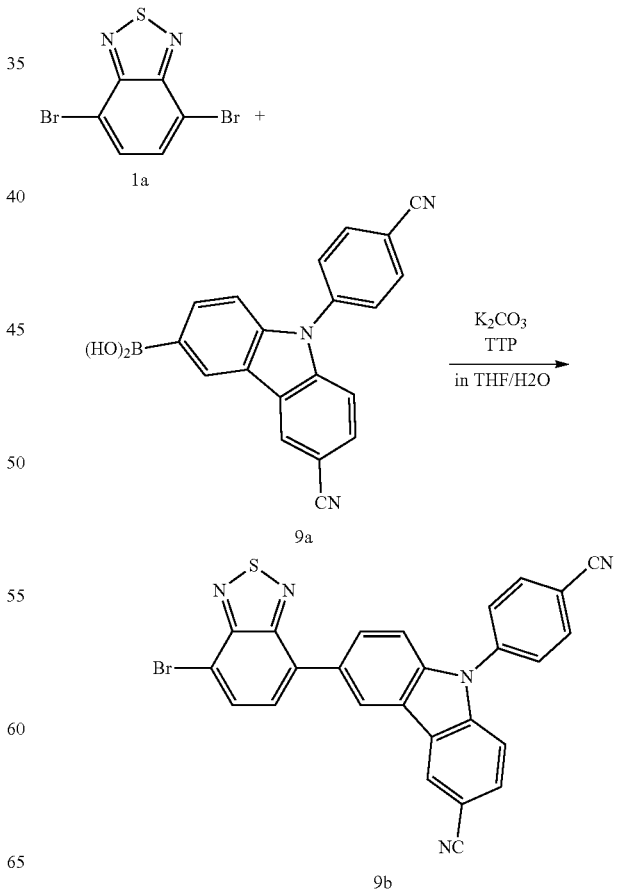

-continued

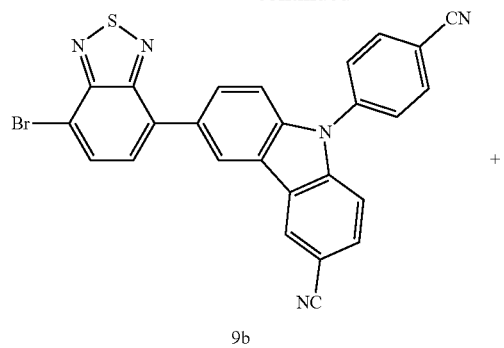

9b

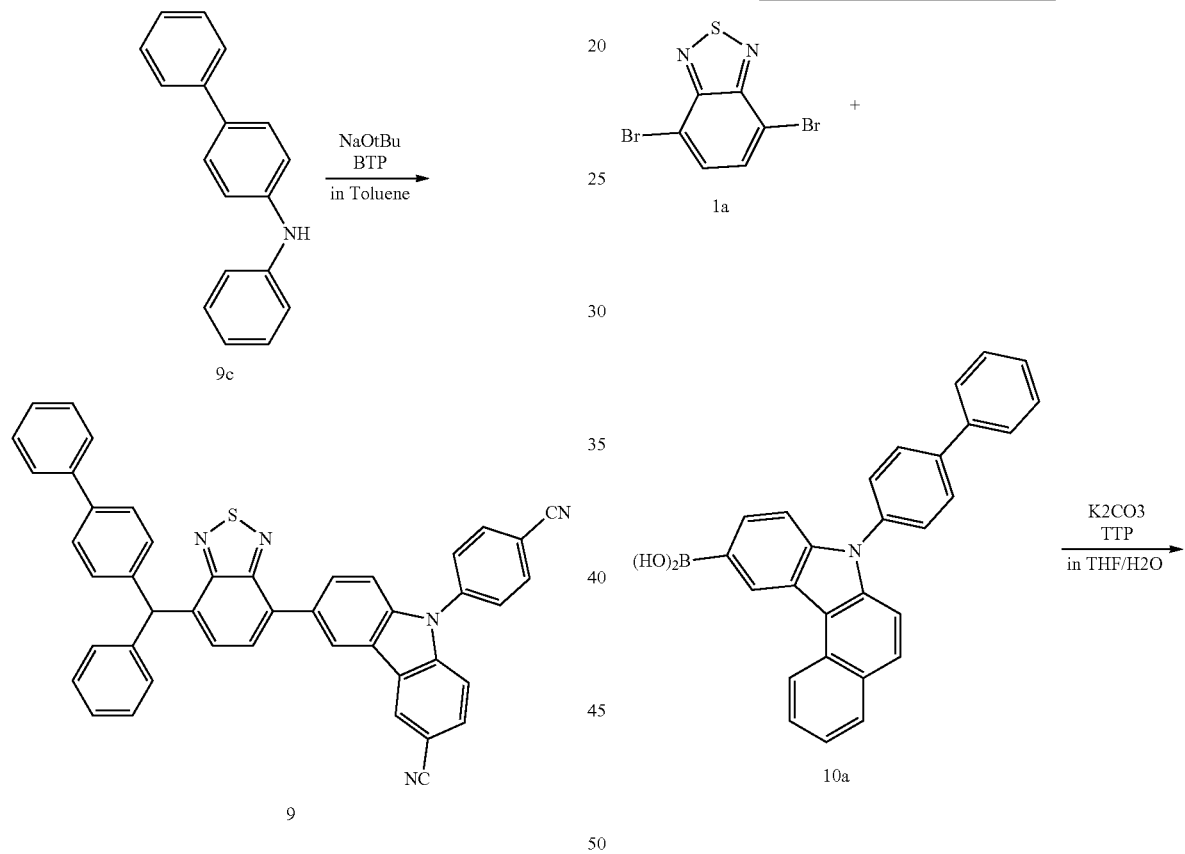

1) Synthesis of Compound 9b 2.00 g (6.80 mmol, 1.1 equivalents) of Compound 1a and 1 equivalent of Compound 9a were stirred under a tetrahydrofuran solvent, 2 equivalents of potassium carbonate were dissolved in water, and the resulting solution was added thereto. A reaction was performed under a reflux condition and a nitrogen atmosphere by using 0.05 equivalent of tetrakistriphenylphosphine as a catalyst. After the reaction was terminated, the reactant was cooled to room temperature, and a solid was precipitated by pouring water into the reactant. The produced solid was filtered, and then purified through a column to obtain 2.65 g (yield 77%) of Compound 9b.

2) Synthesis of Compound 9

2.65 g (5.24 mmol, 1 equivalent) of Compound 9b, 1.3 equivalents of Compound 9c, and 3 equivalents of NaOtBu were stirred under a toluene solvent and a nitrogen atmosphere. After the reflux condition was reached, the reaction was performed by using 0.03 equivalent of BTP as a catalyst. After the reaction was terminated, the reactant was cooled to room temperature, and the product was precipitated as a solid by pouring water into the reactant. The produced solid was filtered, and then purified through a column to obtain 2.95 g (yield 84%) of Compound 9.

HR LC/MS/MS m/z calcd for $C_{44}H_{26}N_6S$ (M+): 670.1940; found: 670.1936.

Preparation Example 10. Compound 10

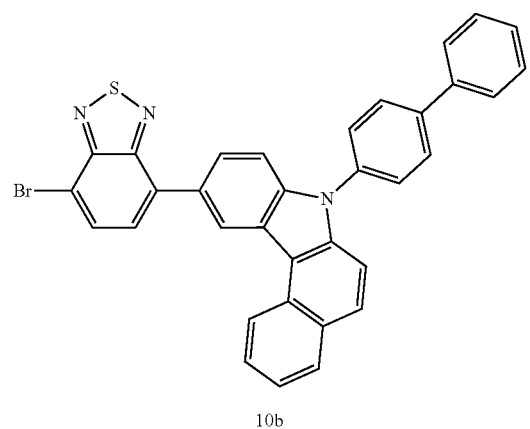

-continued

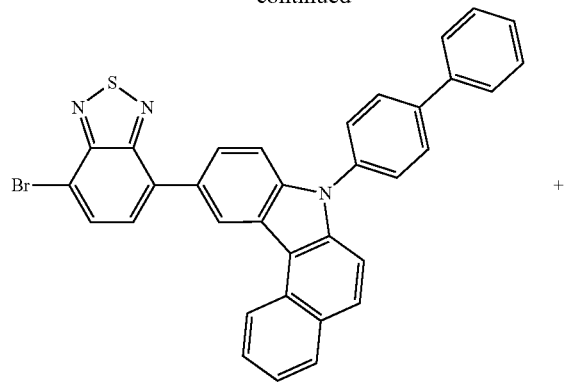

10b

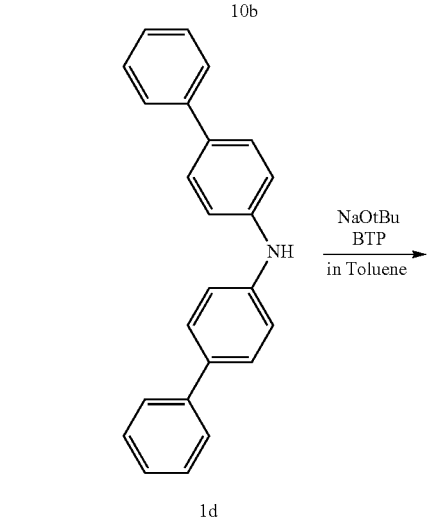

10

1) Synthesis of Compound 10b 2.00 g (6.80 mmol, 1.1 equivalents) of Compound 1a and 1 equivalent of Compound 10a were stirred under a tetrahydrofuran solvent, 2 equivalents of potassium carbonate were dissolved in water, and the resulting solution was added thereto. A reaction was performed under a reflux condition and a nitrogen atmosphere by using 0.05 equivalent of tetrakistriphenylphosphine as a catalyst. After the reaction was terminated, the reactant was cooled to room temperature, and the product was precipitated as a solid by pouring water into the reactant. The produced solid was filtered, and then purified through a column to obtain 3.01 g (yield 76%) of Compound 10b.

2) Synthesis of Compound 10

3.01 g (5.17 mmol, 1 equivalent) of Compound 10b, 1.3 equivalents of Compound 1d, and 3 equivalents of NaOtBu were stirred under a toluene solvent and a nitrogen atmosphere. After the reflux condition was reached, the reaction was performed by using 0.03 equivalent of BTP as a catalyst. After the reaction was terminated, the reactant was cooled to room temperature, and the product was precipitated as a solid by pouring water into the reactant. The produced solid was filtered, and then purified through a column to obtain 3.79 g (yield 89%) of Compound 10.

HR LC/MS/MS m/z calcd for $C_{58}H_{38}N_4S$ (M+): 822.2817; found: 822.2815.

Preparation Example 11. Compound 11

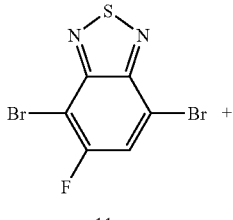

11a

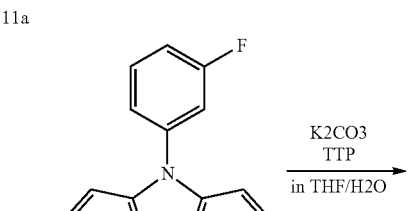

11b

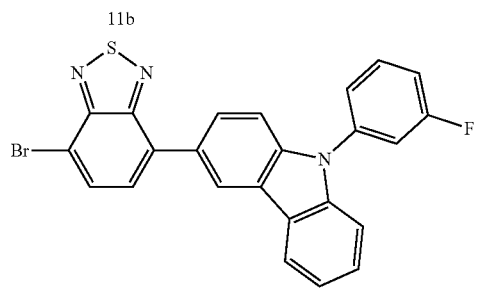

11c

-continued

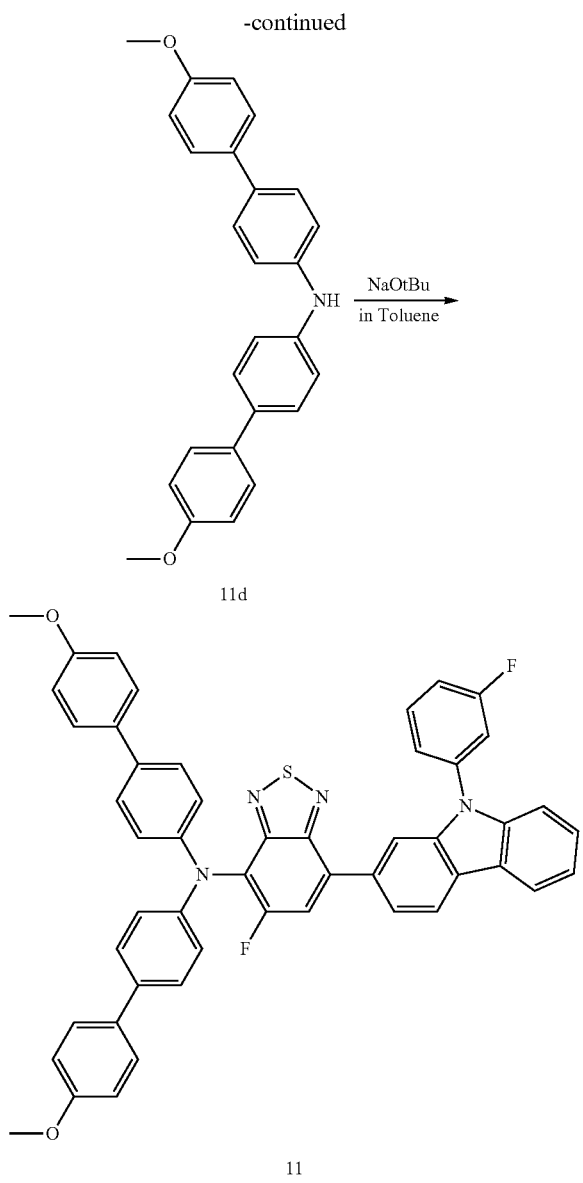

1) Synthesis of Compound 11c 2.00 g (6.80 mmol, 1.1 equivalents) of Compound 1a and 1 equivalent of Compound 11b were stirred under a tetrahydrofuran solvent, 2 equivalents of potassium carbonate were dissolved in water, and the resulting solution was added thereto. A reaction was performed under a reflux condition and a nitrogen atmosphere by using 0.05 equivalent of tetrakistriphenylphosphine as a catalyst. After the reaction was terminated, the reactant was cooled to room temperature, and the product was precipitated as a solid by pouring water into the reactant. The produced solid was filtered, and then purified through a column to obtain 2.03 g (yield 63%) of Compound 11c.

2) Synthesis of Compound 11

2.03 g (4.28 mmol, 1 equivalent) of Compound 11c, 1.3 equivalents of Compound 11d, and 3 equivalents of NaOtBu were stirred under a toluene solvent and a nitrogen atmosphere. After the reflux condition was reached, the reaction was performed by using 0.03 equivalent of BTP as a catalyst. After the reaction was terminated, the reactant was cooled to room temperature, and the product was precipitated as a solid by pouring water into the reactant. The produced solid was filtered, and then purified through a column to obtain 2.38 g (yield 70%) of Compound 11.

HR LC/MS/MS m/z calcd for $C_{50}H_{34}F_2N_4O_2S$ (M+): 792.2371; found: 792.2365.

Preparation Example 12. Compound 12

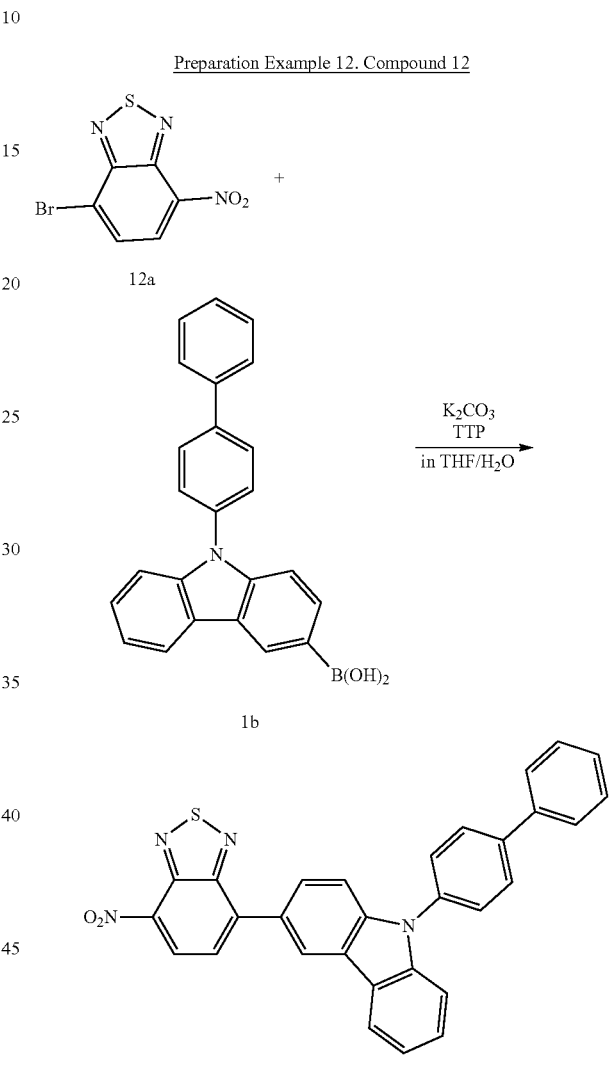

1) Synthesis of Compound 12

2.00 g (7.69 mmol, 1 equivalent) of Compound 12a and 1.2 equivalents of Compound 1b were stirred under a tetrahydrofuran solvent, 2 equivalents of potassium carbonate were dissolved in water, and the resulting solution was added thereto. A reaction was performed under a reflux condition and a nitrogen atmosphere by using 0.05 equivalent of tetrakistriphenylphosphine as a catalyst. After the reaction was terminated, the reactant was cooled to room temperature, and the product was precipitated as a solid by pouring water into the reactant. The produced solid was filtered, and then purified through a column to obtain 3.64 g (yield 95%) of Compound 12.

HR LC/MS/MS m/z calcd for $C_{30}H_{18}N_4O_2S$ (M+): 498.1150; found: 498.1152.

Physical properties of Compounds 1 to 12 are as shown in the following Table 1.

TABLE 1

| Compound No. | Solution Abs. (nm) | Solution PL (nm) | Q.E. (%) |
| --- | --- | --- | --- |
| 1 | 497 | 616 | 84 |
| 2 | 498 | 624 | 103 |
| 3 | 495 | 613 | 82 |
| 4 | 503 | 628 | 31 |
| 5 | 498 | 618 | 85 |
| 6 | 494 | 614 | 79 |
| 7 | 499 | 617 | 75 |
| 8 | 498 | 620 | 77 |
| 9 | 494 | 613 | 81 |
| 10 | 513 | 640 | 28 |
| 11 | 475 | 589 | 83 |
| 12 | 450 | — | — |

The physical properties were measured after each of the compounds was prepared at a concentration of $10^{-5}$ M under a toluene solvent.

Absorbance, photoluminescence, and quantum efficiency were abbreviated as Abs., PL, and Q.E., respectively. In the table, the numerical values of 'Solution Abs.' and 'Solution PL' indicate the wavelength values at the maximum intensity.

The Abs. was measured by using MEGA-2100 equipment manufactured by SCINCO Co., Ltd., and the PL was measured by using FS-2 equipment manufactured by SCINCO Co., Ltd.

EXAMPLES

Example 1

1.5 parts by weight of Compound 1 (maximum absorption wavelength of 497 nm and maximum light emission wavelength of 616 nm in a toluene solution) prepared in Preparation Example 1 was dissolved in a solvent propylene glycol monomethyl ether acetate (PGMEA), such that 33.9 parts by weight of an acrylic binder, 59.3 parts by weight of a polyfunctional monomer (pentaerythritol triacrylate, Nippon Kayaku Co., Ltd.), 2.3 parts by weight of a bonding aid and a surfactant (KBM 503, Shinetsu), and 3.0 parts by weight of a photoinitiator (Tinuvin® 477, BASF) had a solid content of 21 wt %, thereby preparing a solution. After the mixed solution was sufficiently stirred, a glass substrate was coated with a thin film, and then the thin film was dried to prepare a color conversion film. The brightness spectrum of the prepared color conversion film was measured by a spectroradiometer (SR series manufactured by Topcon, Inc.). Specifically, the prepared color conversion film was stacked on one surface of a light guide plate of a backlight unit including an LED blue backlight (maximum light emission wavelength of 450 nm) and the light guide plate, a prism sheet and a DBEF film were stacked on the color conversion film, and then an initial value was set, such that the luminance of the blue LED light was 600 nit based on the film.

Example 2

A color conversion film was prepared in the same manner as in the above-described Example 1, except that in Example 1, Compound 2 (maximum absorption wavelength of 498 nm and maximum light emission wavelength of 624 nm in a toluene solution) was used instead of Compound 1.

Example 3

A color conversion film was prepared in the same manner as in the above-described Example 1, except that in Example 1, Compound 3 (maximum absorption wavelength of 495 nm and maximum light emission wavelength of 613 nm in a toluene solution) was used instead of Compound 1.

Example 4

A color conversion film was prepared in the same manner as in the above-described Example 1, except that in Example 1, Compound 5 (maximum absorption wavelength of 498 nm and maximum light emission wavelength of 618 nm in a toluene solution) was used instead of Compound 1.

Example 5

A color conversion film was prepared in the same manner as in the above-described Example 1, except that in Example 1, Compound 6 (maximum absorption wavelength of 494 nm and maximum light emission wavelength of 614 nm in a toluene solution) was used instead of Compound 1.

Example 6

A color conversion film was prepared in the same manner as in the above-described Example 1, except that in Example 1, Compound 9 (maximum absorption wavelength of 494 nm and maximum light emission wavelength of 613 nm in a toluene solution) was used instead of Compound 1.

Example 7

A color conversion film was prepared in the same manner as in the above-described Example 1, except that in Example 1, Compound 10 (maximum absorption wavelength of 513 nm and maximum light emission wavelength of 640 nm in a toluene solution) was used instead of Compound 1.

Example 8

A color conversion film was prepared in the same manner as in the above-described Example 1, except that in Example 1, Compound 11 (maximum absorption wavelength of 475 nm and maximum light emission wavelength of 589 nm in a toluene solution) was used instead of Compound 1.

Comparative Example

A color conversion film was prepared in the same manner as in the above-described Example 1, except that in Example 1, Compound 12 (maximum absorption wavelength of 450 nm in a toluene solution) was used instead of Compound 1.

The thin film light emission wavelength and thin film quantum efficiency (PLQY (%)) of each of the color conversion films according to Examples 1 to 8 and the Comparative Example are as shown in the following Table 2.

TABLE 2
| Example | Preparation Example | Example | Thin film light emission wavelength $\lambda_{PL.max}$ (nm) | Thin film quantum efficiency (PLQY (%)) |
|---|---|---|---|---|
| 1 | 1 | 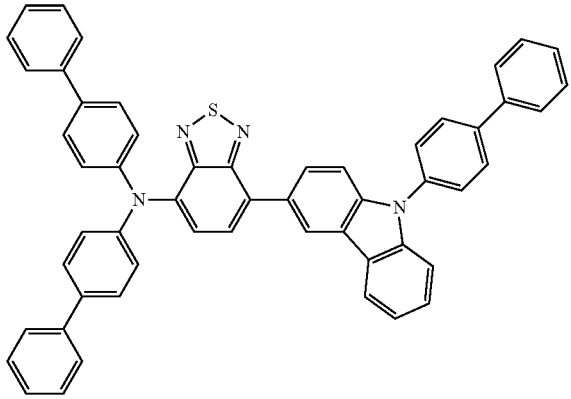 [SMILES: c1ccc(-c2ccc(N(c3ccc(-c4ccccc4)cc3)c3ccc(-c4ccc5c(c4)c4ccccc4n5-c4ccc(-c5ccccc5)cc4)c4nsnc34)cc2)cc1] | 641 | 59.5 |
| 2 | 2 | 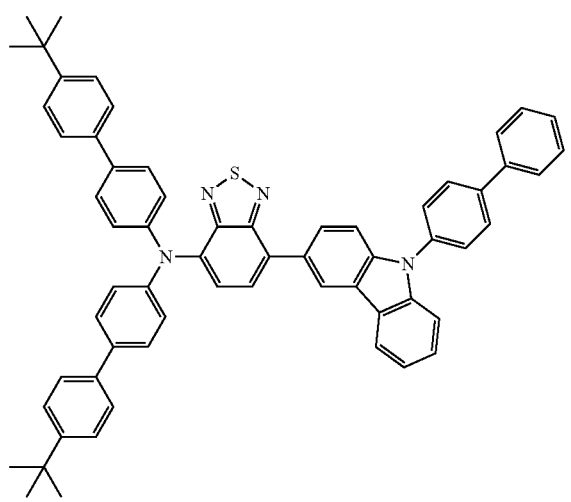 [SMILES: CC(C)(C)c1ccc(-c2ccc(N(c3ccc(-c4ccc(C(C)(C)C)cc4)cc3)c3ccc(-c4ccc5c(c4)c4ccccc4n5-c4ccc(-c5ccccc5)cc4)c4nsnc34)cc2)cc1] | 625 | 48.7 |
| 3 | 3 | 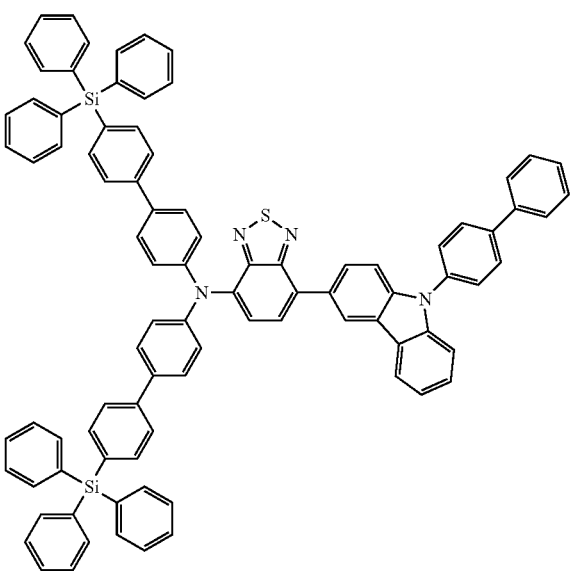 [SMILES: c1ccc(-c2ccc(-n3c4ccccc4c4cc(-c5ccc(N(c6ccc(-c7ccc([Si](c8ccccc8)(c8ccccc8)c8ccccc8)cc7)cc6)c6ccc(-c7ccc([Si](c8ccccc8)(c8ccccc8)c8ccccc8)cc7)cc6)c6nsnc56)ccc43)cc2)cc1] | 620 | 62.5 |

TABLE 2-continued
| Example | Preparation Example | Example | Thin film light emission wavelength $\lambda_{PL.max}$ (nm) | Thin film quantum efficiency (PLQY (%)) |
|---|---|---|---|---|
| 4 | 5 | 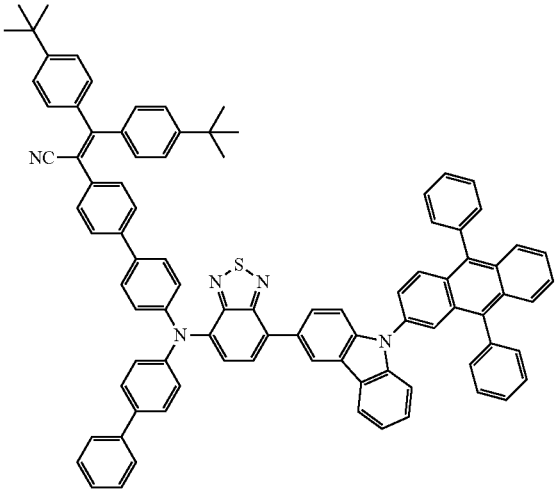 [SMILES: CC(C)(C)c1ccc(C(=C(C#N)c2ccc(-c3ccc(N(c4ccc(-c5ccccc5)cc4)c4ccc(-c5ccc6c(c5)c5ccccc5n6-c5ccc6c(-c7ccccc7)c7ccccc7c(-c7ccccc7)c6c5)c5nsnc45)cc3)cc2)c2ccc(C(C)(C)C)cc2)cc1] | 629 | 60.5 |
| 5 | 6 | 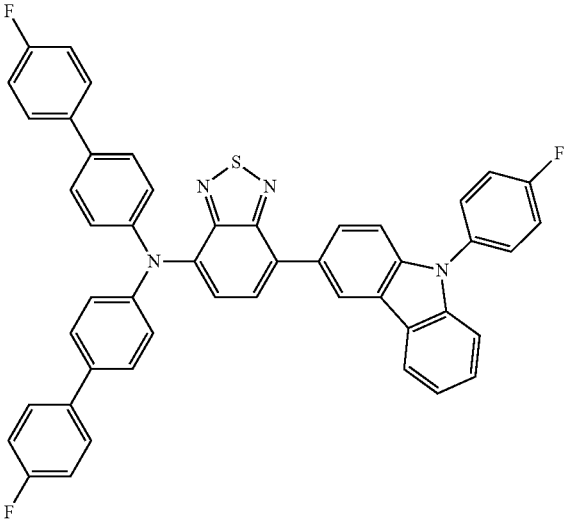 [SMILES: Fc1ccc(-c2ccc(N(c3ccc(-c4ccc(F)cc4)cc3)c3ccc(-c4ccc5c(c4)c4ccccc4n5-c4ccc(F)cc4)c4nsnc34)cc2)cc1] | 627 | 51.3 |
| 6 | 9 | 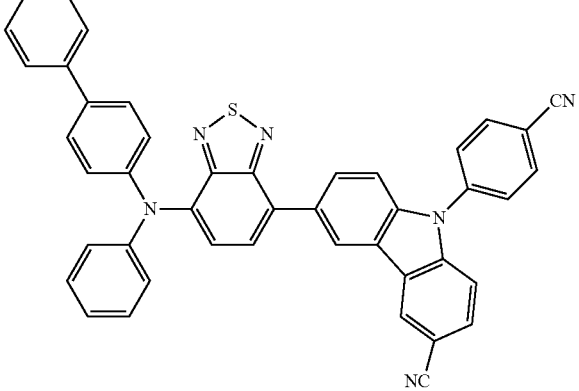 | 624 | 44.1 |

TABLE 2-continued
| Example | Preparation Example | Example | Thin film light emission wavelength $\lambda_{PL.max}$ (nm) | Thin film quantum efficiency (PLQY (%)) |
|---|---|---|---|---|
| 7 | 10 | 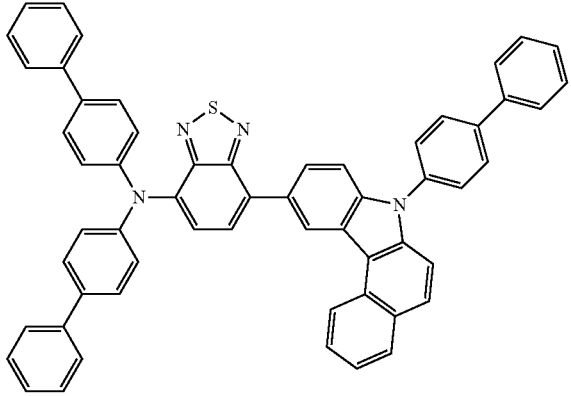 [SMILES: c1ccc(-c2ccc(N(c3ccc(-c4ccccc4)cc3)c3ccc(-c4ccc5c(c4)c4c6ccccc6ccc4n5-c4ccc(-c5ccccc5)cc4)c4nsnc34)cc2)cc1] | 659 | 32.0 |
| 8 | 11 | 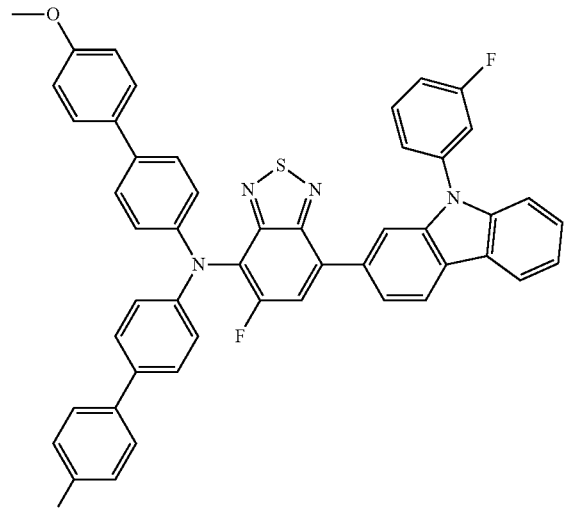 | 599 | 52.6 |
| Comparative Example | 12 | 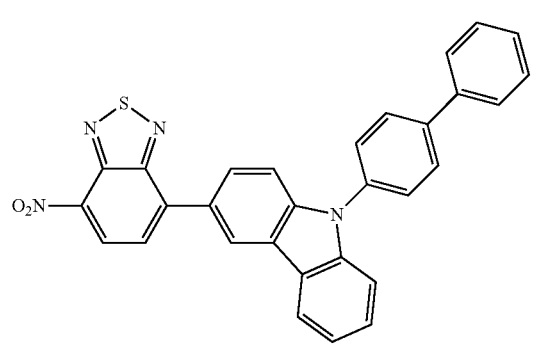 [SMILES: O=[N+]([O-])c1ccc(-c2ccc3c(c2)c2ccccc2n3-c2ccc(-c3ccccc3)cc2)c2nsnc12] | 613 | 21.3 |

The thin film light emission wavelength was measured by using FS-2 equipment manufactured by SCINCO Co., Ltd., and the thin film quantum efficiency was measured by using Quantaurus-QY equipment manufactured by Hamamatsu Corp.

As confirmed in Table 2, it could be confirmed that the color conversion films manufactured in Examples 1 to 8 could synthesize various phosphors at a longer wavelength and had better thin film quantum efficiencies than that of the color conversion film manufactured through the Comparative Example.

The invention claimed is:

1. A compound represented by the following Formula 1:

[Formula 1]

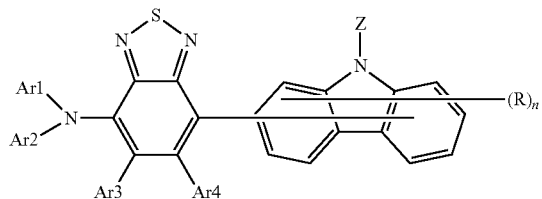

wherein
Ar1 and Ar2 are the same as or different from each other, and are each independently a substituted or unsubstituted aryl group having 6 to 30 carbon atoms, wherein at least one of Ar1 and Ar2 is a substituted aryl group,
Ar3 and Ar4 are the same as or different from each other, and are each independently hydrogen, deuterium, or a halogen group,
Z is a substituted or unsubstituted aryl group; or a substituted or unsubstituted heteroaryl group,
R is hydrogen; deuterium; a halogen group; a cyano group; a nitro group; a carbonyl group; a carboxyl group (—COOH); an ether group; a hydroxyl group; a substituted or unsubstituted alkyl group; a substituted or unsubstituted aryl group; a substituted or unsubstituted alkoxy group; a substituted or unsubstituted aryloxy group; a substituted or unsubstituted alkenyl group; or —C(=O)ORa, or adjacent substituents are optionally bonded to each other to form a ring which is unsubstituted or substituted with a substituted or unsubstituted aryl group, and Ra is a substituted or unsubstituted alkyl group, and
n is an integer from 0 to 7.

2. The compound of claim 1, wherein the at least one of Ar1 and Ar2 is substituted with at least one group selected from the group of fluorine, a nitro group, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted silyl group, a substituted or unsubstituted alkoxy group having 1 to 30 carbon atoms, a substituted or unsubstituted aryloxy group, a substituted or unsubstituted amine group having 1 to 30 carbon atoms, a substituted or unsubstituted aryl group having 6 to 30 carbon atoms, and a substituted or unsubstituted heteroaryl group having 2 to 30 carbon atoms.

3. The compound of claim 1, wherein Z is an aryl group having 6 to 30 carbon atoms, which is unsubstituted or substituted with one or more selected from the group consisting of a halogen group, a cyano group, a silyl group, a carboxyl group (COOH), a substituted or unsubstituted alkyl group, a substituted or unsubstituted alkenyl group, a substituted or unsubstituted alkoxy group, a substituted or unsubstituted cycloalkyl group, a substituted or unsubstituted sulfonyl group, a substituted or unsubstituted aryloxy group, and a substituted or unsubstituted aryl group; or a heteroaryl group having 2 to 30 carbon atoms, which is unsubstituted or substituted with at least one group selected from the group of an alkyl group and an aryl group.

4. The compound of claim 1, wherein R is hydrogen; deuterium; a halogen group; a cyano group; an alkyl group having 1 to 50 carbon atoms; an alkoxy group having 1 to 30 carbon atoms, which is substituted with a heteroaryl group; an aryl group having 6 to 30 carbon atoms, which is unsubstituted or substituted with a halogen group, an alkyl group substituted with an aryl group, or a fluoroalkyl group; or —C(=O)ORa, or adjacent substituents are optionally bonded to each other to form a ring having 3 to 30 carbon atoms, which is unsubstituted or substituted with an aryl group which is unsubstituted or substituted with an alkyl group or a substituted or unsubstituted alkenyl group, or a dihydroanthracene group substituted with an alkyl group, and Ra is an alkyl group which is unsubstituted or substituted with an aryl group.

5. The compound of claim 1, wherein the compound of Formula 1 is represented by any one of the following structural formulae:

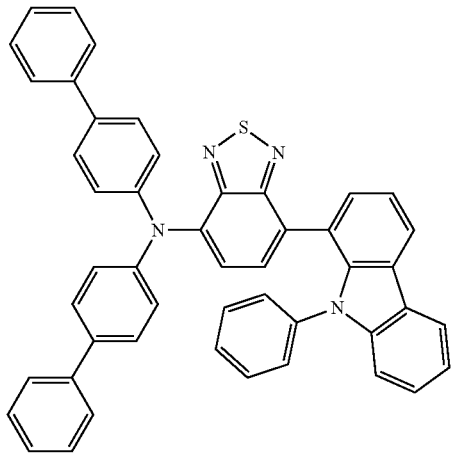

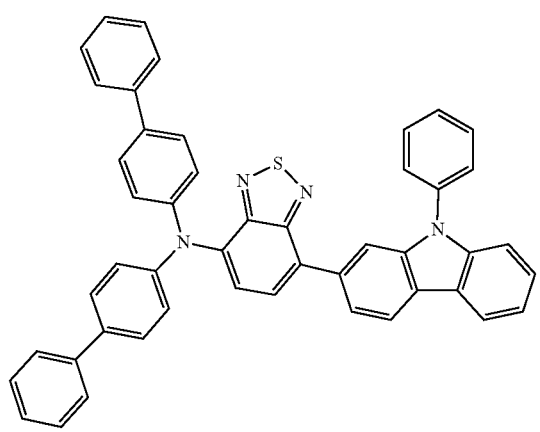

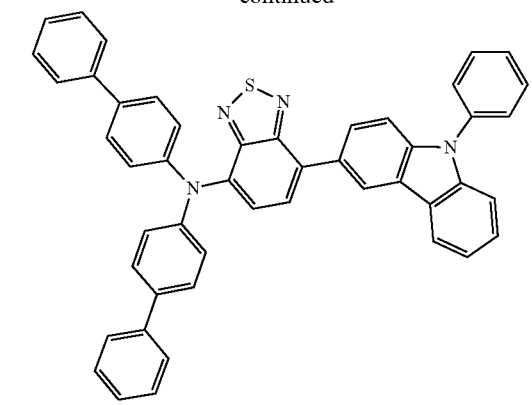
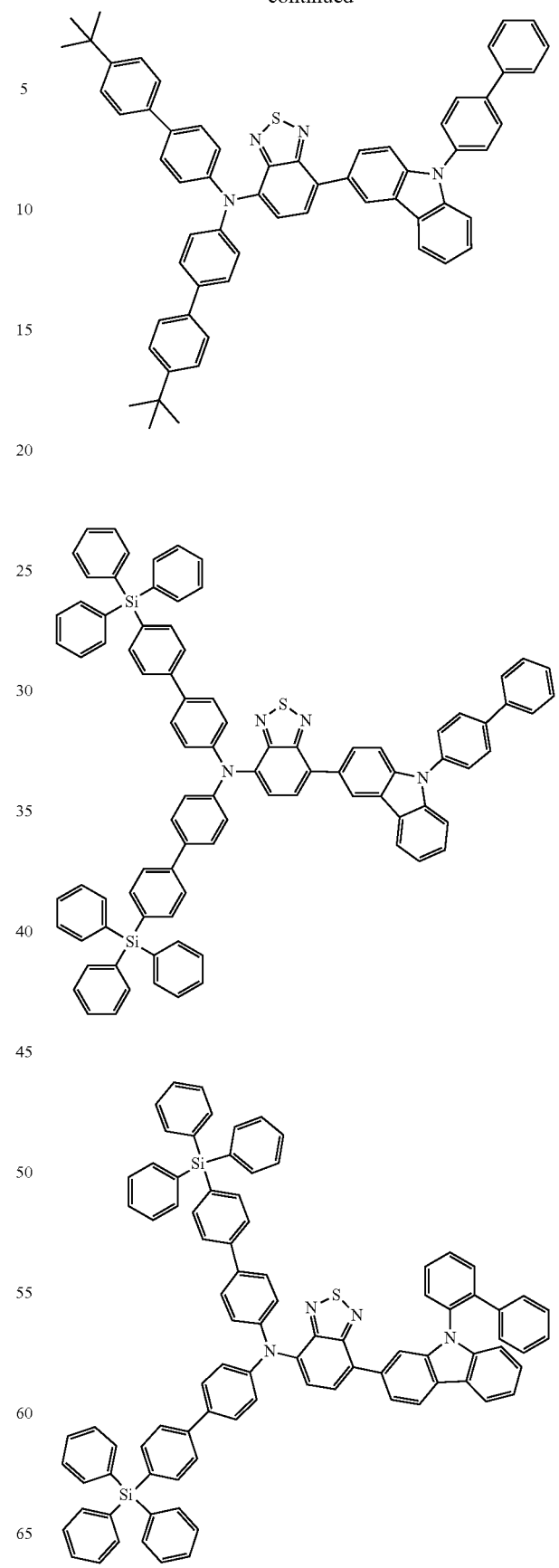

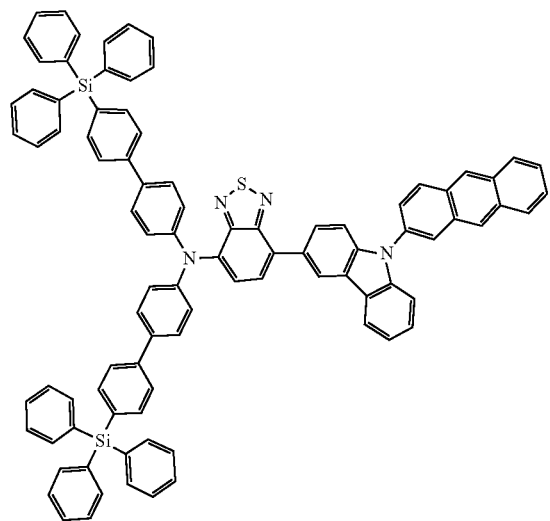
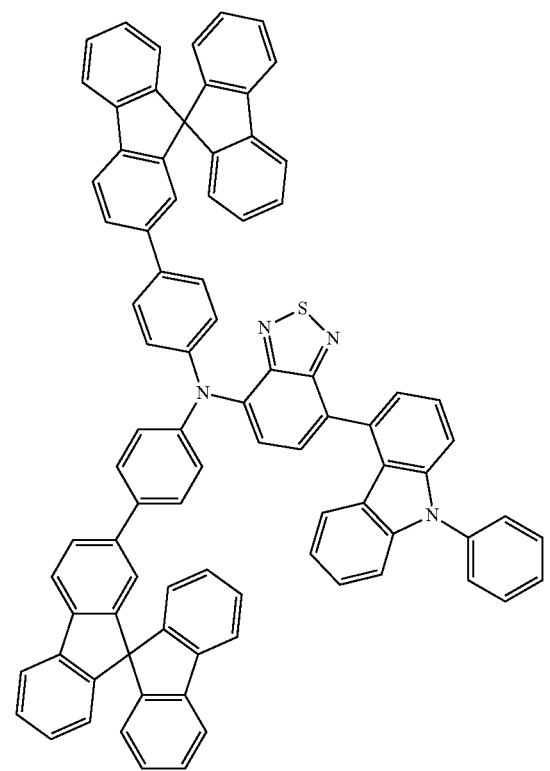
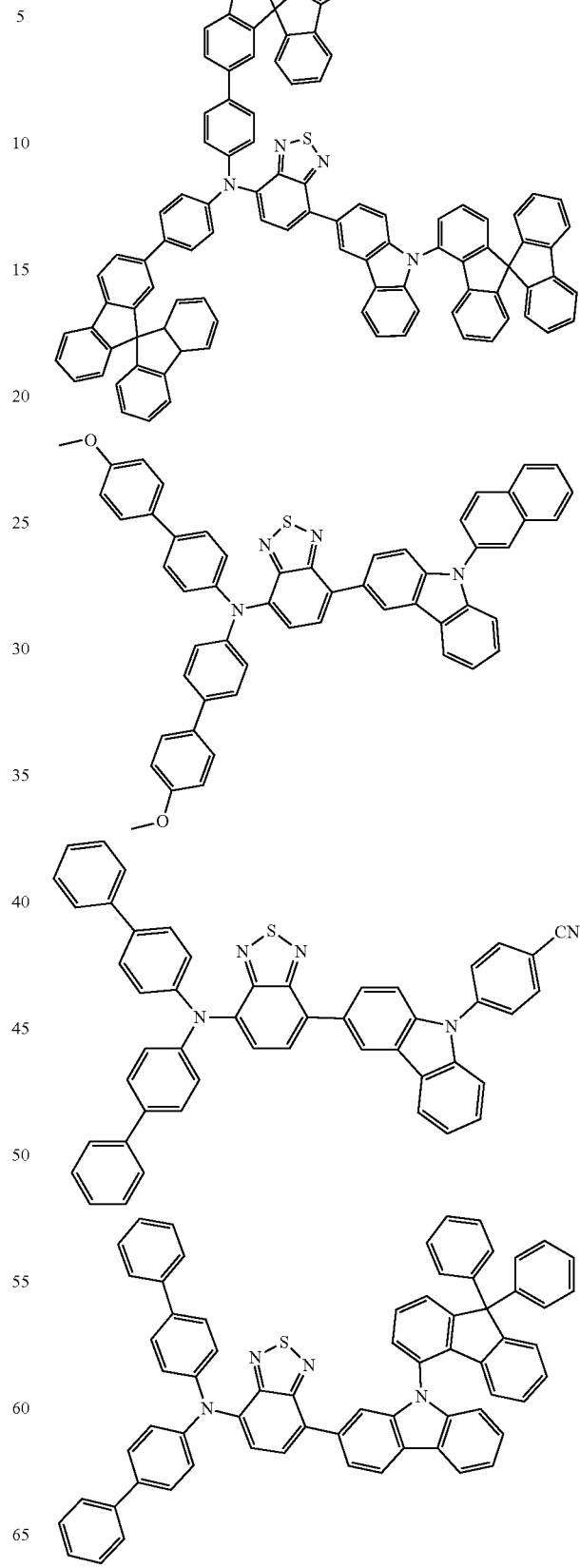

107
-continued
108
-continued
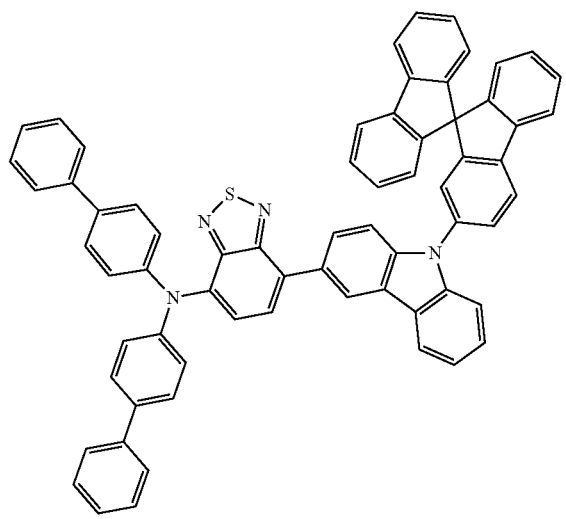
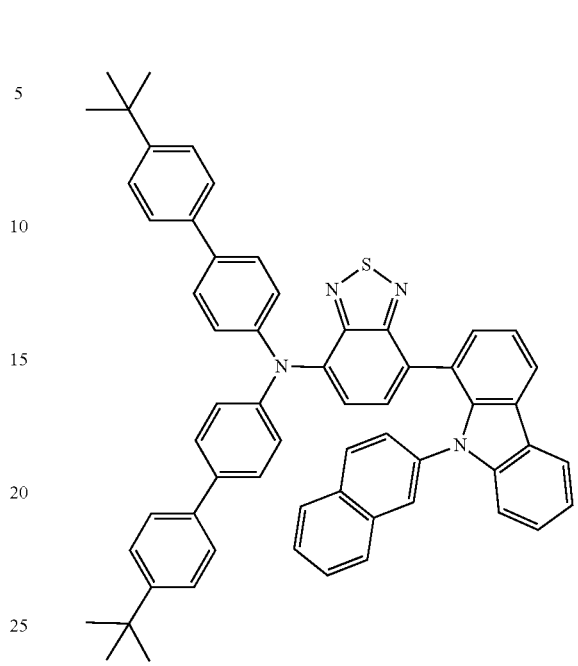
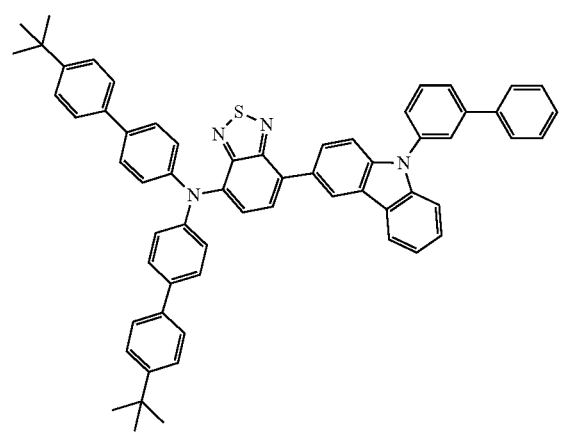
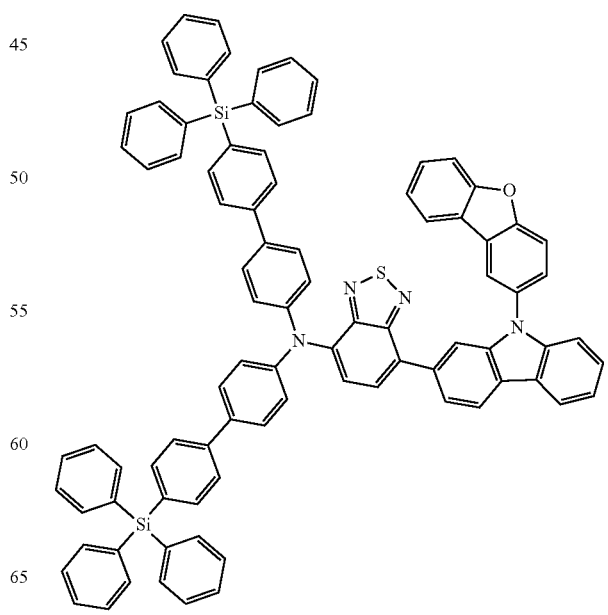

109
-continued
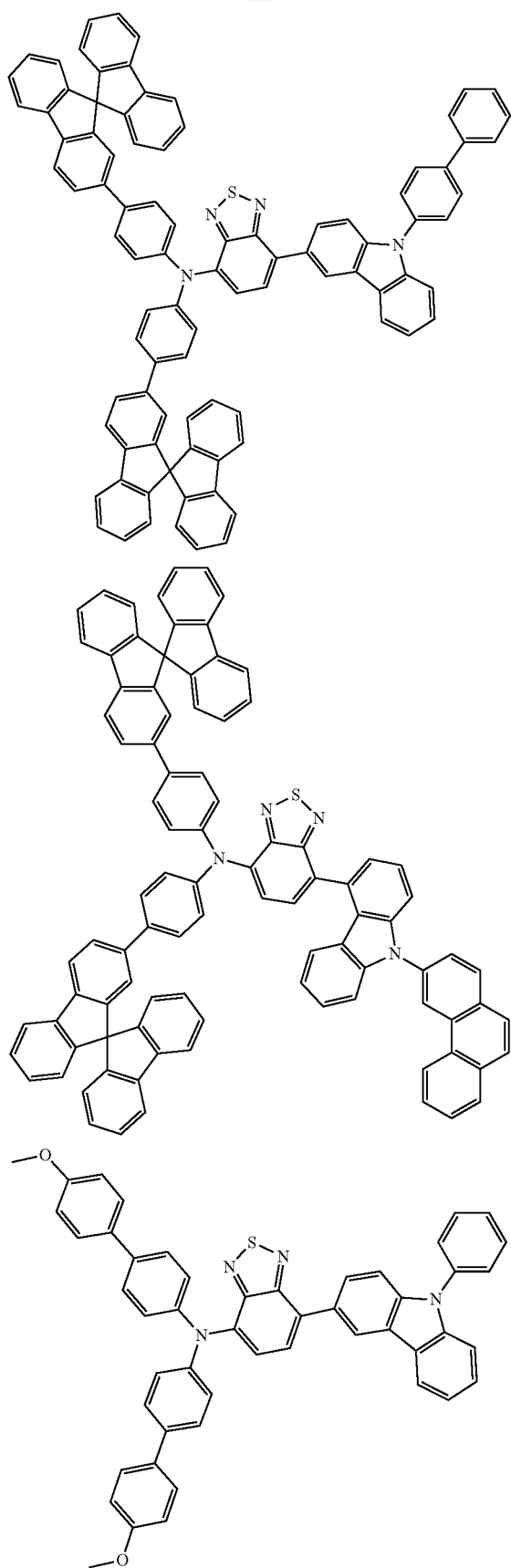
110
-continued
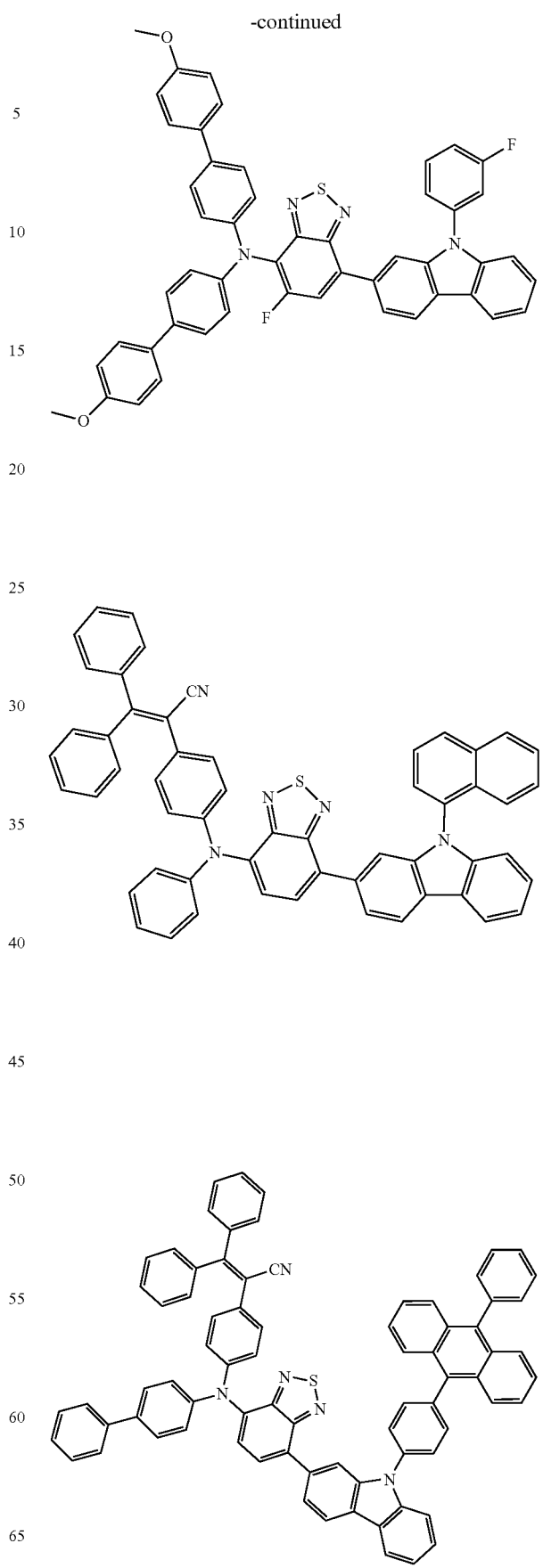

111
-continued
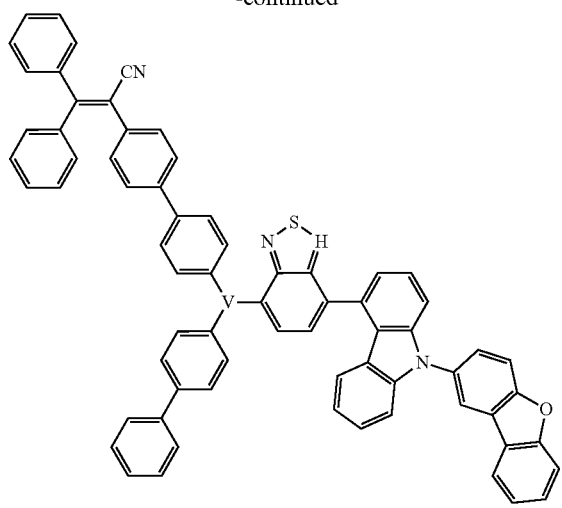
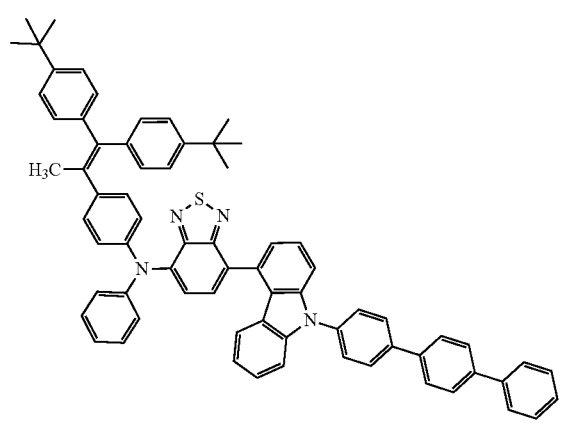
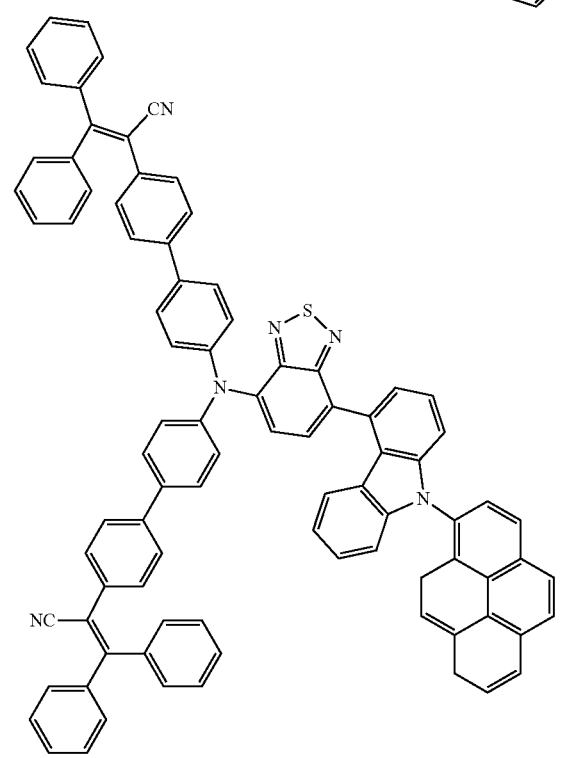
112
-continued
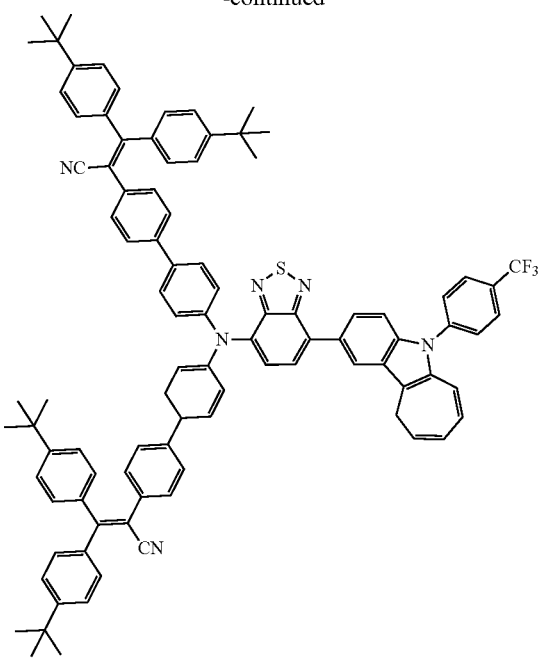
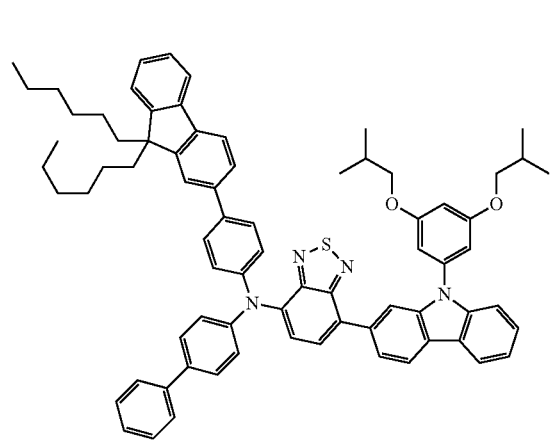
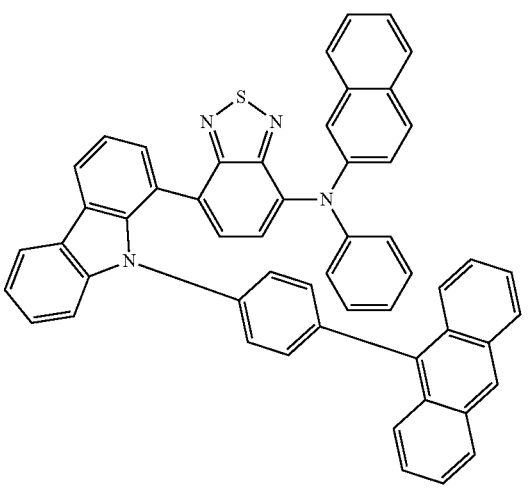

113
-continued
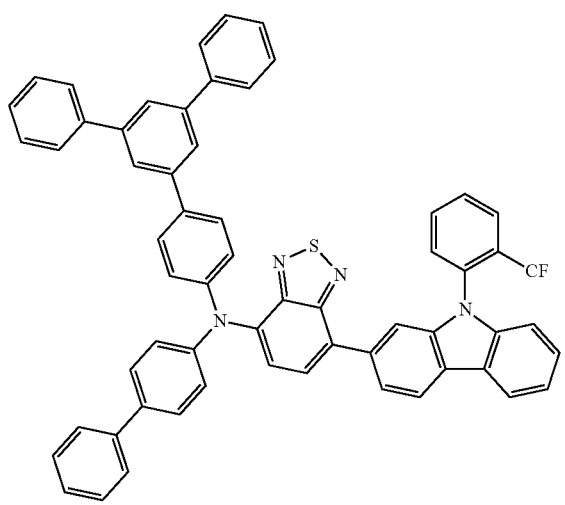
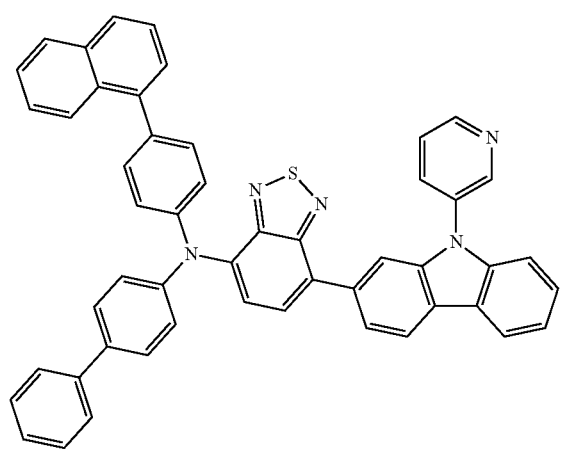
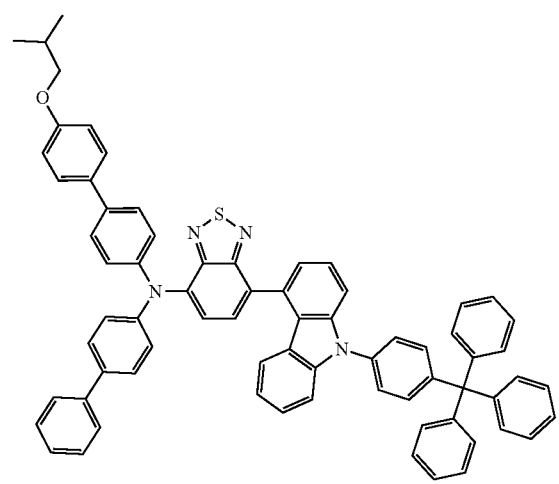
114
-continued
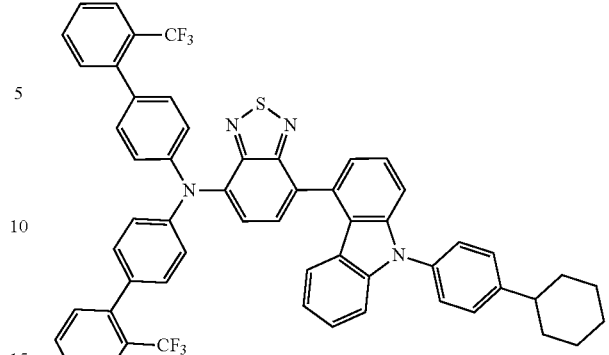
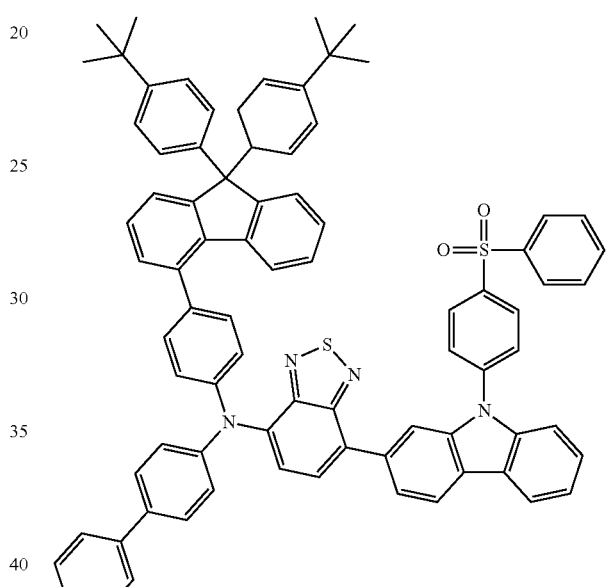
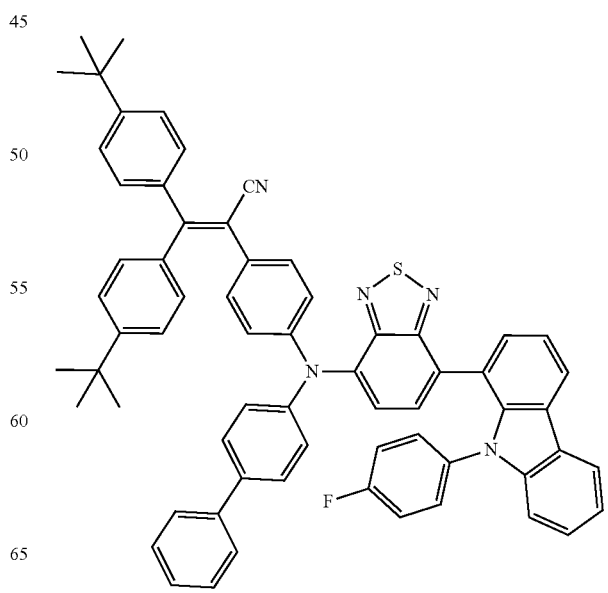

115
-continued
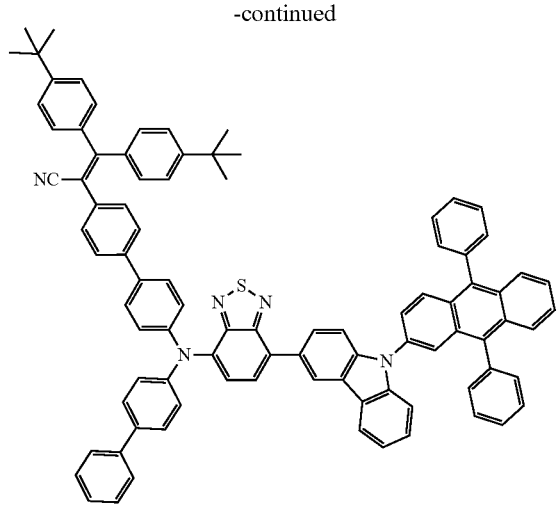
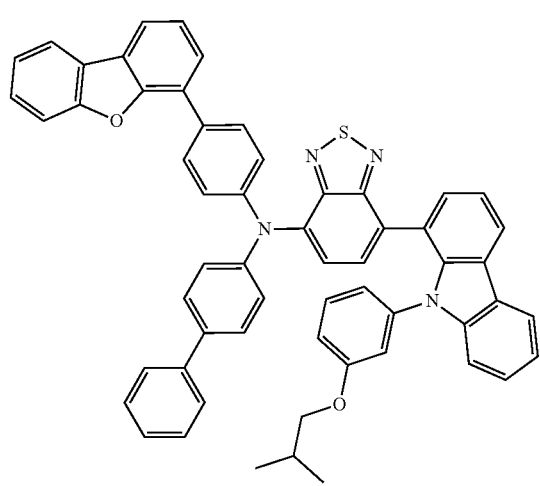
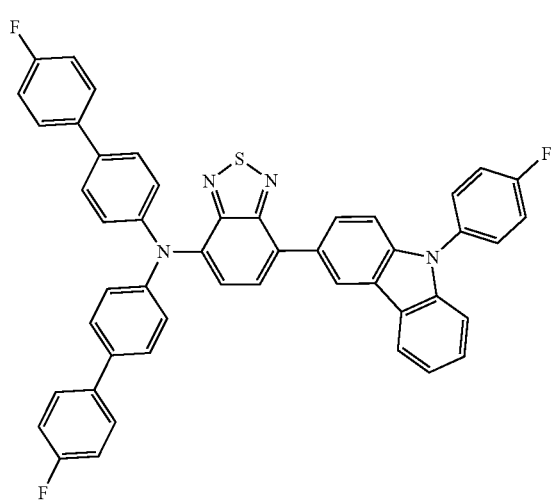
116
-continued
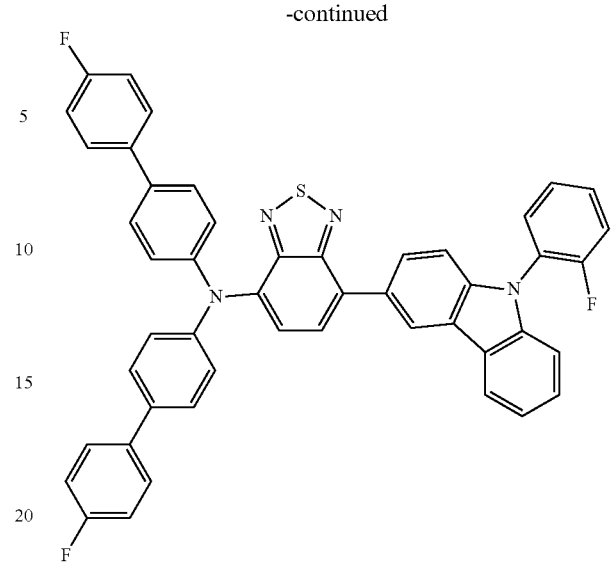
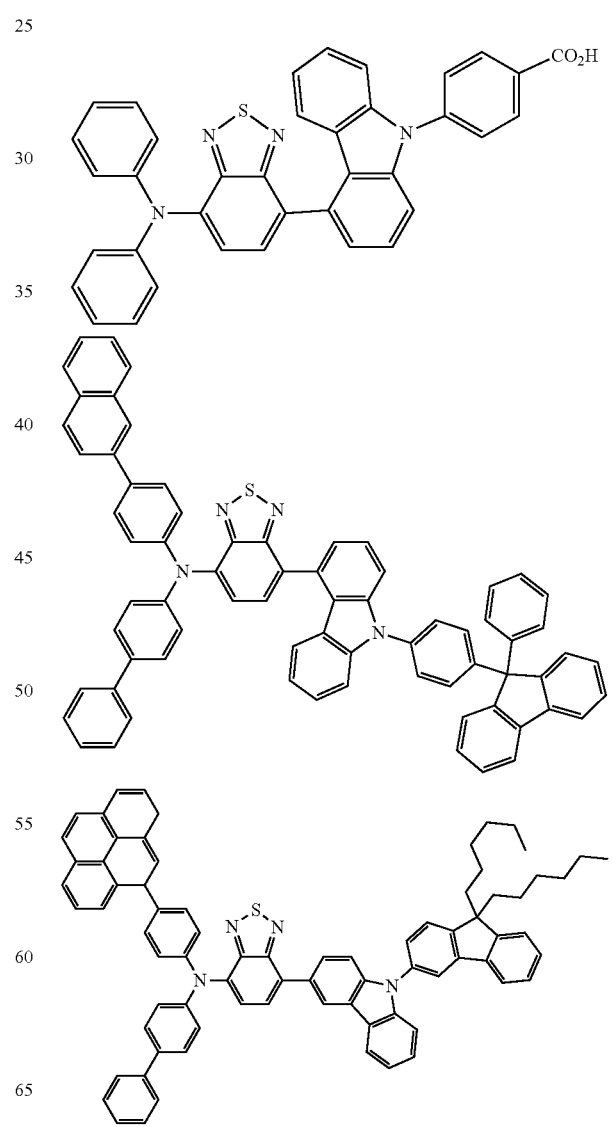

117
-continued
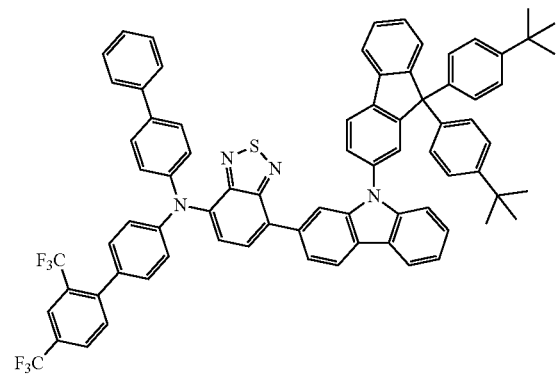
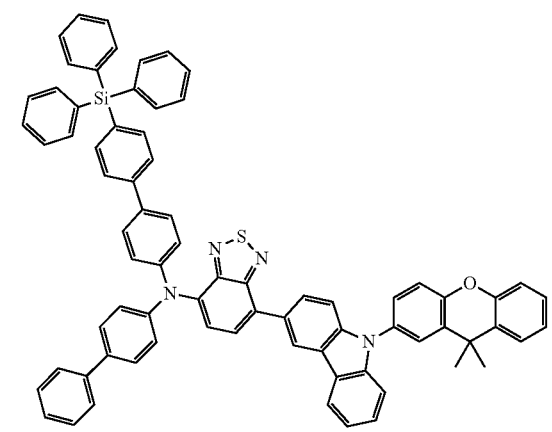
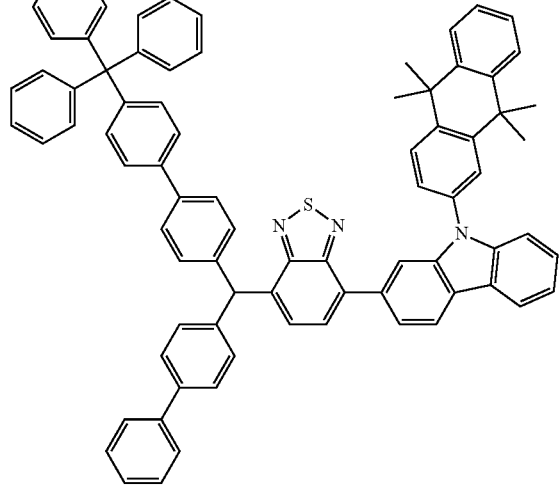
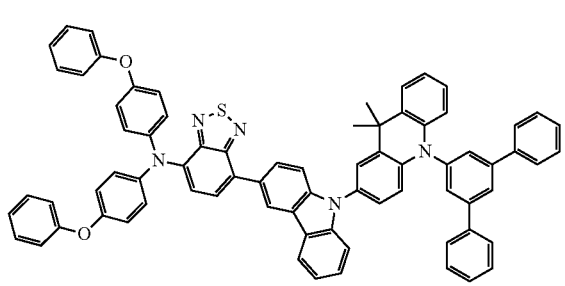
118
-continued
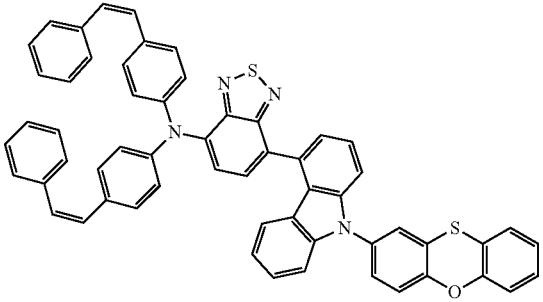
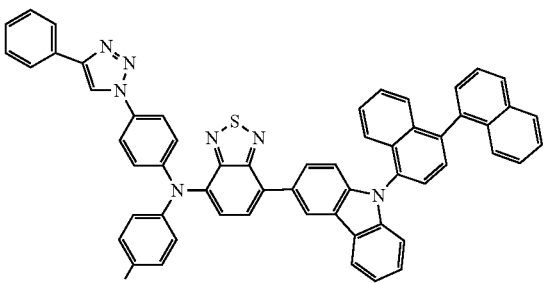
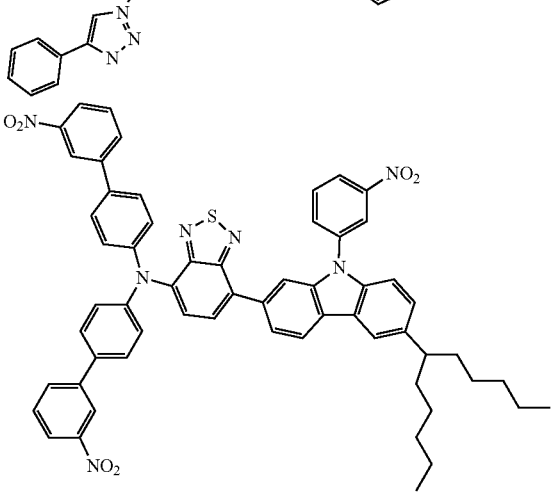

119
-continued
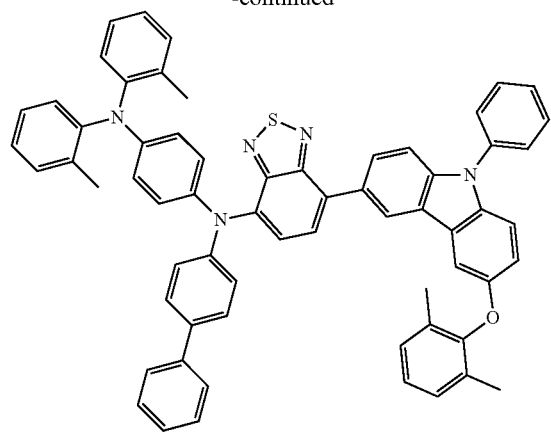
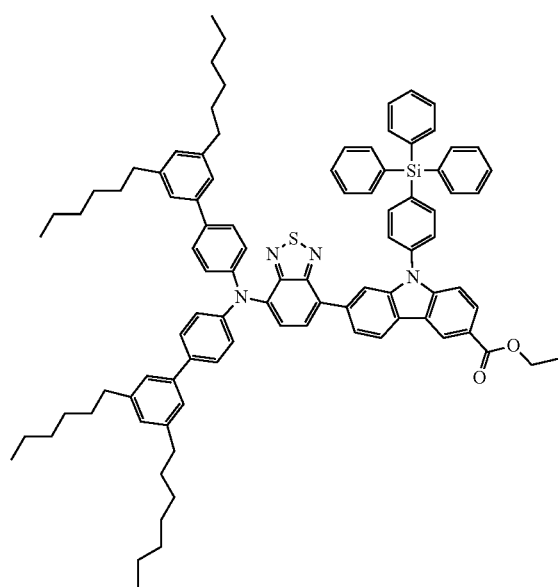
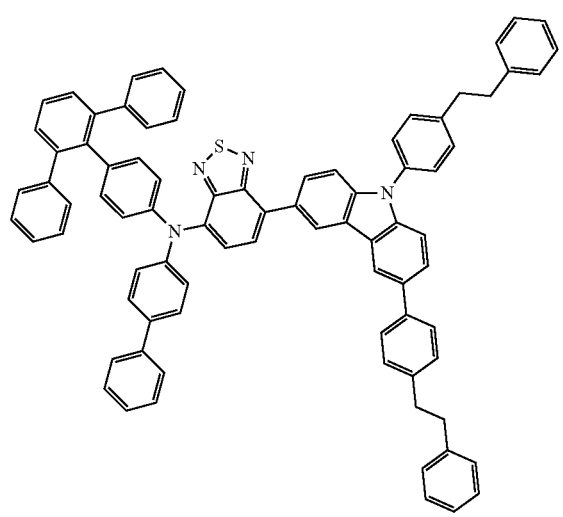
120
-continued
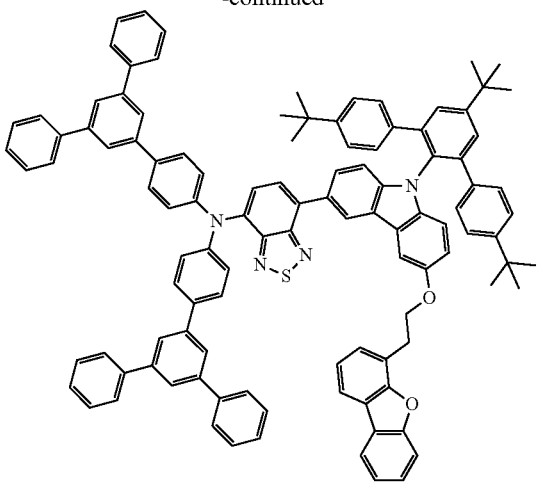
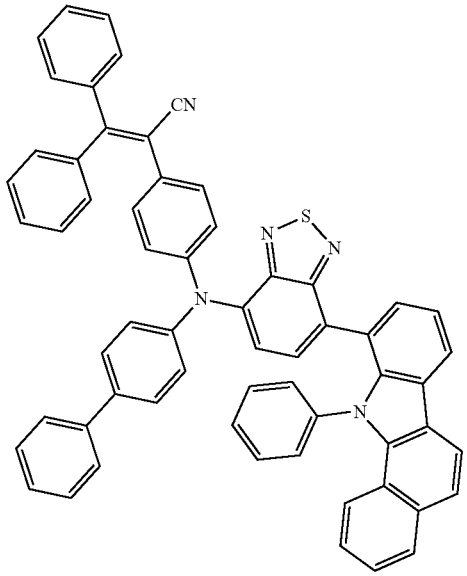
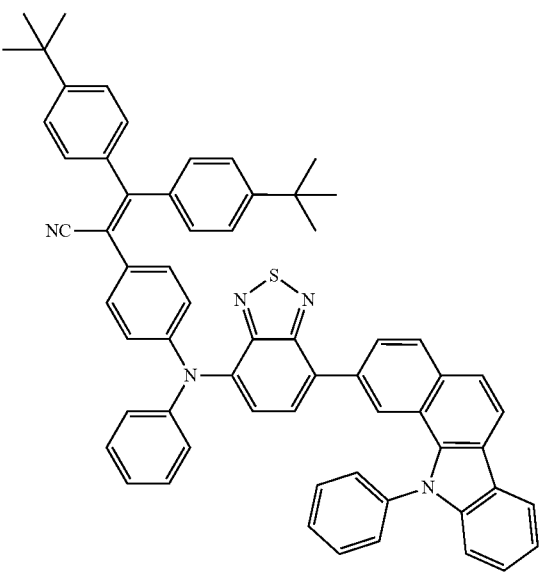

121
-continued
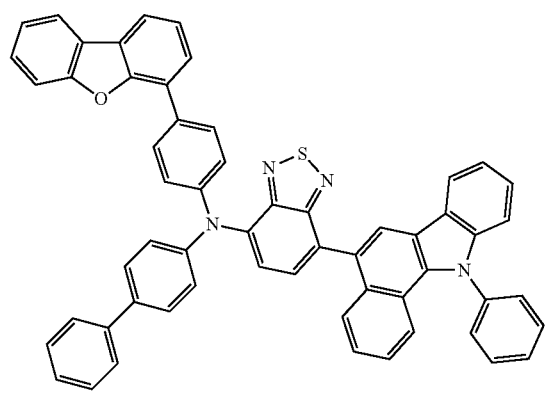
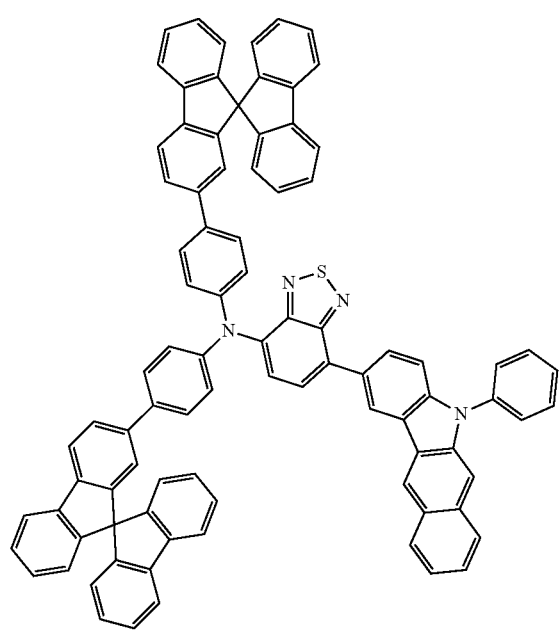
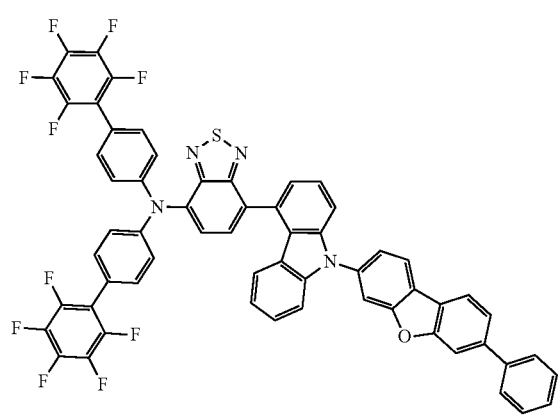
122
-continued
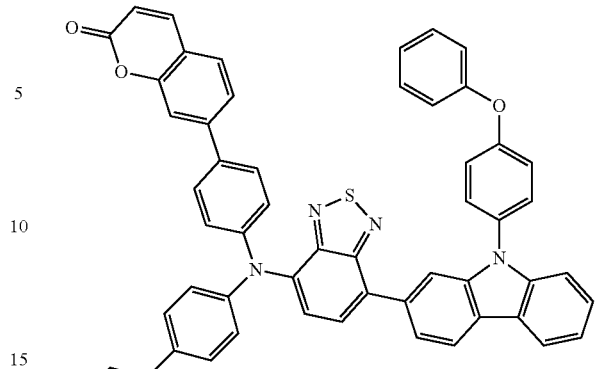
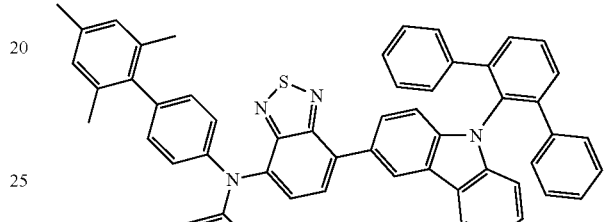
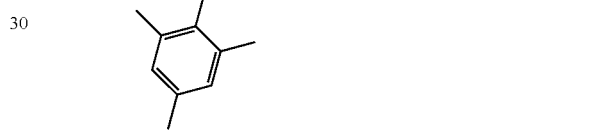
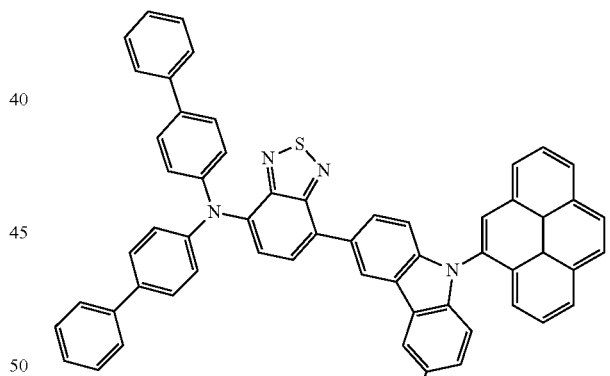
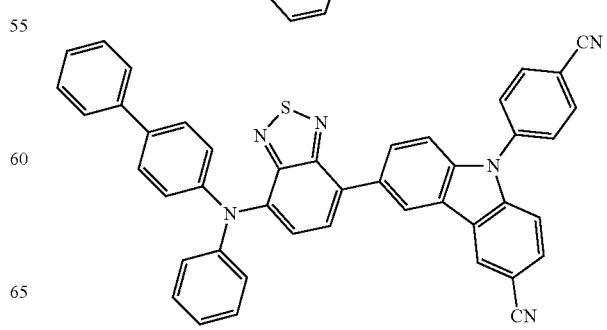

123
-continued
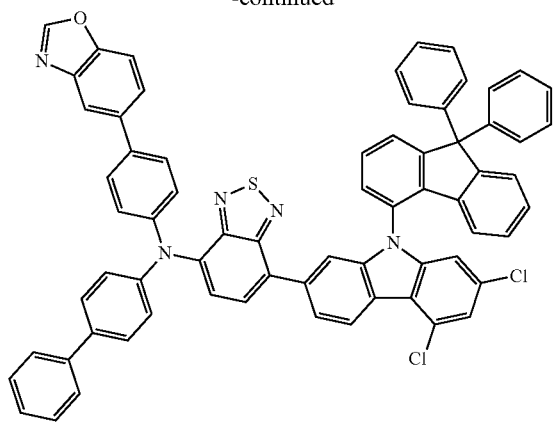
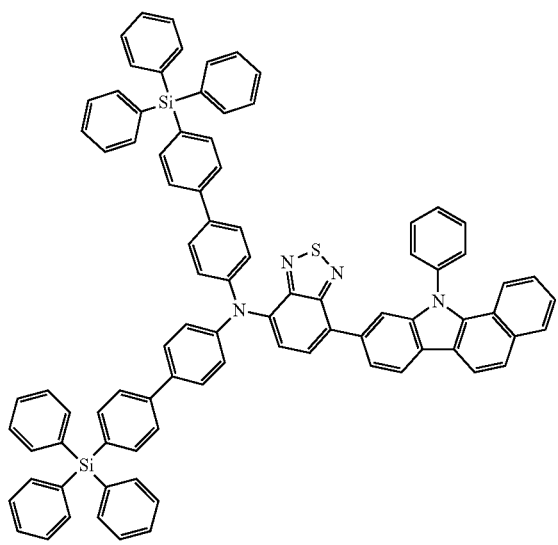
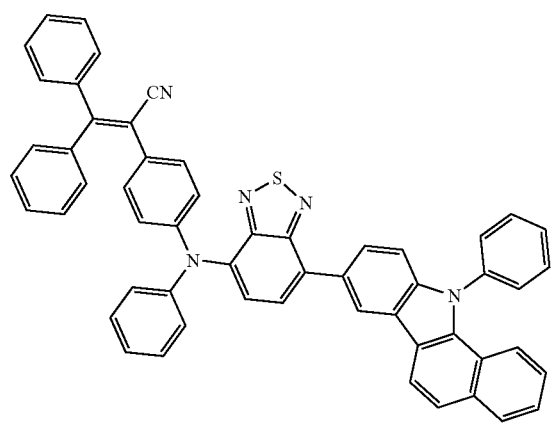
124
-continued
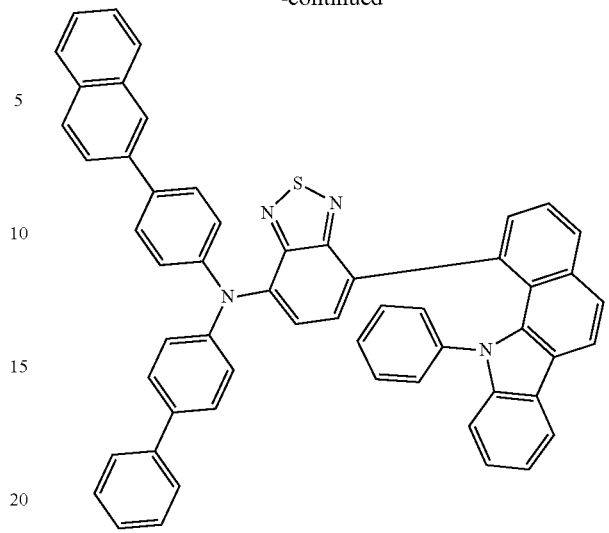
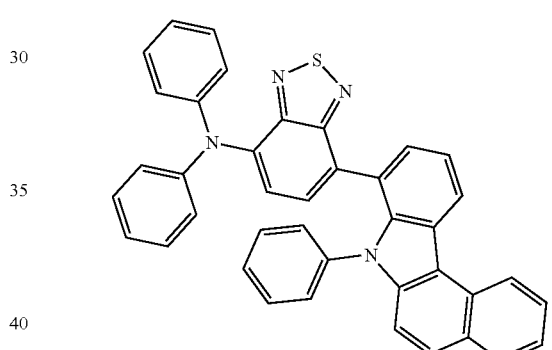
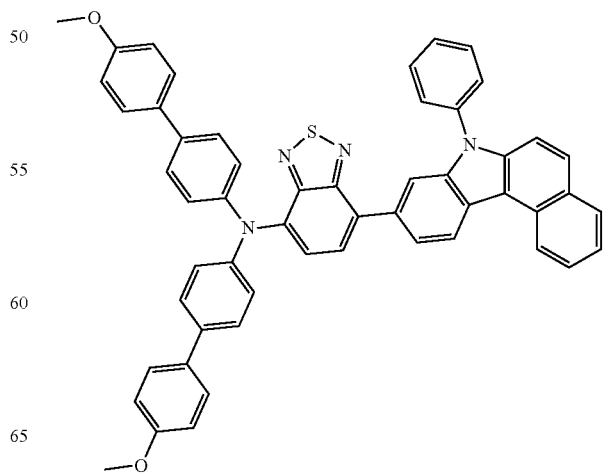

125
-continued
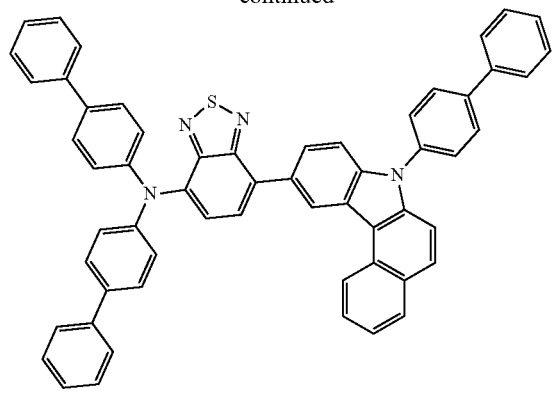
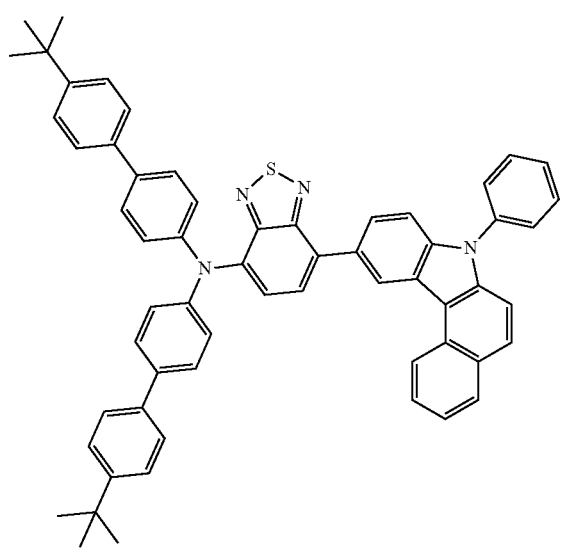
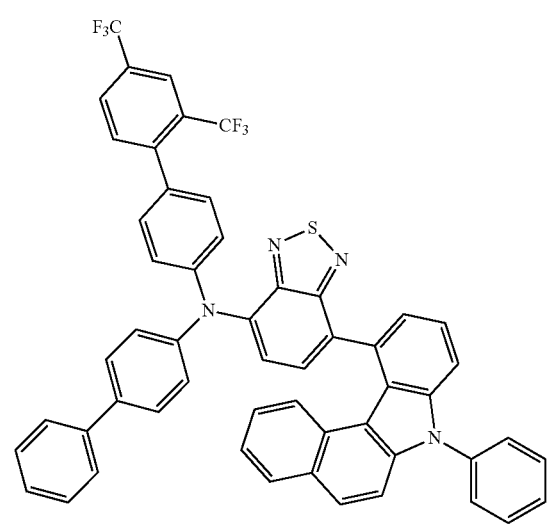
126
-continued
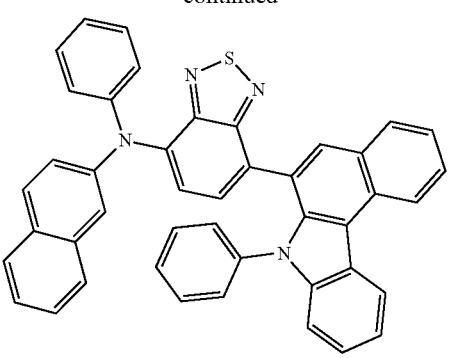
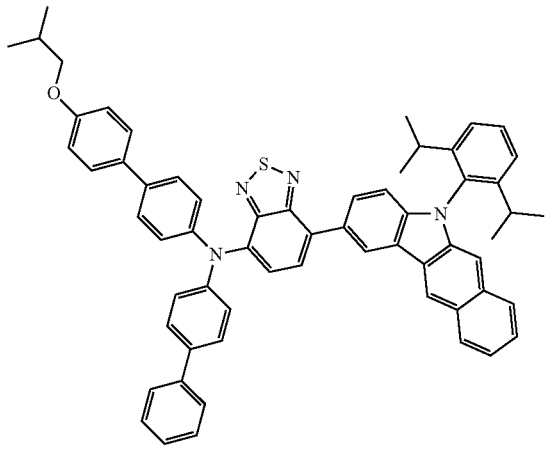

127
-continued
128
-continued
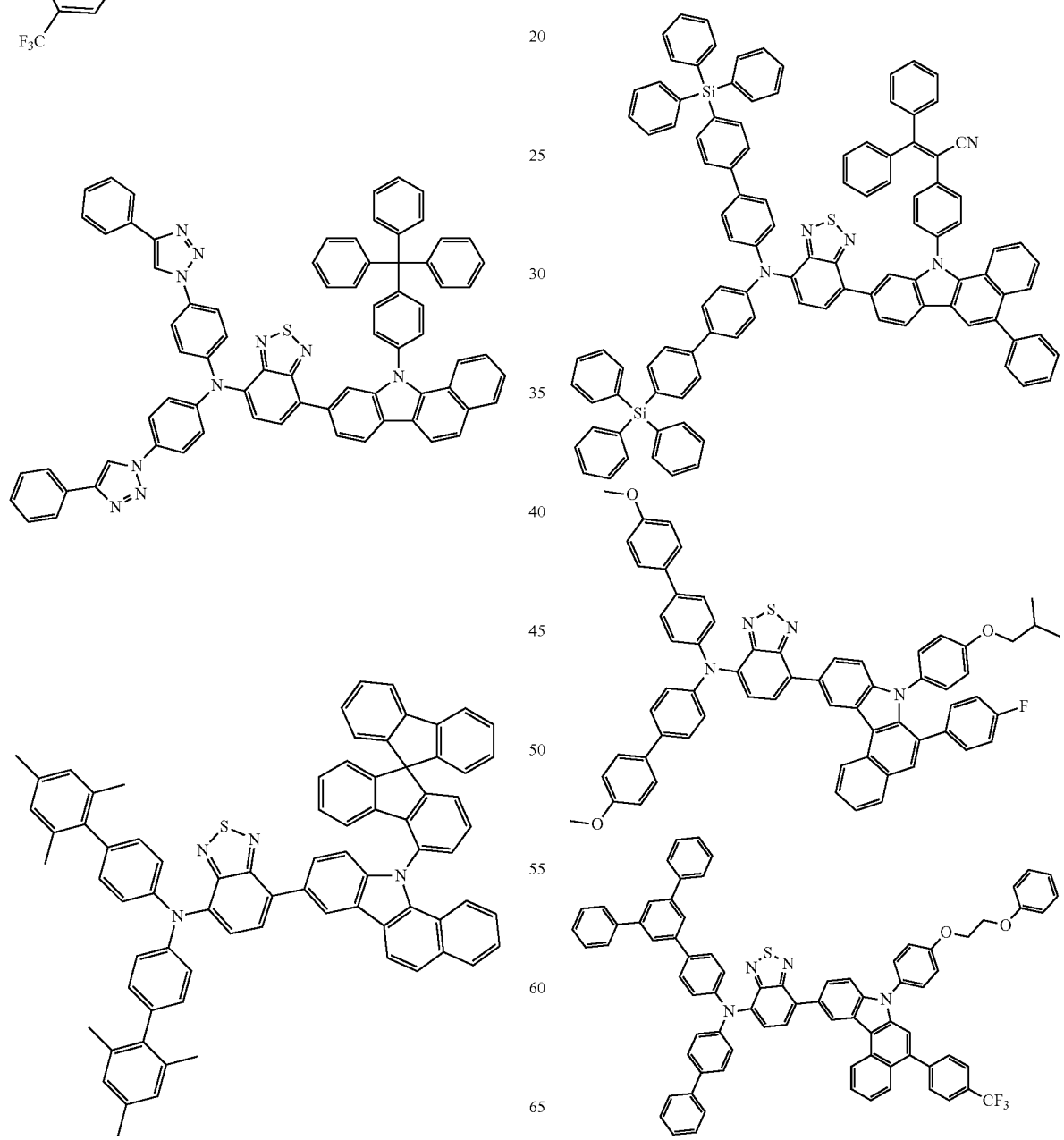

129
-continued
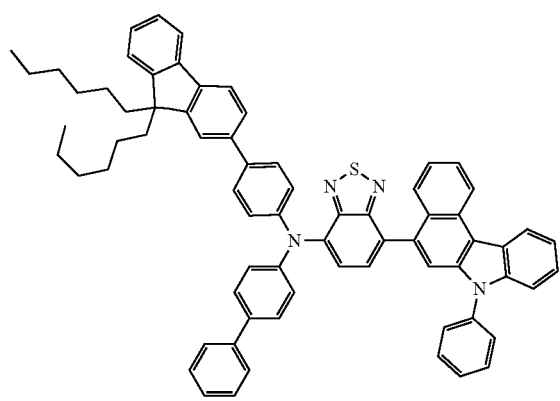
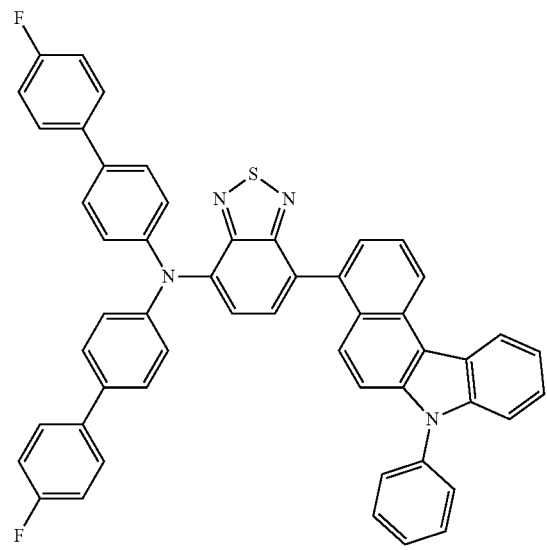
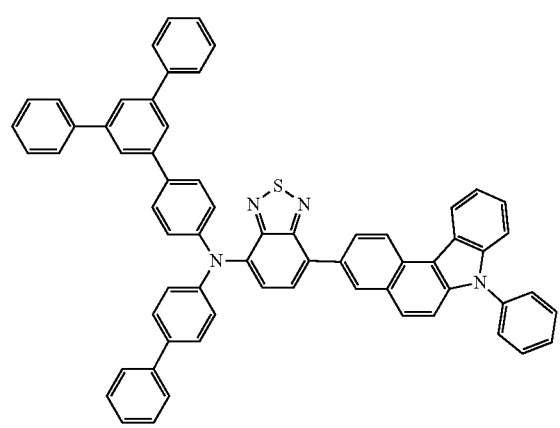
130
-continued
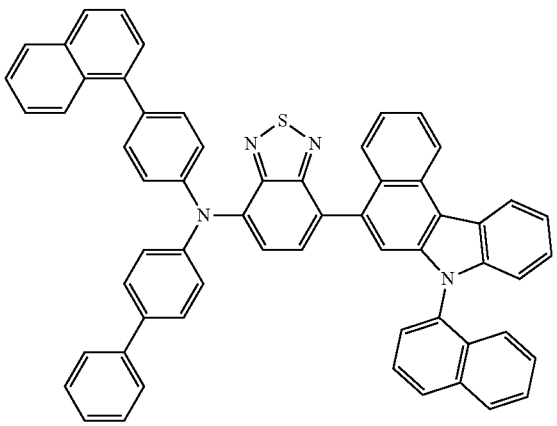
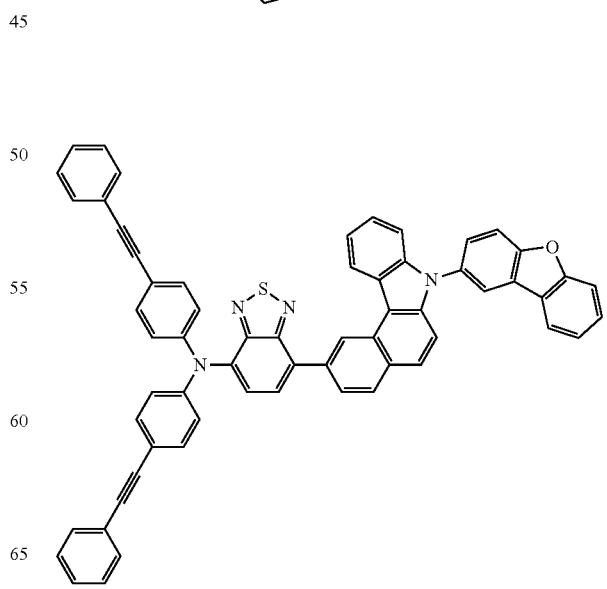

131
-continued
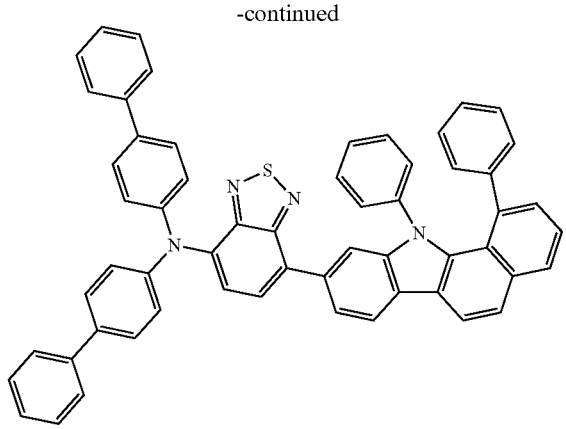
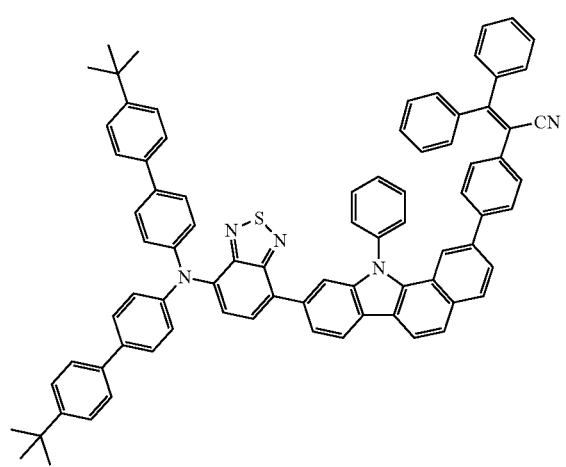
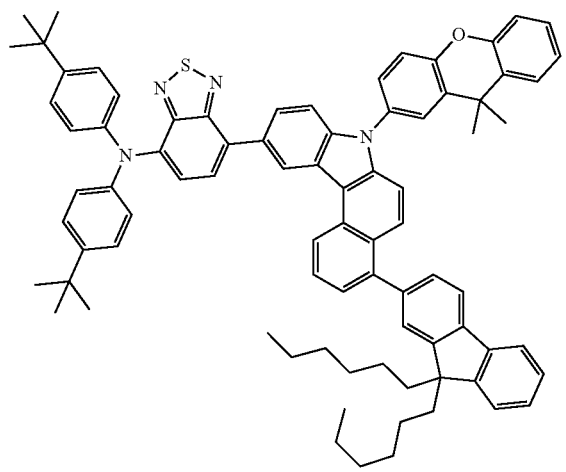
132
-continued
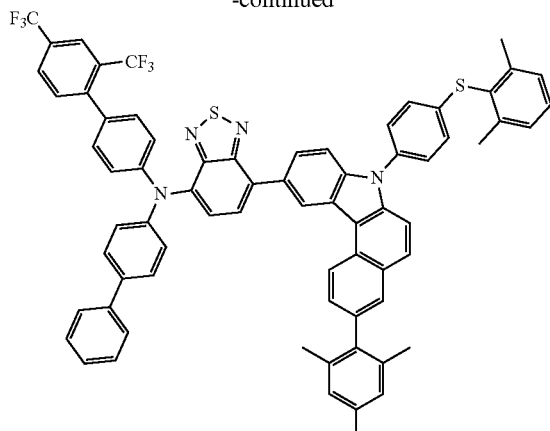
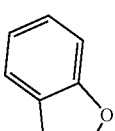
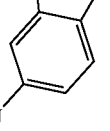
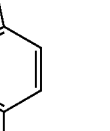
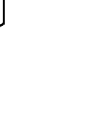
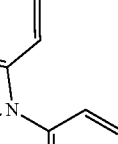

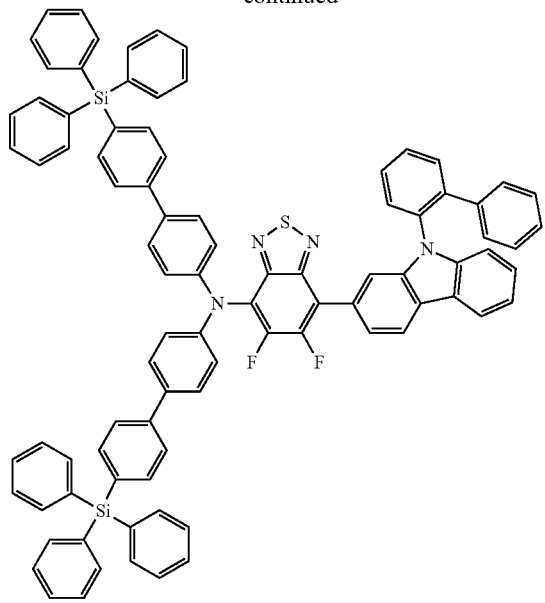

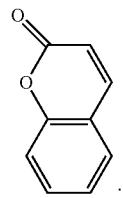

6. A color conversion film comprising:
a resin matrix; and
at least one of the compounds represented by Formula 1 of claim 1, which is dispersed in the resin matrix.

7. A backlight unit comprising the color conversion film according to claim 6.

8. A display device comprising the backlight unit according to claim 7.

9. The color conversion film of claim 6, comprising the compound of Formula 1 in a range of 0.001 wt % to 15 wt % based on the total weight of the color conversion film.

10. The color conversion film of claim 6, wherein the compound is at least one of the compounds of claim 5.

11. The color conversion film of claim 6, wherein the resin matrix is a thermoplastic polymer or a thermosetting polymer.

12. The color conversion film of claim 6, further comprising light diffusion particles selected from the group consisting of $TiO_2$, silica, borosilicate, alumina and sapphire.

13. The compound of claim 1, wherein the at least one of Ar1 and Ar2 is substituted with at least one group selected from the group of fluorine, a nitro group, a methyl group, a propyl group, a butyl group, a neopentyl group which is substituted with an aryl group, a heptyl group, an ethenyl group which is substituted with a cyano group and an aryl group, an ethenyl group which is substituted with an aryl group, an ethynyl group which is substituted with an aryl group, a triphenylsilyl group, a methoxy group which is unsubstituted or substituted with an alkyl group, a phenoxy group, an N-biphenylamine group which is substituted with an alkyl group, a fluorenyl group, a naphthyl group, a terphenyl group, a pyrenyl group, a dibenzofuranyl group, a triazolyl group which is substituted with an aryl group, a benzoxazolyl group, and 14. The compound of claim 1, wherein Z is an aryl group having 6 to 30 carbon atoms, which is unsubstituted or substituted with one or more selected from the group consisting of a halogen group, a cyano group, a silyl group, a carboxyl group (COOH), neopentyl group which is substituted with an aryl group, a propyl group which is substituted with an aryl group, an ethenyl group which is substituted with a cyano group and an aryl group, a methoxy group which is substituted with an alkyl group, an ethoxy group which is substituted with an aryloxy group, a cyclohexyl group, a sulfonyl group which is substituted with a phenyl group, an arylalkyl group, an arylthio group which is substituted with an alkyl group, a phenoxy group, a phenyl group, a naphthyl group, and a phenylanthracene group; a dihydroanthracene group which is substituted with an alkyl group; a pyridine group; a xanthene group which is substituted with an alkyl group; a dihydroacridine group which is substituted with an alkyl group and an aryl group; a phenoxathiine group; or a dibenzofuranyl group which is unsubstituted or substituted with an aryl group.

15. The compound of claim 1, wherein R is hydrogen; deuterium; chlorine; a cyano group; dodecane; an ethoxy group which is substituted with a heteroaryl group; a phenyl group which is unsubstituted or substituted with fluorine, a propyl group substituted with an aryl group, or a fluoroalkyl group; or —C(=O)ORa, or adjacent substituents may be bonded to each other to form a fluorenyl group; a phenyl group which is unsubstituted or substituted with an alkyl group or an alkenyl group substituted with a cyano group and an aryl group; or a ring having 3 to 30 carbon atoms, which is unsubstituted or substituted with a dihydroanthracene group substituted with an alkyl group, and Ra is an ethyl group which is unsubstituted or substituted with an aryl group.

16. The compound of claim 1, wherein the compound of Formula 1 is represented by Formula 2 or 3:

[Formula 2]

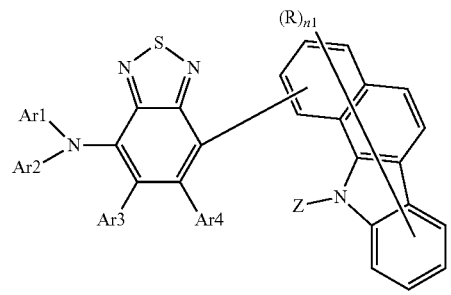

-continued
[Formula 3]
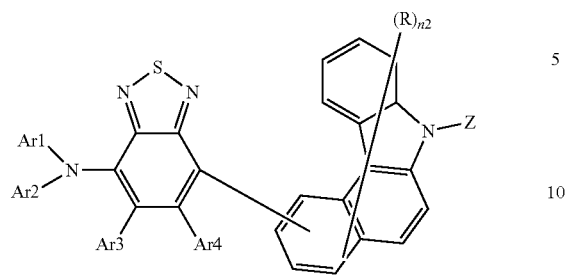
wherein Ar1 to Ar4, R, and Z are as defined in claim 1 and n1 and n2 are an integer from 0 to 9.
* * * * *